(12) United States Patent
Shaw et al.

(10) Patent No.: US 8,367,651 B2
(45) Date of Patent: *Feb. 5, 2013

(54) SOLID GANAXOLONE FORMULATIONS AND METHODS FOR THE MAKING AND USE THEREOF

(75) Inventors: Kenneth Shaw, Weston, CT (US); Mingbao Zhang, Millwood, NY (US)

(73) Assignee: Marinus Pharmaceuticals, Branford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/052,798

(22) Filed: Mar. 21, 2011

(65) Prior Publication Data
US 2011/0236487 A1   Sep. 29, 2011

Related U.S. Application Data

(63) Continuation of application No. 11/605,700, filed on Nov. 28, 2006, now Pat. No. 8,022,054.

(60) Provisional application No. 60/758,171, filed on Jan. 11, 2006, provisional application No. 60/740,174, filed on Nov. 28, 2005, provisional application No. 61/740,208, filed on Nov. 28, 2005.

(51) Int. Cl.
*A01N 43/00* (2006.01)
*A61K 31/33* (2006.01)

(52) U.S. Cl. ........ 514/183; 514/182; 977/775; 977/906; 424/489

(58) Field of Classification Search ........................ None
See application file for complete search history.

(56) References Cited

U.S. PATENT DOCUMENTS

| | | | |
|---|---|---|---|
| 2,671,750 A | 3/1954 | Macek et al. | |
| 4,540,602 A | 9/1985 | Motoyama et al. | 427/213.31 |
| 4,783,484 A | 11/1988 | Violante et al. | 514/535 |
| 4,826,689 A | 5/1989 | Violanto | 424/489 |
| 4,997,454 A | 3/1991 | Violante et al. | 23/305 A |
| 5,145,684 A | 9/1992 | Liversidge et al. | 424/489 |
| 5,209,746 A | 5/1993 | Balaban et al. | 604/892.1 |
| 5,213,808 A | 5/1993 | Bar-Shalom et al. | 424/473 |
| 5,221,278 A | 6/1993 | Linkwitz et al. | 604/890.1 |
| 5,260,068 A | 11/1993 | Chen | 424/451 |
| 5,260,069 A | 11/1993 | Chen | 424/451 |
| 5,298,262 A | 3/1994 | Na et al. | 424/489 |
| 5,299,131 A | 3/1994 | Haas et al. | 364/426.03 |
| 5,308,348 A | 5/1994 | Balaban et al. | 604/892.1 |
| 5,312,390 A | 5/1994 | Wong | 604/892.1 |
| 5,318,588 A | 6/1994 | Horzewski et al. | 606/198 |
| 5,340,590 A | 8/1994 | Wong et al. | 424/473 |
| 5,346,702 A | 9/1994 | Na et al. | 424/490 |
| 5,352,459 A | 10/1994 | Hollister et al. | 424/489 |
| 5,356,467 A | 10/1994 | Oshlack et al. | 106/161.1 |
| 5,391,381 A | 2/1995 | Wong et al. | 424/473 |
| 5,399,363 A | 3/1995 | Liversidge et al. | 424/490 |
| 5,429,824 A | 7/1995 | June | 424/489 |
| 5,445,829 A | 8/1995 | Paradissis et al. | 424/480 |
| 5,456,679 A | 10/1995 | Balaban et al. | 604/892.1 |
| 5,470,583 A | 11/1995 | Na et al. | 424/489 |
| 5,472,708 A | 12/1995 | Chen | 424/451 |
| 5,494,683 A | 2/1996 | Liversidge et al. | 424/490 |
| 5,508,040 A | 4/1996 | Chen | 424/451 |
| 5,510,118 A | 4/1996 | Bosch et al. | 424/489 |
| 5,518,187 A | 5/1996 | Bruno et al. | 241/5 |
| 5,534,270 A | 7/1996 | De Castro | 424/490 |
| 5,543,133 A | 8/1996 | Swanson et al. | 424/9.45 |
| 5,560,932 A | 10/1996 | Bagchi et al. | 424/489 |
| 5,573,783 A | 11/1996 | Desieno et al. | 424/490 |
| 5,662,883 A | 9/1997 | Bagchi et al. | 424/9.4 |
| 5,665,331 A | 9/1997 | Bagchi et al. | 424/9.45 |
| 5,672,360 A | 9/1997 | Sackler et al. | 424/490 |
| 5,718,388 A | 2/1998 | Czekai et al. | 241/21 |
| 5,741,522 A | 4/1998 | Violante et al. | 424/489 |
| 5,776,496 A | 7/1998 | Violante et al. | 424/489 |
| 5,840,329 A | 11/1998 | Bai | 424/458 |
| 5,862,999 A | 1/1999 | Czekai et al. | 241/21 |
| 5,980,508 A | 11/1999 | Cardamone et al. | 604/890.1 |
| 6,039,979 A | 3/2000 | Gendrot et al. | 424/497 |
| 6,214,379 B1 | 4/2001 | Hermelin | 424/464 |
| 6,228,398 B1 | 5/2001 | Devane et al. | 424/484 |
| 6,248,363 B1 | 6/2001 | Patel et al. | 424/497 |
| 6,264,922 B1 | 7/2001 | Wood et al. | |
| 6,267,989 B1 | 7/2001 | Liversidge et al. | 424/489 |
| 6,316,029 B1 | 11/2001 | Jain et al. | 424/484 |
| 6,375,986 B1 | 4/2002 | Ryde et al. | 424/489 |
| 6,428,814 B1 | 8/2002 | Bosch et al. | 424/501 |
| 6,432,381 B2 | 8/2002 | Liversidge et al. | 424/1.29 |
| 6,514,518 B2 | 2/2003 | Monkhouse et al. | 424/427 |
| 6,569,463 B2 | 5/2003 | Patel et al. | 424/497 |
| 6,592,903 B2 | 7/2003 | Ryde et al. | 424/489 |
| 6,607,751 B1 | 8/2003 | Odidi et al. | 424/488 |
| 6,627,223 B2 | 9/2003 | Percel et al. | 424/471 |
| 6,682,759 B2 | 1/2004 | Lim et al. | 424/468 |

(Continued)

FOREIGN PATENT DOCUMENTS

| EP | 0169618 | 11/1993 |
|---|---|---|
| EP | 0498824 | 1/1994 |

(Continued)

OTHER PUBLICATIONS

MG Soni, SL Taylor, NA Greenberg, GA Burdock. "Evaluation of the health aspects of methyl paraben: a review of the published literature." Food and Chemical Toxicology, vol. 40, 2002, pp. 1335-1373.
JOH Sham, Y Zhang, WH Finlay, WH Roa, R Lobenberg. "Formulation and characterization of spray-dried powders containing nanoparticles for aerosol delivery to the lung." International Journal of Pharmaceutics, vol. 269, 2004, pp. 457-467.
A Valotis, K Neukam, O Elert, P Hogger. "Human Receptor Kinetics, Tissue Binding Affinity, and Stability of Mometasone Furoate." Journal of Pharmaceutical Sciences, vol. 93, No. 5, May 2004, pp. 1337-1350.

(Continued)

*Primary Examiner* — Brandon Fetterolf
*Assistant Examiner* — Jean Cornet
(74) *Attorney, Agent, or Firm* — Davidson, Davidson & Kappel, LLC

(57) ABSTRACT

In certain embodiments, the invention is directed to composition comprising stable particles comprising ganaxolone, wherein the volume weighted median diameter (D50) of the particles is from about 50 nm to about 500 nm.

51 Claims, 4 Drawing Sheets

U.S. PATENT DOCUMENTS

| | | | |
|---|---|---|---|
| 6,689,378 B1 | 2/2004 | Sun et al. | 424/443 |
| 6,730,325 B2 | 5/2004 | Devane et al. | 424/489 |
| 6,793,936 B2 | 9/2004 | Devane et al. | 424/484 |
| 6,902,742 B2 | 6/2005 | Devane et al. | 424/484 |
| 6,908,626 B2 | 6/2005 | Cooper et al. | 424/489 |
| 6,923,988 B2 | 8/2005 | Patel et al. | 424/489 |
| 6,969,529 B2 | 11/2005 | Bosch et al. | 424/489 |
| 6,976,647 B2 | 12/2005 | Reed et al. | 241/30 |
| 7,078,057 B2 | 7/2006 | Kerkhof | 424/489 |
| 7,198,795 B2 | 4/2007 | Cooper et al. | 424/400 |
| 2002/0012675 A1 | 1/2002 | Jain et al. | 424/400 |
| 2002/0150616 A1 | 10/2002 | Vandecruys | 424/464 |
| 2003/0054042 A1 | 3/2003 | Liversidge et al. | 424/489 |
| 2003/0129242 A1 | 7/2003 | Bosch et al. | |
| 2003/0215502 A1 | 11/2003 | Pruss et al. | 424/465 |
| 2004/0067251 A1 | 4/2004 | Johnston et al. | 424/465 |
| 2004/0105889 A1 | 6/2004 | Ryde et al. | 424/489 |
| 2004/0214746 A1 | 10/2004 | Bosch et al. | 514/1 |
| 2004/0224020 A1 | 11/2004 | Sschoenhard | 424/471 |
| 2004/0258757 A1 | 12/2004 | Bosch et al. | 424/489 |
| 2005/0031691 A1 | 2/2005 | McGurk et al. | 424/484 |
| 2005/0118268 A1 | 6/2005 | Percel et al. | 424/471 |
| 2005/0181050 A1 | 8/2005 | Hirsh et al. | 424/469 |
| 2005/0226927 A1 | 10/2005 | Han et al. | 424/468 |
| 2006/0003005 A1 | 1/2006 | Cao et al. | 424/470 |
| 2006/0216353 A1 | 9/2006 | Liversidge et al. | 424/489 |
| 2007/0148252 A1 | 6/2007 | Shaw et al. | 424/489 |
| 2009/0004262 A1 | 1/2009 | Shaw et al. | 424/456 |

FOREIGN PATENT DOCUMENTS

| | | |
|---|---|---|
| EP | 0499299 | 8/2000 |
| EP | 0580690 | 9/2000 |
| WO | 9526715 | 10/1995 |
| WO | 9857648 | 12/1998 |
| WO | 0145677 | 6/2001 |

OTHER PUBLICATIONS

An Office Action, dated Mar. 15, 2012, issued in connection with corresponding U.S. Appl. No. 12/777,920.

H. Steffen BT Gattefosse No. 81 pp. 45-53 (1988).

International Search Report and the Written Opinion corresponding to International Application No. PCT/US07/24606.

U.S. Appl. No. 11/606,222 Specification (192 pages including 21 pages of claims, 1 Abstract page and 4 pages of figures).

U.S. Appl. No. 11/998,362 Specification (155 pages including 8 pages of claims, 1 Abstract page and 5 pages of figures).

Preliminary Amendment filed Apr. 4, 2008 (10 pages) for U.S. Appl. No. 11/998,362.

Applicant's Response to Office Action dated Oct. 19, 2010 filed in corresponding U.S. Appl. No. 11/605,700.

Office Action dated Aug. 12, 2010 issued in corresponding U.S. Appl. No. 11/605,700.

Applicant's Response to Office Action dated Jun. 4, 2010 filed in corresponding U.S. Appl. No. 11/605,700.

Office Action dated Jan. 21, 2010 issued in corresponding U.S. Appl. No. 11/605,700.

Applicant's Response to Office Action dated Oct. 9, 2009 filed in corresponding U.S. Appl. No. 11/605,700.

Office Action dated Jul. 8, 2009 issued in corresponding U.S. Appl. No. 11/605,700.

Applicant's Response to Office Action dated Dec. 16, 2008 filed in corresponding U.S. Appl. No. 11/605,700.

Delmar Learning's Pharmacy Technician Certification Exam Review, Edition 2, 2003, 584 pages by Patricia K. Anthony.

Applicants' Response to Office Action dated Sep. 27, 2010 filed in connection with corresponding U.S. Appl. No. 12/606,222.

An Office Action dated Aug. 13, 2010 issued in connection with corresponding U.S. Appl. No. 12/606,222.

Applicants' Response to Office Action dated Jun. 4, 2010 filed in connection with corresponding U.S. Appl. No. 12/606,222.

An Office Action dated Feb. 4, 2010 issued in connection with corresponding U.S. Appl. No. 12/606,222.

Applicant's Response to Office Action dated Oct. 13, 2009 filed in connection with corresponding U.S. Appl. No. 12/606,222.

An Office Action dated Jul. 10, 2009 issued in connection with corresponding U.S. Appl. No. 12/606,222.

Applicants' Response to Office Action dated Mar. 24, 2009 filed in connection with corresponding U.S. Appl. No. 12/606,222.

FIGURE 1. Curing Process of Ganaxalone-Preservative Particles at Ambient Temperature: Particle Size Growth Was Partially Reversed by 1 minute Sonication (Power Setting: Low) in the Early Stage of the Curing Process.
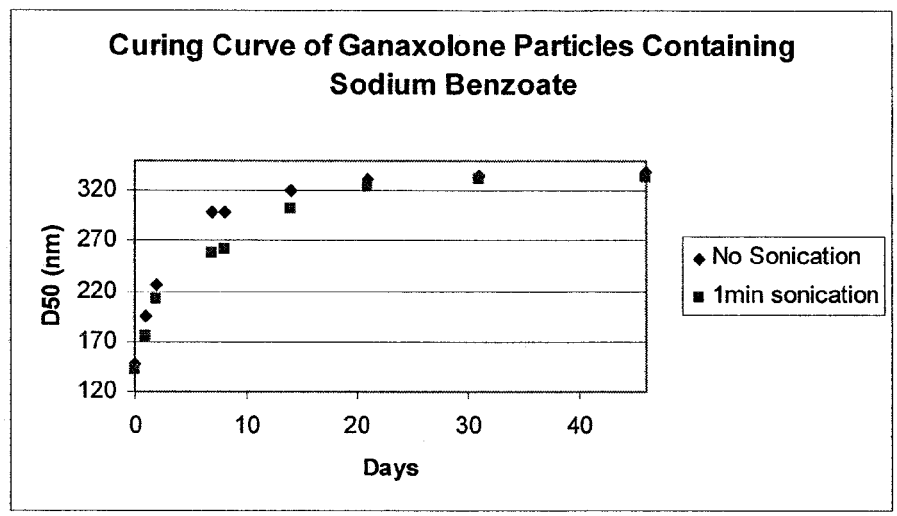
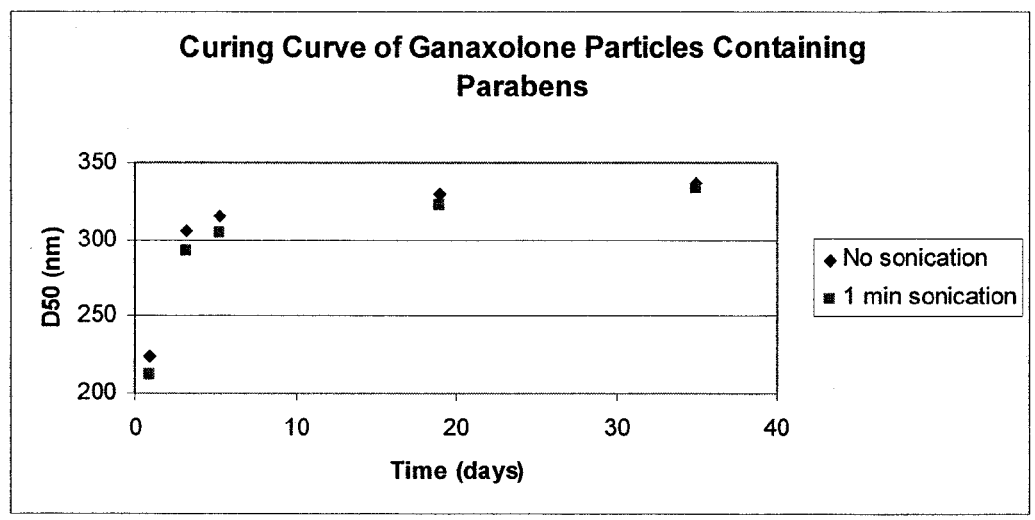

FIGURE 2. Curing of Parabens Preserved and Sodium Benzoate Preserved Ganaxalone Particles at Ambient Temperature: Parabens Preserved Ganaxolone Particles Become Fully Stable in 5-7 Days While the Benzoate Preserved Particles Take About 3 Weeks To Become Fully Stable (D50 Were Unsonicated).

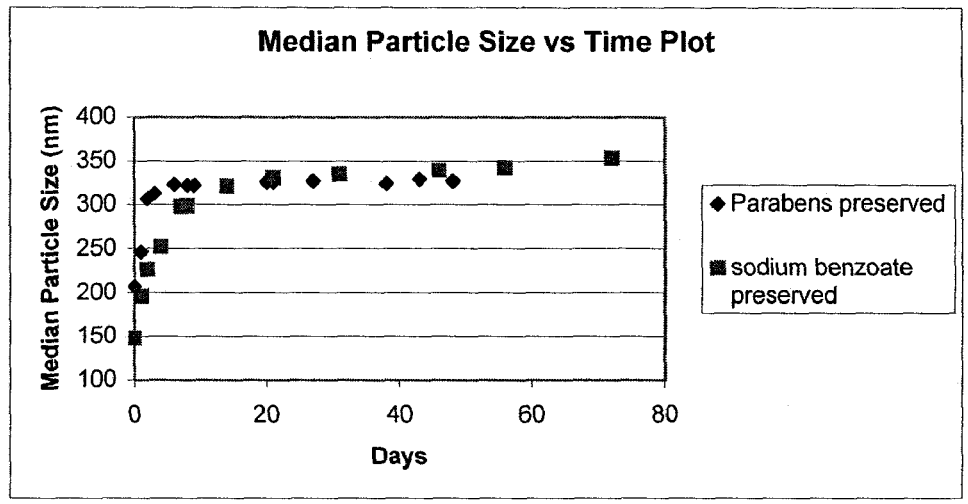

FIGURE 3. Stability plots (D50 vs time) of ganaxolone particles containing no complexing agent: ganaxolone particles without a complexing agent that were milled for less than 2 hours of milling residence time continued to increase gradually in size over a number of months, while the particles milled for more than 2 hours of residence time did not change over six months.

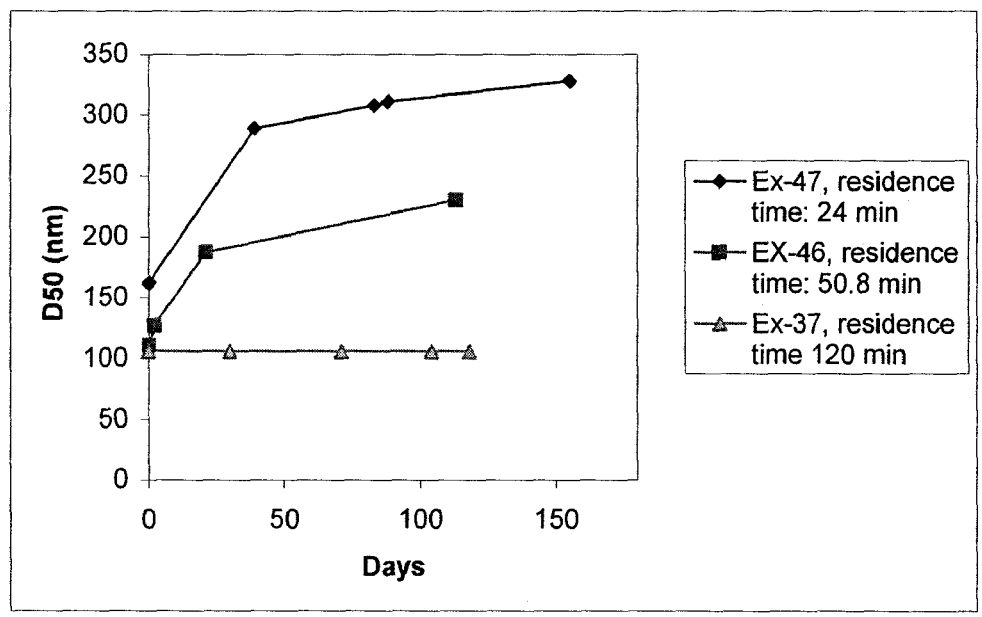

FIGURE 4. Measured D50 values for ganaxolone particles as a function of milling residence time for a typical milling run using a DYNO-Mill KDL equipped with four 64 mm polyurethane agitator discs.
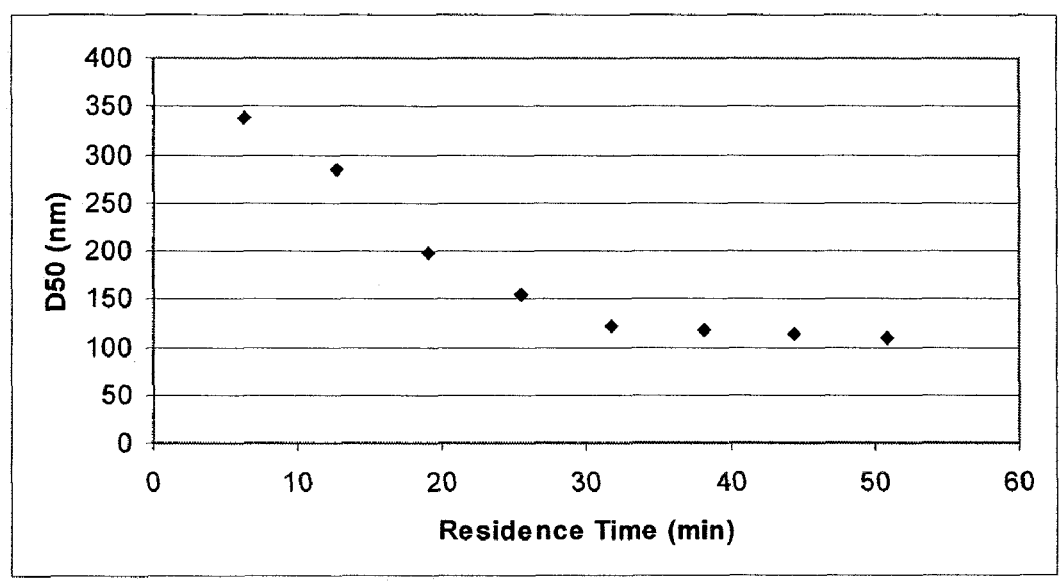

FIGURE 5. Particle Size Distribution (after 1min Low Power Sonication) of Re-suspended Solid Dosage Forms Containing Sodium Chloride in SGF at Room Temperature: With and Without a Complexing Agent (Methylparaben)
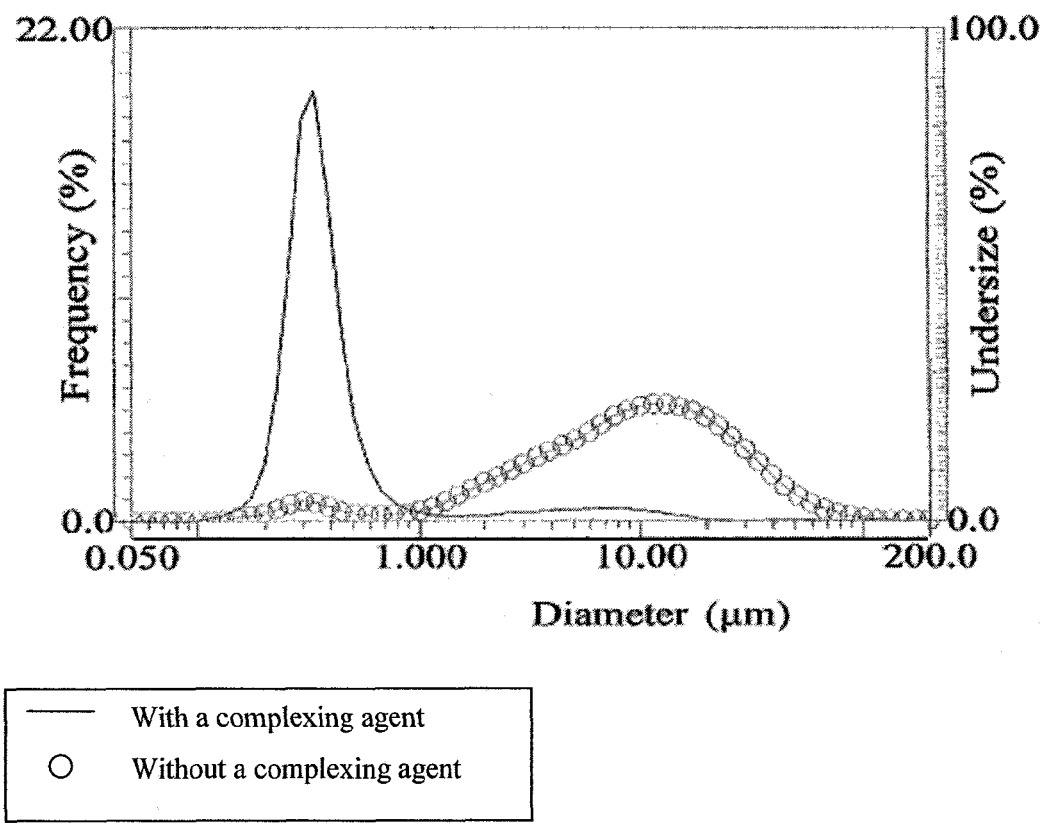

SOLID GANAXOLONE FORMULATIONS AND METHODS FOR THE MAKING AND USE THEREOF

CROSS-REFERENCE TO RELATED APPLICATIONS

This application is a continuation of U.S. patent application Ser. No. 11/605,700 filed Nov. 28, 2006 now U.S. Pat. No. 8,022,054; which claims priority from U.S. Provisional Application No. 60/758,171, filed Jan. 11, 2006; U.S. Provisional Application No. 60/740,174, filed Nov. 28, 2005; and U.S. Provisional Application No. 60/740,208, filed Nov. 28, 2005, the disclosures of which are all hereby incorporated by reference in their entireties for all purposes.

FIELD OF THE INVENTION

Described herein are ganaxolone formulations which provide enhanced stability, physical and chemical properties and can provide enhanced pharmacokinetic properties to achieve an optimal balance between pharmacodynamic and side effect profiles in mammals, and dosage forms containing the same, as well as methods of making ganaxolone formulations and their use in the treatment of epilepsy-related and other central nervous system disorders.

BACKGROUND OF THE INVENTION

Positive modulators of $GABA_A$ receptors have long been used in the treatment of disorders of the central nervous system, including epilepsy, anxiety, sleep disorders, abnormal muscle tone including spasticity, and the alcohol withdrawal syndrome (Macdonald and Olsen, 1994; Mehta and Ticku, 1999; Mohler et al., 2001). Such pharmacological agents also have medical uses to induce anesthesia and amnesia (Chapouthier and Venault, 2002; Rudolph and Antkowiak, 2004). Typical positive modulators of $GABA_A$ receptors include neuroactive steroids, benzodiazepines, non-benzodiazepine benzodiazepine-site agonists, barbiturates, propofol, chlormethiazol, and anesthetic agents such as etomidate, propofol, isoflurane and sevoflurane (Trapani et al., 2000; Lambert et al., 2003; Hemmings et al., 2005; Johnston, 2005; Rudolph and Antkowiak, 2005). γ-Aminobutyric acid (GABA) is the major inhibitory neurotransmitter in the nervous system. GABA acts on several targets, including $GABA_A$ receptors. $GABA_A$ receptors are ionotropic receptors that transport chloride ions across neuronal cell membranes, which induce hyperpolarization and shunts excitatory inputs, thus inhibiting the excitability of neurons. $GABA_A$ receptors are heteropentamers that are generally composed of three of more different subunits. The subunit composition of $GABA_A$ receptors is a major determinant of the pharmacological sensitivity of the receptor (Mohler et al., 2001; Sieghart and Sperk, 2002). For example, sensitivity to benzodiazepines and non-benzodiazepine benzodiazepine-site agonists requires the presence of a γ2 subunit and there is no responsiveness if α4 or α6 subunits substitutes for the more common α1, α2 and α3 subunits. By contrast neuroactive steroids that act as $GABA_A$ receptor positive modulators do not require α2 and are sensitive even if receptors contain α4 and α6 (Lambert et al., 2003). Although $GABA_A$ receptors that contain the δ subunit do not respond to benzodiazepines or benzodiazepine-site ligands, (Jones-Davis et al., 2005), they are more sensitive to neurosteroids than are receptors containing the more abundant γ2L subunit (Adkins et al., 2001; Brown et al., 2002; Wohlfarth et al., 2002).

Neurosteroids, and particularly ganaxolone, act on different populations of $GABA_A$ receptors than do benzodiazepines. The distribution of benzodiazepine sensitive $GABA_A$ receptors is distinct in the brain from the distribution of neuroactive steroid sensitive receptors (Sieghart and Sperk, 2002). In addition, benzodiazepines enhance the physiological activity of $GABA_A$ receptors through different effects on the gating of the receptor than do neuroactive steroids (Twyman and Macdonald, 1992; Wohlfarth et al., 2002). Barbiturates act preferentially on $GABA_A$ receptors containing δ subunits as partial agonists (Feng et al., 2002, 2004). However, barbiturates, unlike benzodiazepines and neurosteroids, act on other molecular targets than $GABA_A$ receptors, most notably voltage-dependent calcium channels (French-Mullen et al., 1993; Rudolph and Antkowiak, 2005). Thus, the major classes of drugs that act on $GABA_A$ receptors each have distinct spectrums of activity, and neuroactive steroids act on a set of targets that does not overlap with any other class. In addition, pharmacological studies have shown that these various classes of drugs interact with heteromeric $GABA_A$ receptor complexes at pharmacologically distinguishable sites (Lambert et al., 2003). Specifically, the actions of neuroactive steroids occur at sites on $GABA_A$ receptors that are distinct from the site of action of benzodiazepines or barbiturates. Another important distinction between the mode of action of benzodiazepines and neuroactive steroids is that benzodiazepine appears to act largely at synaptic $GABA_A$ receptors and thus directly modulate inhibitory GABAergic. By contrast, neuroactive steroids may act more prominently on extrasynaptic or perisynaptic $GABA_A$ receptors that do not mediate inhibitory synaptic transmission, but rather generate a tonic chloride current that sets the general level of excitability of the neuron (Stell et al., 2003; Ferrant and Nusser, 2005).

Neuroactive steroids have a different pattern of selectivity for the various $GABA_A$ receptor isoforms (subunit combinations) from other types of positive allosteric modulators of $GABA_A$ receptors. In addition, the functional effects of neuroactive steroids differ from those of other $GABA_A$ receptor modulators. For example, neuroactive steroids have greater efficacy than benzodiazepines (Kokate et al., 1994) and they act in specific ways to alter the gating of $GABA_A$ receptors (Bianchi and Macdonald, 2003). Neuroactive steroids are not known to affect other ion channels and receptor systems within the same range of concentrations at which they affect $GABA_A$ receptors, whereas other $GABA_A$ receptor modulators have effects on diverse molecular targets. An additional difference between neuroactive steroids and other $GABA_A$ receptor positive modulators is that tolerance does not occur to the anticonvulsant effects neuroactive steroids in general (Kokate et al., 1998) and the neurosteroid ganaxolone in particular (Reddy and Rogawski, 2000). Tolerance does occur to the sedative effects of ganaxolone in human subjects (Monaghan et al., 1999). By contrast, tolerance develops rapidly to the sedative activity of benzodiazepines and more slowly to their anticonvulsant activity.

Ganaxolone, a neurosteroid also known as 3α-hydroxy-3β-methyl-5α-pregnan-20-one, is the 3β-methylated, synthetic analog of the endogenous progesterone metabolite, 3α-hydroxy-5α-pregnan-20-one (3α,5α-P, Allopregnanolone). It is a member of a novel class of neuroactive steroids, which act as positive allosteric modulators of the γ-aminobutyric ($GABA_A$) receptor complex in the central nervous system through interaction with a unique recognition site that is distinct from the benzodiazepine and barbiturate binding sites (Carter et al., 1997). Ganaxolone has been shown to exhibit potent anticonvulsant, anti-anxiety and anti-migraine activity in preclinical models. Ganaxolone has also been shown to extend the life of mice with a lysosomal lipid storage disease that is due to disruption of the mouse homolog of the NPC1 gene, a loci linked to Niemann Pick C in humans. In addition, ganaxolone has been used clinically in adults for the treatment of refractory complex partial seizures and children with refractory infantile spasms and other types of epilepsy. Appropriate ganaxolone formulations also have the potential to treat sleep related disorders.

Ganaxolone is different from other neurosteroids in that the alcohol in the 3 position is blocked from oxidation to the ketone. The 3-keto functionality imparts meaningful steroidal activity, so ganaxolone is distinct from the endogenous neurosteroid (3α, 5α-P) which can be metabolized in vivo to a steroid active compound. Thus, ganaxolone not a steroid and does not have to be handled with the same care and protection as a steroid during its manufacturing and packaging.

It has been very difficult to formulate therapeutically effective dosage forms specific for neurosteroids such as ganaxolone. Ganaxolone is a poorly soluble drug that does not provide good blood levels upon oral administration. Previous dosage forms of ganaxolone have also shown particularly large exposure differences in fed and fasted subjects. Based upon this difficulty, there exists a need in the art for improved ganaxolone formulations and dosage forms. Herein are described solid dosage ganaxolone formulations which address this need and which provide improved pharmacokinetic properties which maintain efficacy while reducing side effects and enhancing subject compliance.

All references discussed herein are incorporated by reference in their entireties for all purposes.

SUMMARY OF THE INVENTION

Described herein are compositions, pharmaceutical compositions, methods for treating, methods for formulating, methods for producing, methods for manufacturing, treatment strategies, pharmacokinetic strategies using ganaxolone.

In one aspect the invention provides a ganaxolone solid oral dosage form comprising at least 200 mg ganaxolone and having a total weight of less than 800 mg.

A ganaxolone formulation comprised of ganaxolone containing particles combined with a small molecule complexing agent providing added stability and superior physical properties such as freeze/thaw stability, heat stability and particle size stability. The types of complexing agents are not anticipated to provide such benefit and are small molecules not containing a sulfonic acid or sulfonate moiety bound to less than 2 saturated carbon atoms.

A ganaxolone formulation to which an ionic dispersion modulator has been added to redisperse ganaxolone containing particles from a solid dosage form without substantial agglomeration.

The invention also provides a pulsatile release ganaxolone oral dosage form, comprising: (a) a first dosage unit comprising a first ganaxolone dose that is released substantially immediately following oral administration of the dosage form to a patient; (b) a second dosage unit comprising a second ganaxolone dose that is released approximately 3 to 7 hours following administration of the dosage form to a patient.

Methods of making ganaxolone solid dosage forms including pulsatile release ganaxolone oral dosage forms are included herein.

The inventors have prepared stable submicron ganaxolone particles with particularly advantageous pharmaceutical properties. Stable ganaxolone particles described herein comprise a complex of ganaxolone and a complexing agent. Additional factors that affect stability and particle size are described herein.

In one aspect are compositions comprising ganaxolone in which the ganaxolone has at least one of the following properties: (a) greater than 90% of the ganaxolone by weight is in the form of submicron particles; (b) at least about 20% of the ganaxolone by weight is in the form of an amorphous powder; (c) at least about 50% of the ganaxolone by weight is in the form of a crystalline powder of a single polymorph; (d) at least about 50% of the ganaxolone is in the form of a semi-crystalline powder; (e) the ganaxolone is in the form of irregular-shaped particles; (f) the ganaxolone is in the form of non-uniform shaped particles; (g) at least about 80% of the ganaxolone has the same general shape while having a distribution of particle sizes; (h) the ganaxolone is in the form of particles having a Gaussian size distribution; (i) the ganaxolone is in the form of particles having a non-Gaussian particle size distribution; (j) the ganaxolone is in the form of particles wherein the particle size distribution is the sum of two Gaussian particle size distributions; (k) the ganaxolone is in the form of particles having a multi-modal particle size distribution; (l) the ganaxolone is in the form of particles having a particle size distribution with a single mode; (m) the ganaxolone is in the form of particles wherein at least about 50% of the particles by weight have an effective particle size less than 500 nm; (n) the ganaxolone is in the form of particles wherein at least about 60% (or at least about 70%, at least about 80%, at least about 90%) of the particles by weight have an effective particle size less than 1000 nm; (o) the ganaxolone is in the form of particles, wherein the particle size distribution is described by a three-slice model in which a certain percentage has an effective particle size by weight between about 10 nm and about 300 nm, a certain percentage has an effective particle size by weight between about 300 nm and about 600 nm, and a certain percentage has an effective particle size by weight above 600 nm, and further wherein the three-slice model is identified as x %/y %/z %, respectively (e.g., 40%/30%/30%); (p) the ganaxolone has a three-slice distribution selected from the group 40%/30%/30%, 50%/30%/20%, 60%/30%/10%, 40%/40%/20%, 50%/40%/10%, 70%/20%/10%, 50%/45%/5%, 70%/25%/5%, 60%/35%/5%, 80%/15%/5%, 70%/30%/0%, 60%/40%/0%, 90%/10%/0%, and 100%/0%/0%; (q) the ganaxolone is in the form of particles, wherein standard deviation of the particle size distribution divided by the volume-weighted mean diameter is less than about 30%, less than about 25%, less than about 20%, less than about 15%, or less than about 10%; (r) the ganaxolone is not in the form of particles; (s) the ganaxolone is in the form of a particle coated with another material; (t) the ganaxolone coats at least a portion of another material; (u) the ganaxolone is microencapsulated in another material; and (v) the ganaxolone is in the form of a particle, wherein the particle size distribution is determined by a laser-light scattering method. In alternative embodiments, the ganaxolone in the composition has at least two of the aforementioned properties; at least about three of the aforementioned properties; at least about four of the aforementioned properties; or at least five of the aforementioned properties.

In another aspect are pharmaceutical formulations comprising ganaxolone, wherein the formulation has at least one of the following characteristics (a) the ganaxolone is selected from one of the aforementioned compositions comprising ganaxolone; (b) the formulation is suitable for administration to a mammal; (c) the ganaxolone is suitable for administration to a human; (d) the ganaxolone is suitable for administration to a human patient having a central-nervous system disease or disorder; (e) the formulation is suitable for administration to a human less than 2 years old; (f) the formulation is suitable for administration to a human between the ages of 2 and 16 years old; (g) the formulation is suitable for administration to an adult; (h) the formulation is suitable for administration to a pre-pubescent human; (i) the formulation is suitable for a post-pubescent human; (j) the formulation is suitable for administration to a human older than about 65 years old; (k) the formulation contains pharmaceutically acceptable excipients; (l) the formulation is suitable for administration to a patient having or expecting an epileptic seizure; (m) the formulation is in the form of a pharmaceutically-acceptable solid dosage form; (n) the formulation is in the form of a pharmaceutically-acceptable non-solid dosage form; (o) the formulation is in the form of a pharmaceutically-acceptable suspension; (p) the formulation further comprises water; (q) the formulation further comprises a pharmaceutically-acceptable viscosity-enhancing agent; (r) the formulation further comprises a dispersing agent; (s) the formulation further comprises a pharmaceutically-acceptable wetting agent; (t) the formulation further comprises a sweetener; (u) the formulation further comprises at least one preservative; (v) the formulation is suitable for administration to a patient via a route selected from oral, intranasal, intravenous, subcutaneous, intramuscular, buccal, and transdermal; (w) the formulation is in the form of a pharmaceutically-acceptable solid oral dosage form; (x) the formulation further comprises a pH-sensitive coating; Also add the formulation comprises a pH insensitive coating (y) the formulation is formulated for pulsatile release; (z) the formulation further comprises a preservative; (aa) the formulation comprises a pH independent coating; (ab) the formulation is formulated via the spray-layering onto a sphere or bead; (ac) the formulation comprises an inhibitor of ganaxolone crystallization; (ad) the formulation is in the form of a microencapsulated drug; (ae) the formulation is in the form of an aqueous dispersion wherein the concentration of ganaxolone is between about 25 to 50 mg/ml of solution; (af) the formulation can be resuspended to a homogenous suspension by shaking; (ag) the formulation comprises ganaxolone on an excipient bead; (ah) the formulation has an amount of ganaxolone of between about 20% to about 40% by weight; The formulation has an amount of ganaxolone about 40% to 65% by weight (ai) the formulation is in the form of a pharmaceutically-acceptable tablet or capsule; (aj) the formulation is in the form of a solid dispersion; (ak) the formulation includes ganaxolone available for immediate release in a patient and ganaxolone in the form of an intermediate release in a patient; The formulation includes Ganaxolone available for immediate release in a patient; (al) the formulation has an enteric coating; (am) the formulation is formulated for releasing greater than about 70%, about 80%, or about 90% of the ganaxolone dosed (by weight) in the stomach and small intestine of a patient; (an) the formulation is formulated so that about 70%, about 80%, or about 90% of the ganaxolone particles by weight dosed are absorbed within about 6 to about 7 hours after administration (ao) the formulation is produced by a method comprising a milling step; (ap) the formulation is produced by a method comprising a grinding step; (aq) the formulation is produced by a method comprising a spray drying step; (ar) the formulation is produced by a method comprising a super-critical fluid; (as) the formulation is produced by a method comprising a crystallization step; (at) the formulation is produced by a method comprising a crushing step; (au) the formulation is produced by a method comprising a communition step; (av) the formulation is produced by a method comprising a rapid expansion of supercritical fluids step; (aw) the formulation is produced by a method comprising a ultrasonication step; (ax) the formulation is produced by a method comprising a precipitation step; (ay) the formulation is produced by a method comprising a fluidized bed process; (az) the formulation is produced by a method comprising a Wurster column; (ba) the formulation is produced by a method comprising a coating step; (bb) the formulation is produced by a method comprising a supercritical fluid fracture step; (bc) the formulation is produced by a method comprising a microfluidizer; (bd) the formulation is produced by a method comprising a high pressure homogenization step; or (be) the formulation is formed by a method comprising a hot melt step. In alternative embodiments, the formulation has at least two of the aforementioned properties; at least about three of the aforementioned properties; at least about four of the aforementioned properties; at least five of the aforementioned properties; or at least six of the aforementioned properties.

In another aspect are methods for treating a disease or disorder in a patient comprising administering a pharmaceutical formulation comprising ganaxolone, wherein the method includes at least one of the following steps or characteristics: (a) the patient is administered at least one of the aforementioned ganaxolone formulations; (b) the disease or disorder is a central nervous system disease or disorder; (c) the disease or disorder is epilepsy; (d) the disease or disorder is a GABA-ergic related disease or disorder; (e) the disease or disorder is a neurosteroid disease or disorder; (f) the ganaxolone is administered to induce sedation; (g) the ganaxolone is administered as an anti-convulsant agent; (h) the ganaxolone is administered as a hypnotic agent; (i) the ganaxolone is administered in a form that maintains plasma levels of about 50 ng/ml at steady state in the patient ($C_{min}$); (j) the ganaxolone is administered in a form that maintains plasma levels of about 25 ng/ml at steady state in the patient ($C_{min}$); (k) the ganaxolone is administered in a form that maintains plasma levels of about 100 ng/ml at steady state in the patient ($C_{min}$); (l) the $C_{max}/C_{min}$ of ganaxolone in plasma of the patient at steady state is less than about 2.5, less than about 2.0, or less than about 1.5; (m) the $AUC_{fed}/AUC_{fasted}$ of ganaxolone in plasma of the patient at steady state is less than about 3.0, 2.0, less than about 1.8, or less than about 1.5; (n) the ganaxolone is administered as an oral suspension to infants about every 6 hours, about every 8 hours, about every 12 hours, as needed; (o) the ganaxolone is administered as an oral suspension to infants to maintain a plasma level of ganaxolone between about 10 to 50 ng/ml of plasma ($C_{min}$) over an 8 hour, over a 12 hour, or over a 24 hour period; (p) the ganaxolone is administered with a rapid release component that achieves a $T_{max}$ between about 0.5 and 2 hours; (q) the ganaxolone is administered with an extended release component that creates a second release profile at the concentration of the initial level at $T_{max}$, that achieves about 80% of the level at $T_{max}$, that achieves about 70% of the level at $T_{max}$, that achieves about 60% of the level at $T_{max}$, or that achieves about 50% of the level at $T_{max}$. In preferred embodiments, the ganaxolone levels is maintained such that the plasma level is less than about 50 ng/ml before the next dose, which can be administered, for example, at 4 hour, 6 hour, 8 hour, 12 hour or 24 hour intervals; (r) the ganaxolone is administered with a pH dependent release component that produces a second drug absorption peak that is about 80% of the level at $T_{max}$, that is about 70% of the level at the level at $T_{max}$, that is about 60% the level at $T_{max}$, or that is about 50% of the level at $T_{max}$ and the ganaxolone level is maintained such that the plasma level is less than about 50 ng/ml before the next dose, which can be administered, for example, at 4 hour, 6 hour, 8 hour, 12 hour or 24 hour intervals; (s) the ganaxolone is administered twice a day; (t) the ganaxolone reduces the incidence of seizures in patients; (u) the ganaxolone is administered in a form with increased kinetic dissolution; (v) the ganaxolone is administered in a form and dose that provides absorption (>70% of the weight) within about 4 to 6 hours after administration; (w) the ganaxolone is administered with at least one other anti-epileptic agent; (x) the ganaxolone is administered with at least one other anti-convulsant; (y) the ganaxolone is administered with an anti-anxiety agent; (z) the ganaxolone is used to treat infantile spasms; (aa) the ganaxolone is used to treat status epilepticus; (ab) the ganaxolone is used to treat partial seizures; (ac) the ganaxolone is used to treat a metabolic disorder; or (ad) the ganaxolone is used to treat catamenial epilepsy. In alternative embodiments, the method has at least two of the aforementioned steps or characteristics; at least about three of the aforementioned steps or characteristics; at least about four of the aforementioned steps or characteristics; at least five of the aforementioned steps or characteristics; or at least six of the aforementioned steps or characteristics.

In certain embodiments, the present invention is directed to stable ganaxolone particles utilizing a complexing agent.

In certain embodiments, the present invention is directed to pharmaceutical compositions containing stable ganaxolone particles comprising a ganaxolone complex exhibiting a ratio of D50 after storage in SGF or SIF at 36 to 38° C. for 1-3 hours to D50 prior to storage of less than about 3:1.

In further embodiments, the invention is directed to a method of milling pharmaceutical products including a pharmaceutically active agent (e.g., ganaxolone), optionally, a suitable amount of simethicone, milling beads and optional pharmaceutically acceptable excipients into a mill; and milling the mixture for a suitable time to obtain submicron particles.

In still further embodiments, the invention is directed to a pharmaceutical composition comprising particles comprising ganaxolone thereof, and simethicone, in an amount, e.g., from about 0.0001% to about 0.1%, based on the total weight of the composition.

Another aspect of the invention is directed to a pharmaceutical composition comprising ganaxolone particles thereof and a vinyl polymer, the particles having a D50 of less than about 500 nm, wherein the $C_{max}$ and $AUC_{(0-\tau)}$ after administration of the composition are decreased as compared to the composition without the vinyl polymer.

In other embodiments, the invention is directed to a pharmaceutical composition comprising particles comprising ganaxolone, the composition providing an increased $AUC_{(0-\tau)}$ in the fasted state.

In further embodiments, the invention is directed to a pharmaceutical composition comprising particles comprising ganaxolone, the composition providing an increased $C_{max}$ in the fasted state.

In another aspect, the invention is directed to a pharmaceutical composition comprising particles comprising ganaxolone, the composition providing a mean blood plasma $AUC_{(0-24)}$ from about 100 to about 300 ng*h/mL after 200 to about 500 mg of ganaxolone is administered to adult subjects in the fasted state.

In still another aspect, the invention is directed to a pharmaceutical composition comprising particles comprising ganaxolone, the composition providing a mean blood plasma $C_{max}$ from about 20 to about 85 ng/mL after 200 to 500 mg of ganaxolone is administered to adult subjects in the fasted state.

In yet another aspect, the invention is directed to a pharmaceutical composition comprising particles comprising ganaxolone, the composition providing a mean blood plasma $AUC_{(0-24)}$ from about 300 to about 1200 ng*h/mL after 200 to about 500 mg of ganaxolone is administered to adult subjects in the fed state.

In a further aspect, the invention is directed to a pharmaceutical composition comprising particles comprising ganaxolone, the composition providing a mean blood plasma $C_{max}$ from about 60 to about 350 ng/mL after 200 to 500 mg of ganaxolone is administered to adult subjects in the fed state.

In another embodiment, the invention is directed to pharmaceutical particles comprising an active agent (e.g., ganaxolone); the particles milled for a sufficient time for the particles to provide a ratio of D50 four weeks after milling to D50 at the end of milling of 1.5:1 or less.

In certain embodiments, the invention is directed to a composition comprising particles comprising ganaxolone, wherein the volume weighted median diameter (D50) of the particles is from about 50 nm to about 500 nm. The composition can have at least one excipient selected from the group consisting of a hydrophilic polymer, a wetting agent, a complexing agent, an ionic dispersion modulator, a water soluble spacer, and a mixture thereof.

In certain embodiments, the invention is directed to a composition comprising particles comprising ganaxolone; and an effective amount of a complexing agent to stabilize the particle growth after an initial particle growth and endpoint is reached, wherein the volume weighted median diameter (D50) of the particles before the initial growth is from about 50 to about 200 nm and the D50 after the endpoint is reached is from about 100 nm to about 350 nm.

In certain embodiments, the invention is directed to a composition comprising particles comprising ganaxolone; and an effective amount of an ionic dispersion modulator to reduce agglomeration of the particles, wherein the volume weighted median diameter (D50) of the particles is from about 50 nm to about 350 nm.

In certain embodiments, the invention is directed to a composition comprising particles comprising ganaxolone; and a complexing agent in an amount of from about 0.1% to about 5%, w/w, based on the weight of the composition, wherein the volume weighted median (D50) of the particles is from about 50 nm to about 350 nm.

In certain embodiments, the invention is directed to a composition comprising particles comprising ganaxolone; and an ionic dispersion modulator in an amount of from about 1% to about 50%, w/w, based on the weight of the composition, wherein the volume weighted median diameter (D50) of the particles is from about 50 nm to about 350 nm.

In other embodiments, the invention is directed to a composition comprising particles comprising ganaxolone; a hydrophilic polymer; and a wetting agent, wherein the volume weighted median diameter (D50) of the particles is from about 50 nm to about 500 nm.

In further embodiments, the invention is directed to a composition comprising particles comprising ganaxolone; a hydrophilic polymer; a wetting agent; and a complexing agent, wherein the volume weighted median diameter (D50) of the particles is from about 50 nm to about 500 nm.

In still other embodiments, the invention is directed to a composition comprising particles comprising ganaxolone; a hydrophilic polymer; a wetting agent; a complexing agent; and an ionic dispersion modulator.

In certain embodiments, the invention is directed to a composition comprising particles comprising ganaxolone in an amount from about 10% to about 80%, w/w, based on the total weight of the composition; a hydrophilic polymer in an amount from about 3% to about 50%, w/w, based on the weight of the composition; a wetting agent in an amount from about 0.05% to about 2%, w/w, based on the weight of the composition; a complexing agent in an amount from about 0.1% to about 5%, w/w, based on the weight of the composition; and an ionic dispersion modulator in an amount from about 1% to about 50%, w/w, based on the weight of the composition.

In certain embodiments, the invention is directed to a solid formulation (e.g., a powder, immediate release dosage form, or controlled release dosage form) comprising stable ganaxolone particles and at least one pharmaceutically acceptable excipient, the stable ganaxolone particles exhibiting an increase in volume weighted median diameter (D50) of from 0% to not more than about 200%, not more than about %150, not more than about %100, or not more than about %50, when the formulation is dispersed in simulated gastric fluid (SGF) or simulated intestinal fluid (SIF) at a concentration of 0.5 to 1 mg ganaxolone/mL (in any suitable volume, e.g., 15 mL to 1000 mL) and placed in a heated bath at 36° to 38° C. for 1 hour, as compared to the D50 of the ganaxolone particles when the formulation is dispersed in distilled water under the same conditions, wherein the volume weighted median diameter (D50) of the ganaxolone particles dispersed in distilled water is from about 50 nm to about 1000 nm, from about 100 nm to about 500 nm, or from about 100 nm to about 350 nm. The solid formulation can be, for example, a powder, a tablet, a capsule, etc.

In certain aspects, the solid formulation is in the form of a tablet or capsule containing the stable ganaxolone particles and at least one excipient, the stable ganaxolone particles exhibiting an increase in volume weighted median diameter (D50) of from 0% to not more than about 200%, not more than about %150, not more than about %100, or not more than about %50, when the tablets or capsules are dispersed in SGF or SIF (in any suitable volume, e.g., 15 mL to 1000 mL) at a concentration of 0.5 to 1 mg ganaxolone/mL at 36° to 38° C. using a Type II dissolution apparatus and a stirring rate of 75 RPM for 1 hour, as compared to the D50 of the ganaxolone particles when the tablets or capsules are dispersed in distilled water under the same conditions, wherein the volume weighted median diameter (D50) of the ganaxolone particles when the tablets or capsules are dispersed in distilled water is from about 50 nm to about 1000 nm, from about 100 nm to about 500 nm, or from about 100 nm to about 350 nm.

In other aspects, the invention is directed to a solid formulation (e.g., a powder, immediate release dosage form, or controlled release dosage form) comprising stable ganaxolone particles and at least one pharmaceutically acceptable excipient, the stable ganaxolone particles exhibiting a volume weighted median diameter (D50) of less than about 750 nm when the formulation is dispersed in simulated gastric fluid (SGF) for one hour followed by simulated intestinal fluid (SIF) for three additional hours, at a concentration of 0.5 to 1 mg ganaxolone/mL (in any suitable volume, e.g., 15 mL to 1000 mL) at a temperature of 36° to 38° C.

In still other aspects, the solid formulation is a tablet or capsule containing the stable ganaxolone particles and at least one excipient, the stable ganaxolone particles exhibiting a volume weighted median diameter (D50) of less than about 750 nm when the tablets or capsules are dispersed in simulated gastric fluid (SGF) for one hour followed by simulated intestinal fluid (SIF) for three additional hours, at a concentration of 0.5 to 1 mg ganaxolone/mL (in any suitable volume, e.g., 15 mL to 1000 mL) at a temperature of 36° to 38° C. using a Type II dissolution apparatus and a stirring rate of 75 RPM.

In certain embodiments, the stable particles are prepared by contacting ganaxolone particles with excipient such that the size of the particles exhibits an increase in volume weighted median diameter of from about 20% to about 300% and an endpoint is reached such that the particles are stable. The endpoint can be, e.g., from about 1 to about 20 days.

In other aspects, the invention is directed to an oral solid dosage form comprising (i) a controlled release component comprising a first portion of particles comprising ganaxolone; and a controlled release material, and (ii) an immediate release component comprising a second portion of particles comprising ganaxolone, the first and second portion of ganaxolone particles having a volume weighted median diameter (D50) of from about 50 nm to about 1000 nm, from about 100 nm to about 450 nm, or from about 100 nm to about 350 nm. The ratio of ganaxolone in controlled release to immediate release can be, e.g., from about 4:1 to about 1:4, from about 3:2 to about 2:3, or about 1:1. The controlled release component can be in any form, including but not limited to (i) a plurality of pharmaceutically acceptable beads coated with the first portion of ganaxolone particles and overcoated with the controlled release material (optionally a film coat comprising a material such as hydroxypropylmethylcellulose or polyvinyl alcohol can be included on the beads prior to coating with the ganaxolone particles), (ii) a plurality of matrices comprising the first portion of ganaxolone particles dispersed in the controlled release material, (iii) a tablet comprising the first portion of ganaxolone particles dispersed in the controlled release material, or (iv) a granulation comprising the first portion of ganaxolone particles and the controlled release material. The immediate release component can be in any form, including bit not limited to (i) plurality of pharmaceutically acceptable beads coated with the second portion of ganaxolone particles, (ii) a plurality of matrices comprising the second portion of ganaxolone particles dispersed in an excipient, (iii) a tablet comprising the second portion of ganaxolone particles dispersed in excipient, or (v) a granulation comprising the second portion of ganaxolone particles and excipient. Alternatively, the immediate release component can be included in the dosage form in powder form.

In certain embodiments, the controlled release component and the immediate release component are contained in a capsule.

In other embodiments, the controlled release component is a tablet and the immediate release component is coated onto the tablet.

In further embodiments, the controlled release component and the immediate release component are in a bi-layer tablet.

In still other embodiments, the controlled release component comprises a plurality of pharmaceutically acceptable beads coated with the first portion of ganaxolone particles and overcoated with the controlled release material and the immediate release component comprises a plurality of pharmaceutically acceptable beads coated with the second portion of ganaxolone particles, the controlled release component and immediate release component contained in a capsule.

In another aspect, the controlled release component comprises a plurality of pharmaceutically acceptable beads coated with the first portion of ganaxolone particles and overcoated with the controlled release material and the immediate release component comprises a tablet comprising the second portion of ganaxolone particles dispersed in an excipient, the controlled release component and immediate release component contained in a capsule.

In still another embodiments, controlled release component comprises a plurality of pharmaceutically acceptable beads coated with the first portion of ganaxolone particles and overcoated with the controlled release material and the immediate release component comprises a granulation comprising the second portion of ganaxolone particles and an excipient, the controlled release component and immediate release component contained in a capsule.

In another embodiment, the controlled release component comprises a plurality of pharmaceutically acceptable beads coated with the first portion of ganaxolone particles and overcoated with the controlled release material, and the immediate release component comprises a granulation comprising the second portion of ganaxolone particles and an excipient, the controlled release component dispersed in the immediate release component in the form of a compressed tablet.

In further embodiments, the controlled release component comprises a compressed tablet and the immediate release component is compression coated over the controlled release tablet.

In certain embodiments, the dosage forms of the present invention provide pulsatile release of two or more doses of ganaxolone. The dosage form can provide an immediate release dose after administration and at least one additional dose at a time after administration selected from the group consisting of 3-8 hours, 6-10 hours, 10-14 hours, 14-18 hours, 16-20 hours and 22-24 hours.

In certain embodiments, the invention is directed to an oral solid dosage form comprising ganaxolone particles and a controlled release material, the ganaxolone particles having a volume weighted median diameter (D50) of from about 50 nm to about 1000 nm, the dosage form providing a controlled release of the ganaxolone to provide a therapeutic effect for about 8 to about 24 hours after administration.

In other embodiments, the invention is directed to an oral solid dosage form comprising particles comprising ganaxolone; and a pH dependent polymer, the ganaxolone particles having a volume weighted median diameter (D50) from about 50 nm to about 1000 nm, the dosage form providing a delayed release of the ganaxolone for a time period from about 2 to about 12 hours after administration.

In certain aspects, the invention is directed to a stable solid dose formulation comprising a plurality of substrates coated with particles comprising ganaxolone; and at least one pharmaceutically acceptable excipient, the particles having a volume weighted median diameter (D50) from about 50 nm to about 1000 nm, from about 100 nm to about 450 nm, or from about 100 nm to about 350 nm, the coated substrates exhibiting an increase in volume weighted median diameter (D50) of 0 to less than 200% after being dispersed in SGF or SIF in a concentration of 0.5-1 mg ganaxolone/ml and placed in a heated bath at 36° to 38° C. without stirring for 1 hour as compared to the D50 under the same conditions after being dispersed in distilled water. The volume weighted median diameter (D50) of the coated beads prior to dispersion can be, e.g., from about 0.1 mm to about 5.0 mm.

In other aspects, the invention is directed to an immediate release oral solid dosage form comprising ganaxolone particles; and at least one pharmaceutically acceptable excipient, the ganaxolone particles having a volume weighted median diameter (D50) of from about 50 nm to about 1000 nm.

In certain embodiments, the invention is directed to a pharmaceutical dosage form (e.g., a liquid or solid dosage form) comprising particles comprising ganaxolone; and at least one pharmaceutically acceptable excipient, the particles having a volume weighted median diameter (D50) from about 50 nm to about 1000 nm, the dosage form providing a ratio of mean blood plasma fed $AUC_{(0-\tau)}$ to fasted $AUC_{(0-\tau)}$ from about 1:1 to about 4:1, from about 1.3:1 to about 4:1, or from about 1:1 to about 3:1.

In other embodiments, the invention is directed to a pharmaceutical dosage form (e.g., a liquid or solid dosage form) comprising particles comprising ganaxolone; and at least one pharmaceutically acceptable excipient, the particles having a volume weighted median diameter (D50) from about 50 nm to about 1000 nm, the dosage form providing a ratio of mean blood plasma fed Cmax to fasted Cmax from about 1.5:1 to about 7:1, from about 2.5:1 to about 7:1, or from about 1.5:1 to about 4:1.

In other embodiments, the invention is directed to a pharmaceutical dosage form comprising particles comprising ganaxolone; and at least one pharmaceutically acceptable excipient, the particles having a volume weighted median diameter (D50) from about 50 nm to about 1000 nm, the dosage form providing a mean blood plasma AUC 0-24 hours from about 100 to about 375 ng*h/ml when a dose of 200 mg to 500 mg of the ganaxolone is orally administered to adult subjects in the fasted state.

In further embodiments, the invention is directed to a pharmaceutical dosage form comprising particles comprising ganaxolone; and at least one pharmaceutically acceptable excipient, the particles having a volume weighted median diameter (D50) from about 50 nm to about 1000 nm, the dosage form providing a mean blood plasma Cmax from about 25 to about 70 ng/ml when a dose of 200 mg to 500 mg of the ganaxolone is orally administered to adult subjects in the fasted state.

In yet another embodiment, the invention is directed to a pharmaceutical dosage form comprising particles comprising ganaxolone; and at least one pharmaceutically acceptable excipient, the particles having a volume weighted median diameter (D50) from about 50 nm to about 1000 nm, the dosage form providing a mean blood plasma AUC (0-48) hours from about 400 to about 1200 ng*h/ml when a dose of 200 mg to 500 mg of the ganaxolone is orally administered to adult subjects in the fed state.

In further embodiments, the invention is directed to a pharmaceutical dosage form comprising particles comprising ganaxolone; and at least one pharmaceutically acceptable excipient, the particles having a volume weighted median diameter (D50) from about 50 nm to about 1000 nm, the dosage form providing a mean blood plasma Cmax from about 60 to about 250 ng/ml when a dose of 200 mg to 500 mg of the ganaxolone is orally administered to adult subjects in the fed state.

In other aspects, the invention is directed to a pharmaceutical dosage form comprising particles comprising ganaxolone; and at least one pharmaceutically acceptable excipient, the particles having a volume weighted median of from about 50 nm to about 1000 nm, the dosage form providing a mean blood plasma Cmax/Cmin ratio of not greater than about 4 to 1 at steady state with a dose of 200 to 500 mg ganaxolone to adult subjects in the fed or fasted state.

In still other aspects, the invention is directed to a liquid pharmaceutical dosage form comprising particles comprising ganaxolone; and at least one pharmaceutically acceptable excipient, the particles having a volume weighted median of from about 50 nm to about 1000 nm, the dosage form providing a mean blood plasma Cmin value of about 10-40 ng/ml in infants (greater than 4 months old but less than 2 years old) at a ganaxolone dose of about 10 mg/kg at steady state.

In still other aspects, the invention is directed to a liquid pharmaceutical oral suspension comprising ganaxolone, the suspension providing a mean blood plasma Cmax of about 30 to 45 ng/mL and a mean blood plasma AUC (0-24) of about 160 to about 210 ng*h/mL, based on a dose of 200 mg ganaxolone to subjects in the fasted state, or a mean blood plasma Cmax of about 37 ng/mL and a mean blood plasma AUC (0-24) of about 185 ng*h/mL, based on a dose of 200 mg ganaxolone to subjects in the fasted state.

In certain embodiments, the invention is directed to an oral liquid dosage form comprising stable ganaxolone particles and at least one pharmaceutically acceptable excipient, the particles suspended in a pharmaceutically acceptable liquid vehicle, wherein the volume weighted median diameter (D50) of the stable ganaxolone particles does not change by more than about 15% after 10 days storage at room temperature, by more than about 12% after 10 days storage at room temperature, by more than about 10% after 10 days storage at room temperature, by more than about 8% after 10 days storage at room temperature, by more than about 15% after 20 days of storage at room temperature, by more than about 15% after 40 days of storage at room temperature, by more than about 15% after 60 days of storage at room temperature, or by more than about 15% after 80 days of storage at room temperature. In certain aspects, the volume weighted median diameter (D50) of the stable ganaxolone particles prior to storage is from about 100 nm to about 450 nm, or from about 100 nm to about 350 nm.

In certain embodiments, the invention is directed to an oral liquid dosage form wherein the volume weighted median diameter (D50) of the stable ganaxolone particles does not change by more than about 15% when placed in a glass vial and heated in a 100° C. oil bath for 20 minutes, does not change by more than about 15% when placed in a glass vial and heated in a 100° C. oil bath for 4 hours, does not change by more than about 10% when placed in a glass vial and heated in a 100° C. oil bath for 20 minutes, does not change by more than about 5% when placed in a glass vial and heated in a 100° C. oil bath for 20 minutes, or does not change by more than about 3% when placed in a glass vial and heated in a 100° C. oil bath for 20 minutes.

In still further embodiments, the invention is directed to an oral liquid dosage form the volume weighted median diameter (D50) of the stable ganaxolone particles does not change by more than about 25% when placed in a HDPE container and frozen and thawed three or more times with the time frozen for each cycle being at least 12 hours. The frozen temperature can be any suitable freezing temperature, e.g., from about −80° C. to about −20° C. the invention is also directed to the liquid dosage forms in frozen form.

In certain embodiments, the oral liquid dosage form is prepared by contacting ganaxolone particles with the excipient, wherein the size of the particles exhibits an increase in volume weighted median diameter (D50) of from about 20% to about 300% and reaching an endpoint such that the particles are stable.

In other aspects, the invention is directed to pharmaceutical particles comprising ganaxolone or a pharmaceutically acceptable salt thereof, the particles being stable such that the volume weighted median diameter (D50) of the particles does not increase by more than about 50% after 28 days storage at room temperature and ambient conditions, the volume weighted median diameter (D50) of the particles prior to storage being from about 50 nm to about 1000 nm; the particles milled for a sufficient time to achieve the stability. In other aspects, the volume weighted median diameter (D50) of the particles does not change by more than about 25% after 28 days storage at room temperature and ambient conditions, does not change by more than about 15% after 28 days storage at room temperature and ambient conditions, does not change by more than about 10% after 28 days storage at room temperature and ambient conditions, or does not change by more than about 50% after 40 days storage at room temperature and ambient conditions.

The present invention is also directed to a method of stabilizing the particle growth of pharmaceutical particles comprising milling ganaxolone to a volume weighted median diameter (D50) from about 50 nm to about 1000 nm and for a sufficient time such that that the volume weighted median diameter (D50) of the particles does not change by more than about 50% after 28 days storage at room temperature and ambient conditions, does not change by more than about 25% after 28 days storage at room temperature and ambient conditions, does not change by more than about 15% after 28 days storage at room temperature and ambient conditions, or does not change by more than about 10% after 28 days storage at room temperature and ambient conditions.

In still further embodiments, the present invention is directed to a pharmaceutical composition comprising particles comprising (i) ganaxolone or a pharmaceutically acceptable salt thereof, and (ii) a trace amount of simethicone, the particles having a volume weighted median diameter (D50) of from about 50 nm to about 1000 nm. In certain embodiments, the simethicone is in an amount from about 0.001% to about 1%, or 0.005% to about 0.02% simethicone, w/w, based on the weight of the particles.

In other embodiments, the invention is directed to a method of milling ganaxolone, comprising incorporating ganaxolone, a suitable amount of simethicone, milling beads and optional pharmaceutically acceptable excipients into a mill; and milling the mixture for a suitable time to obtain nanosized particles. The simethicone can be in the form of an emulsion, e.g., containing from 20% to 50% simethicone. Further, the amount of simethicone present in the milling slurry can be, e.g., from about 0.01% to about 5%, from about 0.02% to about 1%, or about 0.04% to about 0.6%, w/w, based on the weight of the ganaxolone.

The present invention is also directed to a method of stabilizing pharmaceutical particles comprising preparing particles comprising ganaxolone or a pharmaceutically acceptable salt thereof having a volume weighted median diameter (D50) about 50 nm to about 450 nm, contacting the ganaxolone particles with a complexing agent wherein the volume weighted median diameter (D50) of the particles increases from about 20% to about 300%, and reaching an endpoint such that the particles are stable. In further embodiments, the complexed particles are subjected to sonification to decrease the volume weighted median diameter (D50) from about 10% to about 60% prior to reaching the endpoint.

The present invention is also directed to a method of preparing pharmaceutical particles comprising preparing particles comprising ganaxolone or a pharmaceutically acceptable salt thereof having a volume weighted median diameter (D50) of about 50 nm to about 450 nm, and contacting a vinyl polymer with the ganaxolone particles such that the Cmax provided by the particles is reduced from about 25% to 80%.

The present invention is also directed to a method of preparing pharmaceutical particles comprising preparing particles comprising ganaxolone or a pharmaceutically acceptable salt thereof having a volume weighted median diameter (D50) of about 50 nm to about 450 nm, and contacting a vinyl polymer with the ganaxolone particles such that the AUC provided by the particles is reduced from about 25% to 80%.

The present invention is further directed to methods of preparing the compositions disclosed herein, including but not limited to, ganaxolone particles, liquid formulations, and oral solid dosage forms (e.g., immediate release, sustained release, delayed release and pulsatile release).

The present invention is also directed to methods of treating subjects comprising administering to a subject any of the compositions disclosed herein, including, but not limited to, ganaxolone particles, liquid formulations, and oral solid dosage forms (e.g., immediate release, sustained release, delayed release and pulsatile release).

In the above embodiments, the ganaxolone compositions of the present invention, (e.g., liquid or solid) comprise an excipient selected from the group consisting of a hydrophilic polymer, a wetting agent, a complexing agent, an ionic dispersion modulator, a water soluble spacer, and a mixture thereof.

In certain embodiments, the excipient comprises a complexing agent. The complexing agent can be a substance containing a phenol moiety, an aromatic ester moiety or an aromatic acid moiety. Particular complexing agents are selected from the group consisting of parabens, organic acids, carboxylic acids, aromatic acids, aromatic esters, acid salts of amino acids, methyl anthranilate, sodium metabisulphite, ascorbic acid and its derivatives, malic acid, isoascorbic acid, citric acid, tartaric acid, sodium sulphite, sodium bisulphate, tocopherol, water- and fat-soluble derivatives of tocopherol, sulphites, bisulphites and hydrogen sulphites, para-aminobenzoic acid and esters, 2,6-di-t-butyl-alpha-dimethylamino-p-cresol, t-butylhydroquinone, di-t-amylhydroquinone, di-t-butylhydroquinone, butylhydroxytoluene (BHT), butylhydroxyanisole (BHA), pyrocatechol, pyrogallol, propyl/gallate, nordihydroguaiaretic acid, phosphoric acids, sorbic and benzoic acids, esters, ascorbyl palmitate, derivatives and isomeric compounds thereof, pharmaceutically acceptable salts thereof, and mixtures thereof.

In certain embodiments, the excipient comprising a hydrophilic polymer. The hydrophilic polymer can be selected from the group consisting of a cellulosic polymer, a vinyl polymer and mixtures thereof. Particular hydrophilic polymers include cellulosic polymer such as cellulose ethers (e.g., hydroxypropylmethylcellulose.) or a vinyl polymer such as polyvinyl alcohol.

In certain embodiments, the excipient comprises a wetting agent. The wetting agent can be selected from the group consisting of sodium lauryl sulfate, a pharmaceutically acceptable salt of docusate, and mixtures thereof.

In certain embodiments, the excipient comprises an ionic dispersion modulator. The ionic dispersion modulator can be a salt such as an organic or inorganic salt. The inorganic salt can be selected from the group consisting of a magnesium salt, a calcium salt, a lithium salt, a potassium salt, a sodium salt and mixtures thereof and the organic salt can be selected from the group consisting of a citrate salt, a succinate salt, a fumarate salt, a malate salt, maleate salt, a tartrate salt, a glutarate salt, a lactate salt and mixtures thereof.

In certain embodiments, the excipient comprises a water soluble spacer. The water soluble can be a saccharide or an ammonium salt. The saccharide can be selected from the group consisting of fructose, sucrose, glucose, lactose, mannitol and mixtures thereof.

In embodiments directed to solid formulations, the complexing agent can be in an amount from about 0.05% to about 5%, w/w, based on the weight of the solid formulation; the hydrophilic polymer can be in an amount from about 3% to about 50%, w/w, based on the weight of the solid formulation; the cellulose ether can be in an amount from about 3% to about 50%, w/w, based on the weight of the solid formulation; the polyvinyl alcohol van be in an amount from about 0.1% to about 5%, w/w, based on the weight of the solid formulation; the wetting agent can be in an amount from about 0.01% to about 10%, w/w, based on the weight of the solid formulation; the ionic dispersion modulator can be in an amount from about 1% to about 50%, w/w, based on the weight of the solid formulation; and the water soluble spacer can be in an amount from about 2% to about 60%, w/w, based on the weight of the solid formulation. The % weights are not meant to be limiting.

In embodiments directed to ganaxolone coated beads, controlled release material can be coated onto the drug layered bead in an amount, e.g., from about 3% to about 25%, or from about 8% to about 12%, based on the total weight of the component.

In certain solid formulations, the ganaxolone particles are dispersed in a liquid to form a suspension and the suspension is spray coated onto the plurality of substrates, or spray granulated with the plurality of substrates. In further embodiments the ganaxolone particles are dispersed in a liquid to form a suspension and the suspension is spray dried to form a powder which is coated onto the plurality of substrates. The suspension can be, e.g., about 5% to about 35%, or about 15% to about 25% total solids. The ganaxolone concentration in the solids can be, e.g., from about 50% to about 75%.

In embodiments directed to solid dosage forms utilizing substrates, the substrates can be, e.g., inert beads, or can be selected from the group consisting of lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol and mixtures thereof.

In embodiments directed to sustained or delayed dosage forms, the dosage form can be a granulation comprising the ganaxolone particles and the controlled release material, (e.g., hydrophobic polymer or pH dependent material), the granulation compressed into a tablet or filled into a capsule.

In other embodiments directed to sustained or delayed release dosage forms, the dosage form can be a plurality of pharmaceutically acceptable beads coated with the ganaxolone particles and overcoated with the controlled release material, (e.g., hydrophobic polymer or pH dependent material), the overcoated beads compressed into a tablet or filled into a capsule.

In embodiments directed to liquid dosage forms, the liquid dosage form can be include at least one excipient selected from polyvinyl alcohol, sodium lauryl sulfate, methylparaben, propylparaben, sodium benzoate, citric acid, sodium citrate, simethicone, sucralose and flavoring. For example, the liquid dosage form can comprise about 5% ganaxolone, about 1% polyvinyl alcohol, about 0.1% sodium lauryl sulfate, about 0.1% methylparaben, about 0.02% propylparaben, about 0.9% sodium benzoate, about 0.12% citric acid, about 0.06% sodium citrate, about 0.01% simethicone, about 0.02% sucralose, and flavoring. These ingredients and % amounts are not meant to be limiting.

In certain embodiments, the invention is directed to an oral liquid dosage form comprising stable ganaxolone particles, hydroxymethylpropylcellulose, sodium lauryl sulfate, simethicone, sucralose, methylparaben, propylparaben, sodium benzoate, citric acid, sodium citrate, and flavoring, the liquid having a pH of from about 3.8 to about 4.2

In certain embodiments, the invention is directed to an oral liquid dosage form comprising from about 2.5% to about 5% stable ganaxolone particles, from about 2% to about 5% hydroxymethylpropylcellulose, from about 0.1% to about 0.03% sodium lauryl sulfate, from about 0.005% to about 0.02% simethicone, from about 0.01% to about 0.03% sucralose, from about 0.05% to about 0.1% methylparaben, from about 0.01% to about 0.02% propylparaben, from about 0.05% to about 0.1% sodium benzoate, from about 0.1% to about 0.15% citric acid, from about 0.05 to about 0.1% sodium citrate and from about 0.002% to about 0.004% flavoring, the liquid having a pH of about 3.8 to about 4.2, wherein all percentages are weight percent to the total liquid formulation weight.

In certain embodiments, the invention is directed to an oral liquid dosage form comprising stable ganaxolone particles, hydroxymethylpropylcellulose, polyvinyl alcohol, sodium lauryl sulfate, simethicone, sucralose, methylparaben, propylparaben, sodium benzoate, citric acid, sodium citrate and flavoring, the liquid having a pH of about 3.8 to about 4.2, wherein all percentages are weight percent to the total liquid formulation weight.

In certain embodiments, the invention is directed to an oral liquid dosage form comprising from about 2.5% to about 5% stable ganaxolone particles, from about 2% to about 5% hydroxymethylpropylcellulose, about 0.5% to about 1.5% polyvinyl alcohol, from about 0.1% to about 0.03% sodium lauryl sulfate, from about 0.005% to about 0.02% simethicone, from about 0.01% to about 0.03% sucralose, from about 0.05% to about 0.1% methylparaben, from about 0.01% to about 0.02% propylparaben, from about 0.05 to about 0.1% sodium benzoate, from about 0.05% to about 0.15% citric acid, from about 0.05 to about 0.1% sodium citrate and from about 0.002% to about 0.004% flavoring, the liquid having a pH of about 3.8 to about 4.2, wherein all percentages are weight percent to the total liquid formulation weight.

BRIEF DESCRIPTION OF THE DRAWINGS

FIG. 1. Curing of parabens preserved and sodium benzoate preserved ganaxolone particles: particle size growth was partially reversed by 1 min sonication (low power setting) in the early stage of the curing process.

FIG. 2. Curing of parabens preserved and sodium benzoate preserved ganaxolone particles: particles containing parabens were fully cured within 5-7 days while sodium benzoate preserved particles required approximately 3 weeks to become stable.

FIG. 3. Stability plots (D50 vs time) of ganaxolone particles containing no complexing agent: ganaxolone particles without a complexing agent that were milled for less than 2 hours of milling residence time continued to increase gradually in size over a number of months, while the particles milled for more than 2 hours of residence time did not change over six months.

FIG. 4. Progress of a milling run using a DYNO-Mill KDL equipped with four 64 mm polyurethane agitator discs followed by particle size measurement (D50) as a function of residence time.

FIG. 5. Particle Size Distribution (after 1 minute low power sonication) of Re-suspended Solid Dosage Forms Containing Sodium Chloride: With and Without a Complexing Agent (Methylparaben)

DETAILED DESCRIPTION OF THE INVENTION

Reference will now be made in detail to embodiments of the compositions, formulations, and methods disclosed herein. Examples of the embodiments are illustrated in the following Examples section.

Unless defined otherwise, all technical and scientific terms used herein have the same meaning as is commonly understood by one of skill in the art to which the inventions described herein belong. All patents and publications referred to herein are incorporated by reference.

Certain Definitions

As used herein, the terms "comprising," "including,", "containing" and "such as" are used in their open, non-limiting sense.

The term "about" is used synonymously with the term "approximately." As one of ordinary skill in the art would understand, the exact boundary of "about" will depend on the component of the composition. Illustratively, the use of the term "about" indicates that values slightly outside the cited values, i.e., plus or minus 0.1% to 10%, which are also effective and safe. Thus compositions slightly outside the cited ranges are also encompassed by the scope of the present claims.

"Antifoaming agents" reduce foaming during processing which can result in coagulation of aqueous dispersions, bubbles in the finished form, or generally impair processing. Exemplary anti-foaming agents include silicon emulsions or sorbitan sesquioleate.

"Antioxidants" include, e.g., butylated hydroxytoluene (BHT), butylhydroxyanisole (BHA), ascorbic acid, sodium ascorbate, and tocopherol. Combinations of one or more antioxidants can also be used.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel® PH101 and Avicel® PH102); silicified microcrystalline cellulose (ProSolv SMCC®), microcrystalline dextrose; amylose; magnesium aluminum silicate; polysaccharide acids; bentonites; gelatin; polyvinylpyrrolidone/vinyl acetate copolymer; crosspovidone; povidone; starch, such as corn starch, potato starch, wheat starch, rice starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinyl alcohol, polyvinylpyrrolidone (e.g., Povidone® CL, Kollidon® CL, Polyplasdone® XL-10), larch arabogalactan, Veegum® polyethylene glycol, waxes, sodium alginate, and the like. Combinations of one or more binders can also be used.

"Bioavailability" refers to the degree to which a drug becomes available at the site(s) of action after administration. By way of illustration, the bioavailability of a ganaxolone formulation refers to the percentage of the weight of ganaxolone dosed that is delivered into the general circulation of the animal or human being studied. The total exposure ($AUC_{(0-\infty)}$) of a drug when administered intravenously is usually defined as 100% bioavailable (F %). "Oral bioavailability" refers to the extent to which ganaxolone is absorbed into the general circulation when the pharmaceutical composition is taken orally as compared to intravenous injection. The degree and timing in which an active agent becomes available to the target site(s) after administration is determined by many factors, including the dosage form and various properties, e.g., solubility and dissolution rate of the drug.

A "blood serum concentration" or "blood plasma concentration" or "serum or plasma concentration or level", typically measured in mg, µg, or ng of a drug per ml, dl, or 1 of serum or plasma absorbed into the bloodstream after administration. As used herein, measurable plasma concentrations are typically measured in ng/ml or µg/ml. It is understood that the plasma concentration of a ganaxolone may vary significantly between subjects, due to variability with respect to metabolism and/or possible interactions with other therapeutic agents. In accordance with one aspect of the present invention, the blood plasma concentration of ganaxolone may vary from subject to subject. Likewise, values such as measured concentration of the active agent in the plasma at the point of maximum concentration ($C_{max}$) or time to reach maximum plasma concentration ($T_{max}$), or total area under the plasma concentration time curve ($AUC_{(0-\infty)}$) may vary from subject to subject.

"$AUC_{(0-\tau)}$" or "exposure" is the area under the curve of a graph of the concentration of the active agent (typically plasma concentration) vs. time ($\tau$), measured from time 0 to $\tau$. $AUC_{(0-\tau)}$ is also used to define the exposure to the drug over a defined period of time. Due to variability, the amount necessary to constitute "a therapeutically effective amount" of ganaxolone may vary from subject to subject.

"Carrier materials" include any commonly used excipients in pharmaceutics and should be selected on the basis of compatibility with ganaxolone and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may comprise, but are not limited to, acacia, gelatin, colloidal silicon dioxide, calcium glycerophosphate, calcium lactate, maltodextrin, glycerin, magnesium silicate, polyvinylpyrrolidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms* and Drug Delivery Systems, Seventh Ed. (Lippincott Williams & Wilkins 1999).

"Conventional Ganaxolone Formulations," as used herein, refers to ganaxolone formulations previously administered to subjects. Such formulations include ganaxolone formulated with β-cyclodextrin or 2-hydroxypropyl-β-cyclodextrin. As published data is dominated by the use of the ganaxolone/β-cyclodextrin 1:1 complex, this formulation is the preferred standard by which to compare the ganaxolone formulations described herein.

The term "curing" means a sufficient time until an endpoint is reached such that the D50 does not change or substantially change after time in consecutive measurements separated by approx. 72 hours, e.g., by more than the accuracy of the measuring instrument±5%. in 72 hours after the curing period. Preferred curing times are 1-20 days, 2-15 days or 3-10 days.

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as cellulosics, for example, hydroxypropylcelluloses (e.g., HPC, HPC-SL, and HPC-L), hydroxypropylmethylcellulose's (e.g., Pharmacoat 603, HPMC K100, HPMC K4M, HPMC K15M, and HPMC K100M), carboxymethylcellulose sodium, methylcellulose, hydroxyethylcellulose, hydroxypropylcellulose, noncrystalline cellulose, microcrystalline cellulose, silicified microcrystalline cellulose, hydroxypropylmethylcellulose phthalate, and hydroxypropylmethylcellulose acetate stearate (HPMCAS). Other dispersing agents include magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, polysorbate-80, sodium alginate, gums, such as gum tragacanth and gum acacia, guar gum, xanthans, including xanthan gum, sugars, polysorbate-80, sodium alginate, polyethoxylated sorbitan monolaurate, polyethoxylated sorbitan monolaurate, povidone, carbomers, alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

The term "complex" or "ganaxolone complex" indicates an association of molecules and/or a particle including ganaxolone and optionally other molecules which results in better stability of ganaxolone particles or some other desirable effect. In some cases, complexing agents initially increase particle size (D50) before imparting stability or other beneficial attributes to the formulation. In certain embodiments, ganaxolone complexes made by adding complexing agents requires a curing time.

"Complexing agents" are molecules which when added to a small particle composition (D50 of about 75 to about 400 nm) under the appropriate conditions will act as a stabilizing agent. Addition of a complexing agent can also impart additional suspension stability during freeze/thaw cycles and boiling if sterilization is needed. Complexing agents include small compounds under MW. 550, which do not contain a sulfonic acid or sulfonic acid/inorganic salt counterion group at the end of an alkyl chain containing more than one saturated carbon atom bonded to the carbon atom bearing the sulfonic acid moiety. Complexing agents include but are not limited to phenols and phenolic salts, aromatic acids and esters, carboxylic acids and salts and esters thereof, inorganic acids and bases and amino acids and esters and salts thereof. Some examples include but are not limited to phenol, methylparaben, propylparaben, potassium methylparaben, sodium methylparaben, BHT, sorbic acid, ascorbic acid, p-aminobenzoic acid, benzoic acid ascorbic acid, methyl anthranilate, anthranilic acid, picolinic acids and alkyl esters thereof, and sodium benzoate. "Controlled Release" or "Modified Release", consistent with its use herein, means a dosage form for which the drug release characteristics versus time and/or conditions at the site of dissolution are chosen to accomplish therapeutic or convenience objectives not offered by conventional immediate release dosage forms. Controlled release dosage forms include sustained release, prolonged release, pulsatile release and delayed release forms. Controlled release dosage forms can provide therapeutically effective levels of drug for an extended period of time and therefore provide a longer therapeutic period relative to immediate release forms.

"Delayed Release", consistent with its use herein, means a dosage form that releases a drug at any time other than immediately after administration and/or at any other location in the gastrointestinal tract more distal to that which would have been accomplished by an immediate release dosage form. Enteric coated dosage forms are an example of a delayed release dosage form.

"Diluents" increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like. Combinations of one or more diluents can also be used.

The term "disintegrate" is the dispersion of the dosage form when contacted with gastrointestinal fluid or a dispersing agent. "Disintegration agents or disintegrants" facilitate the breakup or disintegration of a formulation. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, microcrystalline cellulose, e.g., Avicel®, Avicel® PH101, Avicel®PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate (Explotab®), bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system "Effective particle size" is interchangeably used with "D50". By "D50", it is meant that 50% of the particles are below and 50% of the particles are above a defined measurement. D50 can be used to describe different parameters (volume, length, number, area . . . etc). "Effective particle size" or D50 as used herein indicates the volume-weighted median diameter as measured by a laser/light scattering method or equivalent, wherein 50% of the particles, by volume, have a smaller diameter, while 50% by volume have a larger diameter. The volume weighted D50 also relates to the percentage of weight of the particle under a certain size. For example a D50 of 500 nm means that 50% of the particulate mass is less than 500 nm in diameter and 50% of the particulate mass is greater than 500 nm in diameter. The effective particle size is measured by conventional particle size measuring techniques well known to those skilled in the art. Such techniques include, for example, sedimentation field flow fractionation, photon correlation spectroscopy, light scattering (e.g., with a Microtrac UPA 150), laser diffraction and disc centrifugation. For the purposes of the compositions, formulations and methods described herein, effective particle size is the volume median diameter as determined using laser/light scattering instruments and methods, e.g. a Horiba LA-910, or Horiba LA-950. Similarly, "D90" is the volume-weighted diameter, wherein 90% of the particles, by volume, have a smaller diameter, while 10% by volume have a larger diameter and "D10" is the volume-weighted diameter, wherein 10% of the particles, by volume, have a smaller diameter, while 90% by volume have a larger diameter. It is sometimes useful to express the D50 value after sonication for 1 minute or less using about 40 watts of sonicating power at room temperature (15° C. to 30° C.). This low power and short period can break up very loose aggregates which will not typically have a negative impact on the in vivo performance of the composition in a subject.

An "enteric coating" is a substance that remains substantially intact in the stomach but dissolves and releases the drug in the small intestine and/or colon. Generally, the enteric coating comprises a polymeric material that prevents release in the low pH environment of the stomach but that ionizes or solubilizes at a higher pH, typically a pH of 5 to 7, but at least above 3.0, more or above 5, or even more specifically at a pH of about 5.5 to about 7, and thus dissolves sufficiently in the small intestine and/or colon to release the active agent therein. In some embodiments, the enteric coatings release greater than 50% of the ganaxolone that is coated in the small intestine. In other embodiments, the enteric coating provides the release of a substantial portion (greater than 40%) of the coated ganaxolone in the mid-small intestine, e.g., the jejunum.

An "enterically coated" formulation of ganaxolone is intended to mean that some or most of the ganaxolone has been enterically coated to ensure that at least some of the drug is released after entering the small intestine, rather than the acidic environment of the stomach. In some embodiments, about 40% to about 60% of the coated ganaxolone particles are released in the middle region of the small intestine to minimize interaction with bile acids and minimize food effects. In some embodiments, the enterically coated formulations provide the release of greater than 80% of ganaxolone in the small intestine.

The enteric coating material should be non-toxic and is predominantly soluble in the intestinal fluid, but substantially insoluble in the gastric fluids. Examples include polyvinyl acetate phthalate (PVAP), commercially available under trade names of Opadry® Enteric from Colorcon®, hydroxypropylmethylcellulose acetate succinate (HPMCAS), cellulose acetate phthalate (CAP), methacrylic acid copolymer, hydroxypropylmethylcellulose succinate, cellulose acetate succinate, cellulose acetate hexahydrophthalate, hydroxypropylmethylcellulose hexahydrophthalate, hydroxypropylmethylcellulose phthalate (HPMCP), cellulose propionate phthalate, cellulose acetate maleate, cellulose acetate trimellitate, cellulose acetate butyrate, cellulose acetate propionate, methacrylic acid/methacrylate polymer, methacrylic acid-methyl methacrylate copolymer, ethyl methacrylate-methylmethacrylate-chlorotrimethylammonium ethyl methacrylate copolymer, and the like, and combinations comprising one or more of the foregoing enteric polymers. Other examples include natural resins, such as shellac, SANDARAC, copal collophorium, and combinations comprising one or more of the foregoing polymers. Yet other examples of enteric polymers include synthetic resin bearing carboxyl groups. The methacrylic acid: acrylic acid ethyl ester copolymers are commercially available under the trade names of "Eudragit® L", such as Eudragit® L 30-D55 from Degussa.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids. Combinations of one or more erosion facilitator with one or more diffusion facilitator can also be used in the present invention.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the ganaxolone formulations described herein, include both natural and artificial agents e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

The term "grinding media" refers to the material used in milling to physically reduce the particle size of a composition. For milling operations, preferred grinding media are spherical balls of yttrium stabilized zirconium oxide, glass or a plastic resin.

"Gastrointestinal fluid" is the fluid of the gastrointestinal tract of a subject or the saliva of a subject or the equivalent thereof. An "equivalent" of stomach or gastric secretion" is an in vitro fluid having similar content and/or pH as stomach secretions such as simulated gastric fluid (SGF) prepared using USP guidance of about 0.1N HCl solution in water containing about 0.03M NaCl at a pH of around 1.2. In addition, an "equivalent" of intestinal secretion" is an in vitro fluid having similar content and/or pH as intestinal secretions such as simulated intestinal fluid (SIF) prepared using USP guidance is an aqueous phosphate buffer system at pH Of 6.7-6.9.

"Ionic Dispersion Modulator" is defined as an organic or inorganic molecule which when added to a small particle composition will change at least one of the following: viscosity, the amount of certain ingredient(s) needed to stabilize particles during the removal of solvent and/or the amount of certain ingredient(s) needed to stabilize solid dosage forms or blends when re-dispersed in SGF and SIF as described in Example 28. An ionic dispersion modulator does not contain a sulfonic acid or sulfonic acid/inorganic salt group at the end of an alkyl carbon chain containing at least 1 saturated carbon atom bonded to the carbon atom bearing the sulfonic acid moiety.

"Immediate Release" means a dosage form that releases at least 80% of drug within 2 hours of administration, more specifically, within 1 hour of addition to a commonly accepted simulated gastric fluid. Typically an immediate release composition is tested in dissolution apparatus (type II most common) in an amount considered to be therapeutic in patients and a volume of SGF of 500-1000 mL.

"Lubricants" and "glidants" are compounds that prevent, reduce or inhibit adhesion or friction of materials. Exemplary lubricants include, e.g., stearic acid, calcium hydroxide, talc, sodium stearyl fumarate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Milling chamber void volume" is the open volume in a milling chamber available to the milling slurry after grinding media has been added. Milling chamber void volume is related to the amount of grinding media (volume %) and the volume of open space when the spherical beads are stacked on one another (grinding media void volume). For 0.2-0.4 mm spherical milling grinding media, a range of approx. 36-42% of the volume occupied by the grinding beads is the grinding media void volume. Milling chamber void volume (mL)=Total milling chamber volume (mL)−volume of grinding media (mL)+grinding media void volume (mL)

"Milling Residence Time" is the time that a particle is present in the milling chamber over the total time of milling to obtain desired particles. Milling Residence Time (MRT) is defined as: MRT (minutes)=Milling chamber void volume (ml)×total milling time (minutes.)/Milling Slurry Vol. (ml)

The term "Milling Slurry" refers to a suspension containing the drug for particle size reduction and other ingredients to facilitate the milling process. The composition of the milling slurry is usually not the final formulation composition The term "milling media" refers to the components of the milling slurry minus the active pharmaceutical ingredient(s).

The term "Milled Slurry" refers the milling slurry after it had been reduced to a small particle suspension by milling. The most preferred milling slurries for a liquid dispersion are those that meet particle size and compositions that can be diluted with water and appropriate ingredients to obtain the final formulation. For a solid dosage form, preferred milled slurries are those that can be utilized with minimal manipulation to yield the final solid dosage form.

"Pharmacodynamics" refers to the factors which determine the biologic response observed relative to the concentration of drug at a site of action.

"Particle Size" refers to a measured distribution of particles and is usually expressed as the "volume weighted median" size unless specified otherwise. Measurement of particle size for ganaxolone formulations described herein use a Horiba LA-910 or Horiba LA-950 laser light scattering instrument with approx. 120 ml of distilled water in the sample chamber, recirculation mode set to 4, agitation set to 1. If the particle size is measured after sonication, the sonication power is set to "low" (40 watts) and the sonication time is 1 minute. This low sonication setting and short duration effectively breaks up very loose aggregates that would not typically affect formulation performance. For ganaxolone the relative refractive index setting is set to 115-010 and sample is added to give a tungsten (blue) light transmittance value of approx. 75%. When measuring a liquid dispersion of ganaxolone, the particle size can be measured by adding the liquid composition via plastic pipette directly to the sample chamber or diluting to approx. 0.5 mg of ganaxolone/ml and adding via a plastic pipette to the sample chamber. When measuring a solid composition of ganaxolone where all particles are water soluble, the solid is dispersed in at least 15 ml of distilled water, agitated manually and then added via plastic pipette to the sample chamber. The solid composition contains water insoluble excipients, they may be removed by filtration through a 5 micron filter, or in the case where the suspension cannot be filtered, and particle size can be determined by subtracting the signal from the non-ganaxolone insoluble components. This is described in the method section of this document.

"Pharmacokinetics" refers to the factors which determine the attainment and maintenance of the appropriate concentration of drug at a site of action.

"Plasticizers" are compounds used to soften the microencapsulation material, film coatings or pharmaceutical blends for compression to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Preservatives" are compounds which inhibit microbial growth and are typically added to dispersions to prevent microbes from growing. Typically amounts of preservatives needed to pass anti-microbial effectiveness testing as described by USP and EU methodology are used to test appropriate preservative levels. Preservatives include but are not limited to potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

A "pulsatile release" dosage form is a dosage form capable of providing more than one peak blood plasma concentration following a single administration. A "pulsatile release" formulation can contain a combination of immediate release, sustained release, and/or delayed release formulations in the same dosage form. "Pharmacokinetic parameters" are parameters which describe the in vivo characteristics of the drug over time, including, for example plasma concentration of the drug. Pharmacokinetic parameters include $C_{max}$, $T_{max}$, and $AUC_{0-\tau}$ (each discussed above).

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200 to 600, glycofurol, transcutol, propylene glycol, and dimethyl isosorbide, miglyol, glycerin, glycerol, and the like.

"Spray Drying" is a process by which a solvent is removed from a composition yielding a dried form of the ingredients in that composition. Drying is effected by spraying the composition through a nozzle into a heated environment containing a vacuum or a flow of air or inert gas. Spray drying can produce amorphous powders of drugs or granulations, both which can be converted into a solid dosage form by those skilled in the art.

"Spray Layering" is a procedure where a solution or suspension containing ingredients are sprayed through a nozzle into a fluidized bed containing particles which are coated with a film containing the composition of the solution or suspension as the solvent is removed by the flow of a heated gas. Spray layering typically involves coating an inert core usually comprised of a sugars and starch or cellulosics or combinations thereof. Such cores are typically 20 to 35 mesh in size. Spray Layering is used extensively for applying coatings (finish or enteric) to solid dosage formulations as well as spherical beads containing a drug for use in a capsule or tablet formulation.

"Stable" means the D50 does not substantially change (greater than 50%) after an initial time is defined (e.g., after milling or a curing period (1 to 3 weeks)) and up to 4 months storage at room temperature (15° to 25° C.). For example, the stable ganaxolone particles described herein in an aqueous dosage form will not show an increase in effective particle size of greater than 50% over a four month storage period, and preferably no increase in effective particle size of greater than 50% over a two year storage period. Similarly, the stable ganaxolone particles described herein in a solid oral dosage form will not show an increase in effective particle size of greater than 50% up to 4 months storage at room temperature (15° to 25° C.) upon dispersion (methods for dispersion are described in the Examples section below). In some embodiments, the formulations described herein will not produce unidentified ganaxolone degradation impurities up to 4 months storage at room temperature (15° to 25° C.) at individual levels of about greater than 0.1% by weight as compared to the impurity levels at the initial time designation.

"Stabilizers" include agents which maintain a desirable attribute of the formulation over a time interval including but not limited to mechanical, chemical and temperature stressing that can be tested in a laboratory setting. Such attributes include stable particle size or homogeneity resulting in concentrations consistent with the labeled potency and maintaining purity. Some but not all of the attributes are listed above.

"Steady state," as used herein, is when the amount of drug administered is equal to the amount of drug eliminated within one dosing interval resulting in a plateau or constant plasma drug exposure.

"Subject" as used herein is any mammal. Subjects include individuals in need of ganaxolone treatment (patients) and individuals not in need of ganaxolone treatment (e.g. normal healthy volunteers. Humans are preferred subjects and patients.

"Suspending agents" or "dispersing agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylcelluloses (e.g., HPC, HPC-SL, and HPC-L), cellulosics, such as, e.g., sodium carboxymethylcellulose, methylcellulose, sodium carboxymethylcellulose hydroxypropylmethylcellulose (e.g., HPMC 2910, Pharmacoat 603, HPMC K100, HPMC K4M, HPMC K15M, and HPMC K100M), hydroxyethylcellulose hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, polyethoxylated sorbitan monolaurate, polyethoxylated sorbitan monolaurate, povidone, magnesium aluminum silicate, 4-(1,1,3,3-tetramethylbutyl)-phenol polymer with ethylene oxide and formaldehyde (also known as tyloxapol), poloxamers, pluronics, and the like. Combinations of HPMC and PVA are especially useful.

"Sustained Release", consistent with its use herein, means a dosage form that allows at least a one dose reduction in dosing frequency per day as compared to the drug in conventional form, such as a solution or an immediate release solid dosage form.

"Surfactants" include compounds such as sodium lauryl sulfate, sodium doccusate, triacetin, vitamin E TPGS, dioctylsulfosuccinate, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)); polyethylene glycols (e.g., Carbowaxs 3550® and 934® (Union Carbide)), polyoxyethylene stearates, colloidal silicon dioxide, phosphates, carboxymethylcellulose calcium, carboxymethylcellulose sodium, methylcellulose, hydroxyethylcellulose, hydroxypropyl methylcellulose, hydroxypropylcellulose, polyvinylpyrrolidone, hydroxypropylmethylcellulose phthalate, noncrystalline cellulose, magnesium aluminium silicate, triethanolamine, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 9085®, which is a tetrafunctional block copolymer derived from sequential addition of propylene oxide and ethylene oxide to ethylenediamine (BASF Wyandotte Corporation, Parsippany, N.J.)); Tetronic 1508® (T-1508, a poloxamine) (BASF Wyandotte Corporation), Tritons X-200®, which is an alkyl aryl polyether sulfonate (Rohm and Haas); Crodestas F-110®, which is a mixture of sucrose stearate and sucrose distearate (Croda Inc.); p-isononylphenoxypoly-(glycidol), also known as Olin-IOG® or Surfactant 10-G® (Olin Chemicals, Stamford, Conn.); Crodestas SL-40® (Croda, Inc.); and SA90HCO, which is $C_{18}H_{37}CH_2C(O)N(CH_3)$—$CH_2(CHOH)_4$ $(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; PEG-phospholipid, PEG-cholesterol, PEG-cholesterol derivative, PEG-vitamin A, PEG-vitamin E, lysozyme, random copolymers of vinyl pyrrolidone and vinyl acetate. The above surfactants are commercially available or can be prepared by techniques known in the art. Many are described in detail in the *Handbook of Pharmaceutical Excipients*, published jointly by the American Pharmaceutical Association and The Pharmaceutical Society of Great Britain (The Pharmaceutical Press, 2000), specifically incorporated by reference.

A "therapeutically effective amount" or "effective amount" is that amount of a pharmaceutical agent to achieve a pharmacological effect. The term "therapeutically effective amount" includes, for example, a prophylactically effective amount. An "effective amount" of ganaxolone is an amount needed to achieve a desired pharmacologic effect or therapeutic improvement without undue adverse side effects. The effective amount of a ganaxolone will be selected by those skilled in the art depending on the particular patient and the disease. It is understood that "an effect amount" or "a therapeutically effective amount" can vary from subject to subject, due to variation in metabolism of ganaxolone, age, weight, general condition of the subject, the condition being treated, the severity of the condition being treated, and the judgment of the prescribing physician.

"Treat" or "treatment" refers to any treatment of a disorder or disease, such as preventing the disorder or disease from occurring in a subject which may be predisposed to the disorder or disease, but has not yet been diagnosed as having the disorder or disease; inhibiting the disorder or disease, e.g., arresting the development of the disorder or disease, relieving the disorder or disease, causing regression of the disorder or disease, relieving a condition caused by the disease or disorder, or reducing the symptoms of the disease or disorder.

"Viscosity enhancing agents" are agents which are typically added to a particulate dispersion to increase the viscosity and prevent or slow settling of the particles. Viscosity enhancing agents in solid dosage forms are used on occasion to form a gel matrix as water permeates the solid dosage form and can delay the release of the pharmaceutically active ingredient(s). Viscosity enhancing agents include but are not limited to the following: methyl cellulose, xanthangum, carboxymethylcellulose, hydroxypropylcellulose, hydroxypropylmethylcellulose, hydroxypropylmethylcellulose-acetatestearate, hydroxypropylmethylcellulose phthalate, carbomer, polyvinyl alcohol, alginates, acacia, chitosans and combinations thereof.

"Wetting agents" include surfactants and are used to enhance the dispersion of a drug in a composition or after administration of the composition to a subject. Wetting agents can also act as stabilizers. Examples of wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

I. Ganaxolone Formulations and Compositions

Ganaxolone is poorly soluble in water and other pharmaceutically acceptable solvents. As a result of its low aqueous solubility, there exists a need in the art for ganaxolone formulations, which provide increased bioavailability and therapeutic efficacy of ganaxolone. However, it is known that increasing the bioavailability of an active agent likewise results in the possibility of increased side effects.

Certain ganaxolone compositions and formulations described herein display enhanced pharmacokinetic (PK) and pharmacodynamic (PD) profiles and/or minimized side effects as compared to conventional ganaxolone formulations known in the art. Specifically, certain ganaxolone formulations described herein provide increased therapeutic benefit resulting from enhanced PK/PD properties including increased exposure of ganaxolone in the fasted or fed state, improved maintenance of ganaxolone at steady state, and decreased maximal plasma levels ($C_{max}$) of ganaxolone as compared to the levels immediately prior to the next dose ($C_{min}$) at steady state. Certain ganaxolone compositions and formulations described herein also provide a reduced fed/fasted exposure and/or $C_{max}$ ratio with the administration of ganaxolone, extended periods of ganaxolone exposure per dose, reduced plasma $C_{max}$ levels needed to achieve efficacious exposure over a dosing interval at steady state, steady state plasma levels immediately prior to the next dose of about 20 to 50 ng/ml and a $C_{max}/C_{min}$ ratio less than 4 in an aqueous oral composition and a $C_{max}/C_{min}$ ratio less than 3 in a solid dosage form for oral administration at steady state. Steady state plasma levels of certain ganaxolone formulations described herein are about 50 ng/ml or from about 100 ng/ml to about 10 ng/ml.

Certain formulations described herein reduce the risk of ganaxolone side effects including ataxia, sedation and somnolence relative to conventional ganaxolone formulations. In certain embodiments improved performance compared to conventional ganaxolone formulations can be seen on acute doses. In other embodiments, maximal benefit of the ganaxolone formulations described herein can be seen at steady state.

The ganaxolone formulations described herein can be administered to a subject by conventional administration route. Ganaxolone oral solid dosage forms and oral aqueous suspensions are included herein. Modified, controlled, and pulsatile release ganaxolone dosages forms are provided herein.

It is to be understood that any of the dosage forms described herein comprising a ganaxolone formulation, either alone or when administered in combination with another drug can provide at least one or more of the above-described enhanced pharmacokinetic properties and minimize side effects resulting from reduced $T_{max}$ and elevated $C_{max}$ levels of ganaxolone in the blood plasma.

II. Ganaxolone Particles

The ganaxolone formulations described herein comprise stable ganaxolone particles existing in crystalline form, amorphous form, semi-crystalline form, semi-amorphous form, and mixtures thereof. In some embodiments, the ganaxolone formulations comprise an amorphous form of ganaxolone having an average effective particle size of up to about 10 microns. In other embodiments, the ganaxolone formulations comprise an amorphous form of ganaxolone, which is either coated or encapsulated with an excipient matrix, with the matrix having an effective particle size up to 300 microns. In other embodiments, the ganaxolone formulations comprise a non-amorphous form of ganaxolone comprising ganaxolone particles having an effective average particle size by weight of less than about 500 nm. In other embodiments, the ganaxolone particles have an effective average particle size by weight of less than about 400 nm, an effective average particle size by weight of less than about 300 nm, an effective average particle size by weight of less than about 200 nm, or an average effective particle size by weight of less than about 100 nm when measured by the above techniques. In yet another embodiment, the ganaxolone particles have a particle size distribution wherein the ganaxolone particles have an effective particle size by weight of less than about 400 nm and wherein the standard deviation of the particle size distribution is less than about 100 nm.

In other embodiments, the ganaxolone particles by weight have a particle size 500 nm, i.e., less than about 500 nm, less than about 400 nm, less than about 300 nm, less than about 200 nm, or less than about 100 nm with less than at least 20%, at least about 15% or at least about 10% of the total particles having a particle size greater than 1 micron.

In one embodiment, the ganaxolone particles have a particle size of around 300 nm with a distribution wherein 90% of the particles by weight have an effective particle size by weight between about 100 nm and 800 nm. In another embodiment, the ganaxolone particles have a particle size or around 100 nm and a distribution wherein 90% of the particles by weight have an effective particle size by weight between about 50 nm and 250 nm.

In other embodiments, the ganaxolone compositions described herein comprise stable ganaxolone particles having a particle size by weight of less than 500 nm formulated with ganaxolone particles having a particle size by weight of greater than 500 nm. In such embodiments, the formulations have a particle size distribution wherein about 10% to about 100% of the ganaxolone particles by weight are between about 100 nm and about 300 nm, about 0% to about 90% of the ganaxolone particles by weight are between about 300 nm and about 600 nm, and about 0% to about 30% of the ganaxolone particles by weight are greater than about 600 nm. In one embodiment, the formulation has a particle size distribution wherein about 20% of the ganaxolone particles by weight are between about 100 nm and about 300 nm, about 40% of the ganaxolone particles by weight are between about 300 nm and about 600 nm, and about 30% of the ganaxolone particles by weight are greater than about 600 nm. In still another embodiment, the formulation has a particle size distribution wherein about 30% of the ganaxolone particles by weight are between about 100 nm and about 300 nm, about 40% of the ganaxolone particles by weight are between about 300 nm and about 600 nm, and about 30% of the ganaxolone particles by weight are greater than about 600 nm. In yet another embodiment, the formulation has a particle size distribution wherein about 50% of the ganaxolone particles by weight are between about 100 nm and about 300 nm, about 40% of the ganaxolone particles by weight are between about 300 nm and about 800 nm, and about 10% of the ganaxolone particles by weight are greater than about 800 nm.

III. Benefits of Small Particle Sizes of Poorly Soluble Drugs

The particle size of ganaxolone particles is an important factor which can effect bioavailability, blend uniformity, segregation, and flow properties. In general, smaller particle sizes of a drug increases the drug absorption rate of permeable drugs with substantially poor water solubility by increasing the surface area and kinetic dissolution rate. The particle size of ganaxolone can also affect the suspension or blend properties of the pharmaceutical formulation. For example, smaller particles are less likely to settle and therefore form better suspensions.

In various embodiments, the ganaxolone formulations, in aqueous dispersions or as dry powders (which can be administered directly, as a powder for suspension, or used in a solid dosage form), can comprise a non-amorphous form of ganaxolone with compatible excipients having an effective particle size by weight of less than about 500 nm, or less than about 400 nm, or less than about 300 nm, or less than about 200 nm, or less than about 100 nm. In other embodiments, the ganaxolone formulations comprise an amorphous form of ganaxolone with compatible excipients having an average effective particle size by weight of up to about 10 microns.

Effects of Particle Size Range of Poorly Soluble Drugs

The amount of a permeable water insoluble drug (<1 mg/ml in water at pH 7) that can be absorbed is related to its particle size. In various embodiments, stable ganaxolone particles can be obtained with a D50 of less than about 100-500 nm. As one reduces particles further, the kinetic dissolution rate increases as a function of the drugs surface area. In general, reducing the drugs particle size in half doubles the surface area of the particles. When poorly soluble drugs (<1 mg/ml water solubility at pH 7 to 7.4) are extensively milled (long milling residence time), small particles of around 100 nm can be obtained. These particles tend to have a mean value within 25 to 30% of the median, a standard deviation of less than around 50% of the D50 value and a D90 of around 1.5 to 1.75 times the D50 value. Very small particles (50 to 200 nm) with a tight distribution around the D50 value as described above can result in high maximal plasma levels, but occasionally lower total exposures ($AUC_{0-\tau}$) can be realized as the extended release due to particle dissolution is lost.

In some instances it is desirable to not have a high Cmax typically associated with small particle formulations. For compounds with high in vivo clearance, it is also desirable to extend the absorption phase to minimize the frequency with which dosing in a subject is needed. One aspect of this invention is that the ganaxolone complexes formed after adding a complexing agent and any resulting aggregates can accomplish this goal in that the surface area of aggregates is typically much greater than a single particle of that size. Also in the case of dispersion of dosage forms in gastrointestinal fluids (simulated or in vivo administration), loose aggregates that can dissociate substantially during gastrointestinal transit can provide an extended drug absorption phase which is desirable. For each compound one has to determine the effect of these loose and tight aggregates, but it is typical that loose aggregates which can be reversed quickly with a small amount of energy (40 watts of sonication in water for 1 minute or less) will not impact the performance of the drug exposure and can extend the duration of drug release and minimize the plasma $C_{max}$ levels in a subject. For a composition containing stable ganaxolone particles, it is desirable to have a D50 with or without sonication between 100 to 500 nm and no more than about 15% of the ganaxolone particles greater than 1 micron in size.

It is sometimes desirable to obtain a broader distribution of stable particles than those obtained by milling alone to optimize both the maximal levels and total exposure obtained after a dose of drug. In various embodiments, ganaxolone formulations (both liquid and solid) have had a complexing agent added which serves not only to stabilize particle growth, but provides a broader range of particles to increase the exposure to ganaxolone at a given dose. This extended particle size range is especially desirable in compounds that had the characteristic of being metabolized extensively by the liver after oral administration. In one embodiment, a ganaxolone dispersion has a particle size of around 300 nm, a mean of around 800 nm, a D90 of around 600 nm, a standard deviation of around 1.8 microns and around 7 to 8% of the particles greater than 1 micron.

IV. Dosage Forms

The ganaxolone compositions described herein can be formulated for administration to a subject via any conventional means including, but not limited to, oral, parenteral (e.g., intravenous, subcutaneous, or intramuscular), buccal, intranasal or transdermal administration routes.

Moreover, the pharmaceutical ganaxolone compositions described herein can be formulated into any suitable dosage form, including but not limited to, aqueous oral dispersions, aqueous oral suspensions, solid dosage forms including oral solid dosage forms, aerosols, controlled release formulations, fast melt formulations, effervescent formulations, self-emulsifying dispersions, solid solutions, liposomal dispersions, lyophilized formulations, tablets, capsules, pills, powders, delayed release formulations, immediate release formulations, modified release formulations, extended release formulations, pulsatile release formulations, multiparticulate formulations, and mixed immediate release and controlled release formulations. In some embodiments, ganaxolone formulations provide a therapeutically effective amount of ganaxolone over an interval of about 30 minutes to about 8 hours after administration, enabling, for example, once-a-day, twice-a-day (b.i.d.), or three times a day (t.i.d.) administration if desired. In one embodiment, the ganaxolone particles are formulated into a controlled release or pulsatile solid dosage form for b.i.d. administration. In other embodiments, the ganaxolone particles are dispersed in an aqueous dispersion for b.i.d. administration. Generally speaking, one will desire to administer an amount of ganaxolone that is effective to achieve a plasma level commensurate with the concentrations found to be effective in vivo (e.g., 50 to 100 ng/ml at steady state) for a period of time effective to elicit a therapeutic effect.

Dosage Forms Characterized by Disintegration Profiles

The various release dosage formulations discussed above can be characterized by their disintegration profile. A profile is characterized by the test conditions selected. Thus the disintegration profile can be generated at a pre-selected apparatus type, shaft speed, temperature, volume, and pH of the dispersion media.

Several disintegration profiles can be obtained. For example, a first disintegration profile can be measured at a pH level approximating that of the stomach (about pH 1.2); a second disintegration profile can be measured at a pH level approximating that of one point in the intestine or several pH levels approximating multiple points in the intestine (about 6.0 to about 7.5, more specifically, about 6.5 to 7.0). Another disintegration profile can be measured using distilled water.

The release of formulations may also be characterized by their pharmacokinetic parameters, for example, $C_{max}$, $T_{max}$, and $AUC_{(0-\tau)}$.

As one embodiment the invention provides an solid oral dosage form that is a controlled release or pulsatile release dosage form whereby 30 to 60% of the ganaxolone particles by weight are released from the dosage form within about 2 hours after administration and about 90% by weight of the ganaxolone particles are released from the dosage form within about 7 hours after administration. In another embodiment, a broad size distribution of ganaxolone particles by weight are dispersed in an aqueous dispersion comprising ganaxolone particles of varying effective particle sizes such that the smaller particles provide quick absorption of ganaxolone and the larger particles provide a delayed absorption of ganaxolone. In another embodiment, the solid dosage form is an immediate release dosage form whereby >80% of the ganaxolone particles hours after administration.

Oral Solid Dosage Forms

In some embodiments, the solid dosage forms of the present invention may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of the present invention may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing ganaxolone particles with one or more pharmaceutical excipients to form a bulk blend composition. When referring to these bulk blend compositions as homogeneous, it is meant that the ganaxolone particles are dispersed evenly throughout the composition so that the composition may be readily subdivided into equally effective unit dosage forms, such as tablets, pills, and capsules. The individual unit dosages may also comprise film coatings, which disintegrate upon oral ingestion or upon contact with diluents. These ganaxolone formulations can be manufactured by conventional pharmaceutical techniques.

Preparation of Solid Dosage Forms

Conventional pharmaceutical techniques for preparation of solid dosage forms include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

Formulation Components

The pharmaceutical solid dosage forms described herein can comprise the ganaxolone compositions described herein and one or more pharmaceutically acceptable additives such as a compatible carrier, binder, complexing agent, ionic dispersion modulator, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the ganaxolone formulation. In one embodiment, some or all of the ganaxolone particles are coated. In another embodiment, some or all of the ganaxolone particles are microencapsulated. In yet another embodiment, some or all of the ganaxolone is amorphous material coated and/or microencapsulated with inert excipients. In still another embodiment, the ganaxolone particles not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerin, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose (e.g., Avicel®, Avicel®PH101, Avicel® PH102, Avicel® PH105, etc.), cellulose powder, dextrose, dextrates, dextran, starches, pregelatinized starch, hydroxypropylmethylcellulose (HPMC), hydroxypropylmethylcellulose phthalate, hydroxypropylmethylcellulose acetate stearate (HPMCAS), sucrose, xylitol, lactitol, mannitol, sorbitol, sodium chloride, polyethylene glycol, and the like.

Because ganaxolone is insoluble in water and is relatively permeable, it exhibits a strong correlation between the rate of dissolution and bioavailability. Thus, it is important to optimize the rate of dissolution in biological matrices in order to enhance in vivo drug absorption. In order to release the ganaxolone from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. In some embodiments of the invention, the solid dosage ganaxolone formulation has greater than about 1 w % of a disintegrant. In various embodiments of the present invention, the solid dose ganaxolone formulations have between about 1 w % to about 11 w % or between about 2 wt % to about 8 wt % disintegrant. In yet other embodiments, the ganaxolone formulations have greater than about 2 wt % disintegrant. In some embodiments, combinations of disintegrants provide superior dispersion characteristics compared to single disintegrant at a similar total weight percentage.

Suitable disintegrants for use in the solid dosage forms described herein include, but are not limited to, natural starch such as corn starch or potato starch, a pregelatinized starch such as National 1551 or Amijel®, or a sodium starch glycolate such as Promogel® or Explotab®, a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In one embodiment, Ac-Di-Sol is the disintegrant. The amount of Ac-Di-Sol used in direct compression tableting may vary with typical usage levels between 1 and 3 percent. When added to granulations, generally the same percent is used as with a direct compression formulation. It is often added to both the wet and dried granulations and blends. The amount of Ac-Di-Sol used in capsule formulations generally ranges from 3-6 percent. Reduced interparticle contact within a capsule facilitates the need for elevated levels of disintegrant. Capsules filled on automatic dosater types of equipment, as opposed to semi-automatic or hand-filled machines, are more dense and have a harder structure due to the greater compressional forces needed to form the plug and successfully transfer it into the gelatin or HPMC shell. Greater plug hardness results in greater effectiveness of Ac-Di-Sol.

Binders impart cohesiveness to solid oral dosage form formulations: for powder filled capsule formulation, they aid in plug formation that can be filled into soft or hard shell capsules and in tablet formulation, binders ensure that the tablet remains intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crosspovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations is a function of whether direct compression, wet granulation, roller compaction, or usage of other excipients such as fillers which itself can act as moderate binder are used. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Non water-soluble diluents are compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like. Wetting agents include surfactants.

Suitable surfactants for use in the solid dosage forms described herein include, for example, docusate and its pharmaceutically acceptable salts, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 18000, vinyl pyrrolidone/vinyl acetate copolymer (S630), sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), butylhydroxyanisole (BHA), sodium ascorbate, Vitamin E TPGS, ascorbic acid, sorbic acid and tocopherol.

It should be appreciated that there is considerable overlap between additives used in the solid dosage forms described herein. Thus, the above-listed additives should be taken as merely exemplary, and not limiting, of the types of additives that can be included in solid dosage forms of the present invention. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed Tablets

Compressed tablets are solid dosage forms prepared by compacting the bulk blend ganaxolone formulations described above. In various embodiments, compressed tablets which are designed to dissolve in the mouth will comprise one or more flavoring agents. In other embodiments, the compressed tablets will comprise a film surrounding the final compressed tablet. In some embodiments, the film coating can provide a delayed release of the ganaxolone formulation. In other embodiments, the film coating aids in patient compliance (e.g., Opadry® coatings or sugar coating). Film coatings comprising Opadry® typically range from about 1% to about 3% of the tablet weight. Film coatings for delayed release usually comprise 2-6% of a tablet weight or 7-15% of a spray-layered bead weight. In other embodiments, the compressed tablets comprise one or more excipients.

Capsule Formulations

A capsule may be prepared, e.g., by placing the bulk blend ganaxolone formulation, described above, inside of a capsule. In some embodiments, the ganaxolone formulations (non-aqueous suspensions and solutions) are placed in a soft gelatin capsule. In other embodiments, the ganaxolone formulations are placed in standard gelatin capsules or non-gelatin capsules such as capsules comprising HPMC. In other embodiments, the ganaxolone formulations are placed in a sprinkle capsule, wherein the capsule may be swallowed whole or the capsule may be opened and the contents sprinkled on food prior to eating. In some embodiments of the present invention, the therapeutic dose is split into multiple (e.g., two, three, or four) capsules. In some embodiments, the entire dose of the ganaxolone formulation is delivered in a capsule form. For example, the capsule may comprise between about 100 mg to about 600 mg of ganaxolone. In some embodiments, the capsule may comprise between about 100 to about 500 mg of ganaxolone. In other embodiments, capsule may comprise about 300 mg to about 400 mg of ganaxolone.

Another useful capsule has a shell comprising the material of the rate-limiting membrane, including any of the coating materials previously discussed, and filled with ganaxolone particles. A particular advantage of this configuration is that the capsule may be prepared independently of the ganaxolone particles, thus process conditions that would adversely affect the drug can be used to prepare the capsule. A preferred embodiment is a capsule having a shell made of a porous or a pH-sensitive polymer made by a thermal forming process. An especially preferred embodiment is a capsule shell in the form of an asymmetric membrane; i.e., a membrane that has a thin skin on one surface and most of whose thickness is constituted of a highly permeable porous material. A preferred process for preparation of asymmetric membrane capsules comprises a solvent exchange phase inversion, wherein a solution of polymer, coated on a capsule-shaped mold, is induced to phase-separate by exchanging the solvent with a miscible non-solvent. Examples of asymmetric membranes are disclosed in the European Patent Specification 0 357 369 B1.

Yet another useful capsule, a "swelling plug device", can be used. Ganaxolone particles can be incorporated into a non-dissolving capsule-half of the device, which is sealed at one end by a hydrogel plug. This hydrogel plug swells in an aqueous environment, and, after swelling for a predetermined time, exits the capsule thus opening a port through which the ganaxolone can leave the capsule and be delivered to the aqueous environment. Preferred hydrogel-plugged capsules are those which exhibit substantially no release of ganaxolone from the dosage form until the dosage form has exited the stomach and has resided in the small intestine for about 15 minutes or greater, preferably about 30 minutes or greater, thus assuring that minimal ganaxolone is released in the stomach. Hydrogel-plugged capsules of this type have been described in patent application WO90/19168, which is incorporated herein by reference. A ganaxolone swelling plug device may be prepared by loading ganaxolone into a non-dissolving half-capsule shell which may be formed from a wide variety of materials, including but not limited to polyethylene, polypropylene, poly(methylmethacrylate), polyvinylchloride, polystyrene, polyurethanes, polytetrafluoroethylene, nylons, polyformaldehydes, polyesters, cellulose acetate, and nitrocellulose. The open end of the capsule shell is then "plugged" with a cylindrical plug formed from a hydrogel-forming material, including but not limited to, a homo- or co-poly(alkylene oxide) cross linked by reaction with isocyanate or unsaturated cyclic ether groups, as described in PCT Application WO 90/09168. The composition and length of the hydrogel "plug" is selected to minimize release of ganaxolone to the stomach, to decrease the incidence and/or severity of gastrointestinal side effects. The plugged capsule-half is finally sealed with a water-soluble, e.g., gelatin, capsule-half placed over the hydrogel-plugged end of the ganaxolone-containing non-dissolving capsule-half. In an embodiment of the "swelling plug device", the sealed device is coated with a pH-sensitive enteric polymer or polymer mixture, for example cellulose acetate phthalate or copolymers of methacrylic acid and methylmethacrylate. The weight of the enteric polymer coat will generally be from 2 to 20 wt %, preferably from 4 to 15 wt % of the weight of the uncoated sealed capsule. When this preferred "enteric-coated swelling plug device" is ingested orally, the enteric coat prevents release ganaxolone in the stomach. The enteric coat dissolves quickly, e.g., within about 15 minutes, in the duodenum, triggering swelling of the hydrogel plug, exiting of the hydrogel plug, and release of the incorporated ganaxolone into the gastrointestinal tract at a time greater than about 15 minutes after, and preferably greater than about 30 minutes after, the dosage form has passed from the stomach into the duodenum. Prototype unfilled "swelling plug devices" may be obtained from Scherer DDS Limited, Clydebank, Scotland, under the designation Pulsincap™.

In one embodiment, a ganaxolone formulation comprising dried ganaxolone particles can be filled in a capsule. An exemplary process for manufacturing the ganaxolone particles is the milling/evaporation process. A Ganaxolone particle suspension comprising 10 to 30 total wt % ganaxolone, 1 to 10 total wt % hydroxypropylmethylcellulose (Pharmacoat 603), 0.05 to 0.5 total wt % sodium lauryl sulfate, 0.001 to 0.05 total wt % simethicone emulsion (30% in water), 0.5 to 5% sucrose and 0.1 to 2% NaCl in water is sprayed into a spray granulator using standard parameters known by those skilled in the art. Each wt % is based on the total weight of the suspension. The water is evaporated under vacuum at a temperature of 70 to 90° C. The resulting ganaxolone particles comprise about 50 to 80 wt % of ganaxolone based on the total weight of the solid particles. Additional excipients such as magnesium stearate, Mannitol and a disintegrant can be added for flow and re-dispersion properties. The particles generally have a median particle size (D50) of about 50 nm to about 1000 nm, more specifically, about 100 nm to about 500 nm. In one embodiment, the capsule is a swelling plug device. In another embodiment, the swelling plug device is further coated with cellulose acetate phthalate or copolymers of methacrylic acid and methylmethacrylate. In another embodiment the capsule is a size 0 gelatin capsule.

In another embodiment, a ganaxolone complex formulation comprising a dried ganaxolone complex granulation can be filled in a capsule. Ganaxolone complex particle suspension comprising 10 to 30 wt % ganaxolone, 1 to 10 wt % hydroxypropylmethyl cellulose (Pharmacoat 603), 0.05 to 0.5 wt % sodium lauryl sulfate, 0.015 to 0.2 wt % paraben such as methylparaben, 0.001 to 0.05 wt % simethicone emulsion (30% in water) 0.5 to 5% sucrose and 0.1 to 2% NaCl in water is pumped into a spray granulator using standard parameters known by those skilled in the art. Each wt % of the ganaxolone complex particle suspension is based on the total weight of the suspension. The water is evaporated under vacuum at a temperature of 70° C. to 90° C. The resulting ganaxolone complex granulation comprises about 50-80 wt % of ganaxolone based on the total weight of the solid. Additional excipients such as magnesium stearate, Mannitol and a disintegrant can be added for flow and re-dispersion properties. The dispersed solid (in SGF or SIF) generally have a median particle size (D50) of about 50 nm to about 1000 nm, more specifically, about 100 nm to about 500 nm. In one embodiment, the capsule is a swelling plug device. In another embodiment, the swelling plug device is further coated with cellulose acetate phthalate or copolymers of methacrylic acid and methylmethacrylate.

In yet another embodiment, spray layered ganaxolone particles or spray layered ganaxolone complex particles are filled in a capsule. An exemplary process for manufacturing the spray layered ganaxolone or ganaxolone complex particles is the fluidized bed spraying process. Ganaxolone suspensions or ganaxolone complex suspensions described above are sprayed onto sugar or microcrystalline cellulose (MCC) beads (20-35 mesh) with Wurster column insert at an inlet temperature of 50 to 60° C. and air temp of 30 to 50° C. A 15 to 20 wt % total solids content suspension containing 45 to 80 wt % ganaxolone, 10 to 25 wt % hydroxymethylpropylcellulose, 0.25 to 2 wt % of SLS, 10 to 18 wt % of sucrose, 0.01 to 0.3 wt % simethicone emulsion (30% emulsion) and 0.3 to 10% NaCl, based on the total weight of the solid content of the suspension, are sprayed (bottom spray) onto the beads through 1.2 mm nozzles at 10 mL/min and 1.5 bar of pressure until a layering of 400 to 700% wt % is achieved as compared to initial beads weight. The resulting spray layered ganaxolone particles or ganaxolone complex particles comprise about 30 to 70 wt % of ganaxolone based on the total weight of the particles. In one embodiment the capsule is a size 0 soft gelatin capsule In one embodiment, the capsule is a swelling plug device. In another embodiment, the swelling plug device is further coated with cellulose acetate phthalate or copolymers of methacrylic acid and methylmethacrylate.

In some embodiments the capsule includes at least 250 mg (or at least 300 mg or at least 400 mg) ganaxolone and has a total weight of less than 800 mg (or less that 700 mg). The capsule may contain a plurality of ganaxolone-containing beads, for example spray layered beads. In some embodiments the beads are 12-25% ganaxolone by weight. In some embodiments some or all of the ganaxolone containing beads are coated with a coating comprising 6 to 15% (or 8 to 12%) of the total bead weight. Optimization work typically involves lower loading levels and the beads constitute 30 to 60% of the finished bead weight. Instead of or in addition to ganaxolone containing beads the capsule may contain a granulated ganaxolone composition, wherein the granulated composition comprises ganaxolone, or ganaxolone, and an ionic dispersion modulator. In some embodiments the compositions additionally comprise a complexing agent and an inorganic or organic salt. For example the granulated composition in some embodiments is comprised of 0.3 to 20% (or 1 to 10% or 1 to 5%) by weight inorganic or organic salt. These granulations also typically contain 5 to 30% of a binding agent, 2 to 25% of a water soluble spacing agent and a wetting agent (0.5 to 2%)

The capsule may be pulsatile release ganaxolone oral dosage form, comprising: (a) a first dosage unit comprising a first ganaxolone dose that is released substantially immediately following oral administration of the dosage form to a patient; (b) a second dosage unit comprising a second ganaxolone dose that is released approximately 3 to 7 hours following administration of the dosage form to a patient. For pulsatile release capsules containing beads the beads can be coated with a coating comprising 6 to 15% (or 8 to 12%) of the total bead weight. In some embodiments the coating is a coating that is insoluble at pH 1- to 2 and soluble at pH greater than 5.5.

In certain embodiments the pulsatile release capsule comprises by weight 30 to 50% of the first ganaxolone dose and 50 to 70% of the second ganaxolone dose. This pulsatile release capsule may contain a plurality of beads in which some beads are immediate release beads and other beads are formulated, for example with the use of a coating, for modified release, typically 3 to 10 hours after administration. In other embodiments the pulsatile release capsule contains a plurality of beads formulated for modified release and ganaxolone powder, for example spray granulated ganaxolone, for immediate release.

Formulations Containing Coated Ganaxolone Particles

In some embodiments, the spray layered ganaxolone particles or spray layered ganaxolone complex particles present in ganaxolone formulations, such as the capsule formulation described above, is coated. Ganaxolone particles can be with a modified release coating, such as an enteric coating using cellulose acetate phthalate or copolymers of methacrylic acid and methylmethacrylate. In one embodiment, the enteric coating may be present in an amount of about 0.5 to 15 wt %, more specifically, about 8 to 12 wt %, based on the weight of the spray layered particles. In one embodiment, the spray layered ganaxolone particles or spray layered ganaxolone complex particles coated with the enteric coatings can be filled in a modified release capsule in which both enteric coated and immediate release ganaxolone beads are filled into a soft gelatin capsule. Additional suitable excipients may also be filled with the coated particles in the capsule.

In another embodiment, mixtures of spray layered ganaxolone particles or spray layered ganaxolone complex particles coated with the enteric coatings and those without the enteric coatings at appropriate ratios may be encapsulated in a suitable immediate release capsule. The uncoated particles release ganaxolone immediately upon administration while the coated particles do not release ganaxolone until these particles reach intestine. By controlling the ratios of the coated and uncoated particles, desirable pulsatile release profiles may be obtained. In some embodiments, the ratios between the uncoated and the coated particles are 20/80, or 30/70, or 40/60, or 50/50, w/w to obtain desirable release.

Tablet Spray Layered Dosage Forms

In some embodiments, the spray layered ganaxolone particles or spray layered ganaxolone complex particles described above can be compressed into tablets with commonly used pharmaceutical excipients. Any appropriate apparatus for forming the coating can be used to make the enteric coated tablets, e.g., fluidized bed coating using a wurster column, powder layering in coating pans or rotary coaters; dry coating by double compression technique; tablet coating by film coating technique, and the like. See, e.g., U.S. Pat. No. 5,322,655; *Remington's Pharmaceutical Sciences Handbook*: Chapter 90 "Coating of Pharmaceutical Dosage Forms", 1990.

In various embodiments, the spray layered ganaxolone particles or spray layered ganaxolone complex particles described above and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the ganaxolone formulation into the gastrointestinal fluid.

In other embodiments, the spray layered ganaxolone particles or spray layered ganaxolone complex particles with enteric coatings described above and one or more excipients are dry blended and compressed into a mass, such as a tablet. In one embodiment, the enteric coated particles in the tablet substantially avoids release of ganaxolone, for example less than 15 wt %, in the stomach but releases substantially all ganaxolone (enterically coated), for example, greater than 80 wt %, in the intestine.

In yet other embodiments, a pulsatile release ganaxolone formulation comprises a first dosage unit comprising a formulation made from ganaxolone containing granules made from a spray drying or spray granulated procedure or a formulation made from ganaxolone complex containing granules made from a spray drying or spray granulated procedure without enteric coatings and a second dosage unit comprising spray layered ganaxolone particles or spray layered ganaxolone complex particles with enteric coatings. In one embodiment, the first dosage unit and the second dosage unit are wet or dry blended and compressed into a mass to make a pulsatile release tablet. In one embodiment, the weight ratio between the uncoated particles and the coated particles is about −1:4 to 4:1.

In another embodiment, binding, lubricating and disintegrating agents are blended (wet or dry) to the spray layered ganaxolone or ganaxolone complex spray layered beads to make a compressible blend. The first and the second dosage units are compressed separately and then compressed together to form a bilayer tablet.

In yet another embodiment, the first dosage unit is in the form of an overcoat and completely covers the second dosage unit.

Microencapsulated Formulations

In one aspect of the present invention, dosage forms may include microencapsulated ganaxolone formulations. In some embodiments, one or more other compatible materials are present in the microencapsulation material. Exemplary materials include, but are not limited to, complexing agents, ionic dispersion modulators, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with ganaxolone which sufficiently isolate ganaxolone from other non-compatible excipients. Materials compatible with ganaxolone of the present invention are those that delay the release of the ganaxolone in vivo.

Exemplary microencapsulation materials useful for delaying the release of the formulations comprising ganaxolone include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, Prima-Flo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E10, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, parabens, sodium chloride, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated ganaxolone may be formulated by methods known by one of ordinary skill in the art. Such known methods include, e.g., spray drying processes, spinning disk-solvent processes, hot melt processes, spray chilling methods, spray granulation via fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

The spinning disk method allows for: 1) an increased production rate due to higher feed rates and use of higher solids loading in feed solution, 2) the production of more spherical particles, 3) the production of a more even coating, and 4) limited clogging of the spray nozzle during the process.

Spray granulation via a fluid bed is often more readily available for scale-up. In various embodiments, the material used in the spray-granulation encapsulation process is emulsified or dispersed into the core material in a concentrated form, e.g., 10-60% solids. The microencapsulation material is, in one embodiment, emulsified until about 1 to 3 μm droplets are obtained. Once a dispersion of ganaxolone and encapsulation material is obtained, the emulsion is fed as droplets into the heated chamber of the spray granulator. In some embodiments, the droplets are sprayed into the chamber or spun off a rotating disk. The microspheres are then dried in the heated chamber and fall to the bottom of the chamber where they are harvested.

Roller compaction, which involves dry granulation of single powder or a blended mixture of powders by the use of pressure to form dense compacts (the compacts are subsequently milled to a desired particle size), provides another alternative. It is a simple process that is readily available for use, and does not involved the use of solvents for granulation. Thus, roller compaction eliminates the exposure of sensitive active pharmaceutical ingredients to moisture and drying. Roller compaction can also provide some enhanced stability and taste-masking characteristics to active pharmaceutical by diluting and isolating such components in a granulated matrix of compatible ingredients. Roller compaction also imparts increased density and flow to the powder.

Extrusion/spheronization is another method that involves wet massing of active pharmaceutical ingredients, followed by the extrusion of the wet mass through a perforated plate to produce short cylindrical rods. These rods are subsequently placed into a rapidly rotating spheronizer to shape the cylindrical rods into uniform spheres. The spheres are subsequently dried using a fluid bed drier and then coated with a functional coating using a fluid bed equipped with a Wurster insert and spray nozzle.

Coacervation involves microencapsulation of materials such as active pharmaceutical ingredients and involves a three part process of particle or droplet formation, coacerate wall formation, and capsule isolation. This method can produce very small particle size microcapsules (10-70 microns).

In one embodiment, the ganaxolone particles are microencapsulated prior to being formulated into one of the above forms. In still another embodiment, some or most of the ganaxolone particles are coated prior to being further formulated by using standard coating procedures, such as those described in *Remington's Pharmaceutical Sciences,* 20th Edition (2000).

Coated or Plasticized Formulations

In other embodiments, the solid dosage ganaxolone formulations are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments a powder comprising the ganaxolone formulations described herein may be formulated to comprise one or more pharmaceutical excipients and flavors. Such a powder may be prepared, for example, by mixing the ganaxolone formulation and optional pharmaceutical excipients to form a bulk blend composition. Additional embodiments also comprise a suspending agent and/or a wetting agent. This bulk blend is uniformly subdivided into unit dosage packaging or multi-dosage packaging units. The term "uniform" means the homogeneity of the bulk blend is substantially maintained during the packaging process. In some embodiments, at least about 75% to about 85% of the ganaxolone has an effective particle size by weight of less than 500 nm to about 100 nm. In other embodiments, the ganaxolone comprises at least 90% ganaxolone particles having an effective particle size by weight of less than 500 nm to about 100 nm.

Effervescent Powders

In still other embodiments, effervescent powders are also prepared in accordance with the present invention. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the present invention are added to water, the acids and the base react to liberate carbon dioxide gas, thereby causing "effervescence." Examples of effervescent salts include, e.g: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

The method of preparation of the effervescent granules of the present invention employs three basic processes: wet granulation, dry granulation and fusion. The fusion method is used for the preparation of most commercial effervescent powders. It should be noted that, although these methods are intended for the preparation of granules, the formulations of effervescent salts of the present invention could also be prepared as tablets, according to known technology for tablet preparation.

Wet and Dry Granulation

Wet granulation is one of the oldest methods of granule preparation. The individual steps in the wet granulation process of tablet preparation include milling and sieving of the ingredients, dry powder mixing, wet massing, granulation, drying and final grinding. In various embodiments, the ganaxolone composition is added to the other excipients of the pharmaceutical formulation after they have been wet granulated.

Dry granulation involves compressing a powder mixture into a rough tablet or "slug" on a heavy-duty rotary tablet press. The slugs are then broken up into granular particles by a grinding operation, usually by passage through an oscillation granulator. The individual steps include mixing of the powders, compressing (slugging) and grinding (slug reduction or granulation). No wet binder or moisture is involved in any of the steps. In some embodiments, the ganaxolone formulation is dry granulated with other excipients in the pharmaceutical formulation. In other embodiments, the ganaxolone formulation is added to other excipients of the pharmaceutical formulation after they have been dry granulated.

Solid Dispersions

In other embodiments, the ganaxolone formulations described herein are solid dispersions. Methods of producing such solid dispersions are known in the art and include, but are not limited to, for example, U.S. Pat. Nos. 4,343,789, 5,340,591, 5,456,923, 5,700,485, 5,723,269, and U.S. Pub. Appl 2004/0013734, each of which is specifically incorporated by reference. In some embodiments, the solid dispersions of the invention comprise both amorphous and non-amorphous ganaxolone and can have enhanced bioavailability as compared to conventional ganaxolone formulations. In still other embodiments, the ganaxolone formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions are known in the art and include, but are not limited to, for example, U.S. Pat. Nos. 4,151,273, 5,281,420, and 6,083,518, each of which is specifically incorporated by reference.

Modified Release Forms, Including Controlled Release and Delayed Release

The pharmaceutical solid oral dosage forms comprising the ganaxolone formulations described herein can be further formulated to provide a modified or controlled release of ganaxolone.

In some embodiments, the solid dosage forms described herein can be formulated as a delay release dosage form such as and enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated. Enteric coatings may also be used to prepare other controlled release dosage forms including extended release and pulsatile release dosage forms.

In other embodiments, the ganaxolone formulations described herein are delivered using a pulsatile dosage form. Pulsatile dosage forms comprising the ganaxolone formulations described herein may be administered using a variety of formulations known in the art. For example, such formulations include, but are not limited to, those described in U.S. Pat. Nos. 5,011,692, 5,017,381, 5,229,135, and 5,840,329, each of which is specifically incorporated by reference. Other dosage forms suitable for use with the ganaxolone formulations are described in, for example, U.S. Pat. Nos. 4,871,549, 5,260,068, 5,260,069, 5,508,040, 5,567,441 and 5,837,284, all of which are specifically incorporated by reference. In one embodiment, the controlled release dosage form is pulsatile release solid oral dosage form comprising at least two groups of particles, each containing the ganaxolone formulation described herein. The first group of particles provides a substantially immediate dose of ganaxolone upon ingestion by a subject. The first group of particles can be either uncoated or comprise a coating and/or sealant. The second group of particles comprises coated particles, which comprise from about 2% to about 75%, preferably from about 2.5% to about 70%, and more preferably from about 40% to about 70%, by weight of the total dose of the ganaxolone in said formulation, in admixture with one or more binders. The coating comprises a pharmaceutically acceptable ingredient in an amount sufficient to provide a delay of from about 2 hours to about 7 hours following ingestion before release of the second dose. Suitable coatings include one or more differentially degradable coatings such as, by way of example only, pH sensitive coatings (enteric coatings) such as acrylic resins (e.g., Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, and Eudragit® NE30D, Eudragit® NE 40D®) either alone or blended with cellulose derivatives, e.g., ethylcellulose, or non-enteric coatings having variable thickness to provide differential release of the ganaxolone formulation.

Many other types of controlled release systems known to those of ordinary skill in the art and are suitable for use with the ganaxolone formulations described herein. Examples of such delivery systems include, e.g., polymer-based systems, such as polylactic and polyglycolic acid, polyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms,* 2 Ed., Vol. 1, pp. 209-214 (1990); Singh et al., *Encyclopedia of Pharmaceutical Technology, 2nd* Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983, each of which is specifically incorporated by reference.

In another embodiment, a modified release dosage formulation may comprise a combination of: (a) a compressed tablet core comprising a poorly water soluble active agent, a pharmaceutically acceptable water swellable polymer, and an osmotic agent; and (b) an outer coating layer which completely covers the tablet core and comprises a pH sensitive coating. An optional sealing coat may be applied to the compressed tablet core and an optional coating layer comprising an enteric coating agent may be applied under the outer coating layer as an inner coating or as an overcoat over the outer coating layer. The tablet core may be compressed using a smooth faced tablet die. In one embodiment, the active agent is ganaxolone.

The osmotic agent in this dosage form is any non-toxic pharmaceutically acceptable water soluble compound which will dissolve sufficiently in water and increase the osmotic pressure inside the tablet core. Suitable osmotic agents include simple sugars and salts such as sodium chloride, potassium chloride, magnesium sulfate, magnesium sulfate, magnesium chloride, sodium sulfate, lithium sulfate, urea, inositol, sucrose, lactose, glucose, sorbitol, fructose, mannitol, dextrose, magnesium succinate, potassium acid phosphate and the like. The preferred osmotic agent for the tablet core is a simple sugar such as anhydrous lactose in the range of 0-50% by weight, based on the weight of the compressed, uncoated tablet.

The water swellable polymer may be any pharmaceutically acceptable polymer which swells and expands in the presence of water to slowly release ganaxolone. These polymers include polyethylene oxide, methylcellulose, hydroxypropylcellulose, hydroxypropylmethylcellulose and the like. In a preferred embodiment, the water swellable polymer will be polyethylene oxide (obtained from Union Carbide Corporation under the trade name Polyox WSR Coagulant or Polyox WSR N 80). These materials form a viscous gel in water or other solvent system at a sufficient concentration to control the release of the ganaxolone. This will generally require a concentration of the pharmaceutically acceptable, water swellable polymer of about 0-50% by weight of the compressed, uncoated tablet.

The outer coating comprises a pH sensitive coating which functions as an enteric polymer in that it does not begin to dissolve until pH conditions in excess of the pH of the stomach region are encountered. The pH sensitive coating is the same type of material that is described above. The pH sensitive coating may be present in an amount of about 0.5-15 wt %, more specifically, about 8-12 wt %, based on the weight of the coated tablet core.

Certain controlled release formulation may release less than about 20 wt % of ganaxolone in the formulation is released within the first three hours after administration and more than about 60 percent of ganaxolone between 3 and 10 hours. Other controlled release ganaxolone formulation may release less than about 50 percent within the first three hours after administration and about 50 percent of ganaxolone between 3 and 10 hours.

Enteric Coatings

Enteric coatings should be applied to a sufficient thickness such that the entire coating does not appreciably dissolve in the gastrointestinal fluids at pH below about 5 after 1 hour, but does dissolve at pH about 5 and above. It is expected that any anionic polymer exhibiting a pH-dependent solubility profile can be used as an enteric coating in the practice of the present invention to achieve delivery to the lower gastrointestinal tract. In some embodiments the polymers for use in the present invention are anionic carboxylic polymers. In other embodiments, the polymers and compatible mixtures thereof, and some of their properties, include, but are not limited to:

Shellac, also called purified shellac, a refined product obtained from the resinous secretion of an insect. This coating dissolves in media of pH>7;

Acrylic polymers. The performance of acrylic polymers (primarily their solubility in biological fluids) can vary based on the degree and type of substitution. Examples of suitable acrylic polymers include methacrylic acid copolymers and ammonia methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine; Opadry Enteric are also insoluble in stomach and dissolve in the intestine.

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles<1 µm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions;

PolyVinyl Acetate Phthalate (PVAP). PVAP dissolves in pH>5 and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

A particularly suitable methacrylic copolymer is Eudragit L®, particularly L-30D® and Eudragit 100-55®, manufactured by Rohm Pharma, Germany. In Eudragit L-30D®, the ratio of free carboxyl groups to ester groups is approximately 1:1. Further, the copolymer is known to be insoluble in gastrointestinal fluids having pH below 5.5, generally 1.5-5.5, i.e., the pH generally present in the fluid of the upper gastrointestinal tract, but readily soluble or partially soluble at pH above 5.5, i.e., the pH values present in the small intestine.

In some embodiments, materials include shellac, acrylic polymers, cellulosic derivatives, polyvinyl acetate phthalate, and mixtures thereof. In other embodiments, materials include Eudragit® series E, L, RL, RS, NE, L, L300, S, 100-55, cellulose acetate phthalate, Aquateric, cellulose acetate trimellitate, ethyl cellulose, hydroxypropylmethylcellulose phthalate, hydroxypropylmethylcellulose acetate succinate, polyvinyl acetate phthalate, and Cotteric.

Liquid Formulations

In some embodiments, pharmaceutical ganaxolone formulations are provided comprising the ganaxolone particles described herein and at least one dispersing agent or suspending agent for oral administration to a subject. The ganaxolone formulation may be a powder and/or granules for suspension, and upon admixture with water, a substantially uniform suspension is obtained. As described herein, the aqueous dispersion can comprise amorphous and non-amorphous ganaxolone particles of consisting of multiple effective particle sizes such that ganaxolone particles having a smaller effective particle size are absorbed more quickly and ganaxolone particles having a larger effective particle size are absorbed more slowly. In certain embodiments the aqueous dispersion or suspension is an immediate release formulation. In another embodiment, an aqueous dispersion comprising amorphous ganaxolone particles is formulated such that about 50% of the ganaxolone particles are absorbed within about 3 hours after administration and about 90% of the ganaxolone particles are absorbed within about 10 hours after administration. In other embodiments, addition of a complexing agent to the aqueous dispersion results in a larger span of ganaxolone containing particles to extend the drug absorption phase such that 50-80% of the particles are absorbed in the first 3 hours and about 90% are absorbed by about 10 hours.

A suspension is "substantially uniform" when it is mostly homogenous, that is, when the suspension is composed of approximately the same concentration of ganaxolone at any point throughout the suspension. Preferred embodiments are those that provide concentrations essentially the same (within 15%) when measured at various points in a ganaxolone aqueous oral formulation after shaking. Especially preferred are aqueous suspensions and dispersions, which maintain homogeneity (up to 15% variation) when measured 2 hours after shaking. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

In some embodiments, the ganaxolone powders for aqueous dispersion described herein comprise stable ganaxolone particles having an effective particle size by weight of less than 500 nm formulated with ganaxolone particles having an effective particle size by weight of greater than 500 nm. In such embodiments, the formulations have a particle size distribution wherein about 10% to about 100% of the ganaxolone particles by weight are between about 75 nm and about 500 nm, about 0% to about 90% of the ganaxolone particles by weight are between about 150 nm and about 400 nm, and about 0% to about 30% of the ganaxolone particles by weight are greater than about 600 nm. The ganaxolone particles describe herein can be amorphous, semi-amorphous, crystalline, semi-crystalline, or mixture thereof.

In one embodiment, the aqueous suspensions or dispersions described herein comprise ganaxolone particles or ganaxolone complex at a concentration of about 20 mg/ml to about 150 mg/ml of suspension. In another embodiment, the aqueous oral dispersions described herein comprise ganaxolone particles or ganaxolone complex particles at a concentration of about 25 mg/ml to about 75 mg/ml of solution. In yet another embodiment, the aqueous oral dispersions described herein comprise ganaxolone particles or ganaxolone complex at a concentration of about 50 mg/ml of suspension. The aqueous dispersions described herein are especially beneficial for the administration of ganaxolone to infants (less than 2 years old), children under 10 years of age and any patient group that is unable to swallow or ingest solid oral dosage forms.

Liquid ganaxolone formulation dosage forms for oral administration can be aqueous suspensions selected from the group including, but not limited to, pharmaceutically acceptable aqueous oral dispersions, emulsions, solutions, and syrups. See, e.g., Singh et al., *Encyclopedia of Pharmaceutical Technology*, 2$^{nd}$ Ed., pp. 754-757 (2002). In addition to ganaxolone particles, the liquid dosage forms may comprise additives, such as: (a) disintegrating agents; (b) dispersing agents; (c) wetting agents; (d) at least one preservative, (e) viscosity enhancing agents, (f) at least one sweetening agent, (g) at least one flavoring agent, (h) a complexing agent. and (i) an ionic dispersion modulator. In some embodiments, the aqueous dispersions can further comprise a crystalline inhibitor.

Examples of disintegrating agents for use in the aqueous suspensions and dispersions include, but are not limited to, a starch, e.g., a natural starch such as corn starch or potato starch, a pregelatinized starch such as National 1551 or Amijele®, or sodium starch glycolate such as Promogel® or Explotab®; a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crosspovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropylcellulose ethers (e.g., HPC, HPC-SL, and HPC-L), hydroxypropylmethylcellulose and hydroxypropylmethylcellulose ethers (e.g. HPMC K100, HPMC K4M, HPMC K15M, and HPMC K100M), carboxymethylcellulose sodium, methylcellulose, hydroxyethylcellulose, hydroxypropylmethylcellulose phthalate, hydroxypropylmethylcellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 9080, also known as Poloxamine 9080, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween®60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908%).

Wetting agents (including surfactants) suitable for the aqueous suspensions and dispersions described herein are known in the art and include, but are not limited to, acetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carpool 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Suitable preservatives for the aqueous suspensions or dispersions described herein include, for example, potassium sorbate, parabens (e.g., methylparaben and propylparaben) and their salts, benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth. In one embodiment, the aqueous liquid dispersion can comprise methylparaben and propylparaben in a concentration ranging from about 0.01% to about 0.3% methylparaben by weight to the weight of the aqueous dispersion and 0.005% to 0.03% propylparaben by weight to the total aqueous dispersion weight. In yet another embodiment, the aqueous liquid dispersion can comprise methylparaben 0.05 to about 0.1 weight % and propylparaben from 0.01-0.02 weight % of the aqueous dispersion.

Suitable viscosity enhancing agents for the aqueous suspensions or dispersions described herein include, but are not limited to, methyl cellulose, xanthan gum, carboxymethylcellulose, hydroxypropyl cellulose, hydroxypropylmethyl cellulose, Plasdone® S-630, carbomer, polyvinyl alcohol, alginates, acacia, chitosans and combinations thereof. The concentration of the viscosity enhancing agent will depend upon the agent selected and the viscosity desired.

Examples of natural and artificial sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In one embodiment, the aqueous liquid dispersion can comprise a sweetening agent or flavoring agent in a concentration ranging from about 0.0001% to about 10.0% the weight of the aqueous dispersion. In another embodiment, the aqueous liquid dispersion can comprise a sweetening agent or flavoring agent in a concentration ranging from about 0.0005% to about 5.0% wt % of the aqueous dispersion. In yet another embodiment, the aqueous liquid dispersion can comprise a sweetening agent or flavoring agent in a concentration ranging from about 0.0001% to 0.1 wt %, from about 0.001% to about 0.01 weight %, or from 0.0005% to 0.004% of the aqueous dispersion.

In addition to the additives listed above, the liquid ganaxolone formulations can also comprise inert diluents commonly used in the art, such as water or other solvents, solubilizing agents, and emulsifiers.

Emulsions

In some embodiments, the pharmaceutical ganaxolone formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art include, but are not limited to, for example, U.S. Pat. Nos. 5,858,401, 6,667,048, and 6,960,563, each of which is specifically incorporated by reference.

Exemplary emulsifiers are ethyl alcohol, isopropyl alcohol, ethyl carbonate, ethyl acetate, benzyl alcohol, benzyl benzoate, propylene glycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

Intranasal Formulations

Intranasal formulations are known in the art and are described in, for example, U.S. Pat. Nos. 4,476,116, 5,116,817 and 6,391,452, each of which is specifically incorporated by reference. Ganaxolone formulations prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, complexing agents or buffering and other stabilizing and solubilizing agents may also be present. Preferably, the nasal dosage form should be isotonic with nasal secretions.

Buccal Formulations

Buccal formulations comprising the ganaxolone formulations described herein may be administered using a variety of formulations known in the art. For example, such formulations include, but are not limited to, U.S. Pat. Nos. 4,229,447, 4,596,795, 4,755,386; and 5,739,136, each of which is specifically incorporated by reference. In addition, the buccal dosage forms described herein can further comprise a bioerodible (hydrolyzable) polymeric carrier that may also serves to adhere the dosage form to the buccal mucosa. The buccal dosage form is fabricated so as to erode gradually over a predetermined time period, wherein ganaxolone delivery is provided essentially throughout. Buccal drug delivery, as will be appreciated by those skilled in the art, avoids the disadvantages encountered with oral drug administration, e.g., slow drug absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not comprised, and the carrier is compatible with ganaxolone and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like.

Transdermal Formulations

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144, each of which is specifically incorporated by reference in its entirety. In some embodiments, the transdermal delivery device used with the ganaxolone formulations described herein can comprise a power source, radio frequency, or a brief electrical current to micro-electrodes in the skin creating "channels" or "pores" in the stratum corneum to facilitate the delivery of the ganaxolone formulation, such methods are known in the art and are described in, for example U.S. Pat. Nos. 6,611,706, 6,708, 060, and 6,711,435, each of which is specifically incorporated by reference in its entirety. In other embodiments, the transdermal delivery device can comprise a means for porating the stratum corneum, e.g., micro-lancing, application of sonic energy, or hydraulic puncturing, to facilitate the delivery of the ganaxolone formulation, such methods are known in the art and are described in, for example, U.S. Pat. Nos. 6,142,939 and 6,527,716, each of which is specifically incorporated by reference in its entirety. The pores described by the methods herein are typically about 20-50 microns in depth and to not extend into areas of innervation or vascularization.

The transdermal dosage forms described herein may incorporate certain pharmaceutically acceptable excipients which are conventional in the art. In general, the transdermal formulations described herein comprise at least three components: (1) a ganaxolone or ganaxolone complex formulation; (2) a penetration enhancer; and (3) an aqueous adjuvant. In addition, transdermal formulations can include additional components such as, but not limited to, gelling agents, creams and ointment bases, and the like. In some embodiments, the transdermal formulation can further comprise a woven or nonwoven backing material to enhance drug absorption and prevent the removal of the transdermal formulation from the skin. In other embodiments, the transdermal formulations described herein can maintain a saturated or supersaturated state to promote diffusion into the skin.

Injectable Formulations

Ganaxolone formulations suitable for intramuscular, subcutaneous, or intravenous injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propylene glycol, polyethylene-glycol, glycerol, cremophor and the like), suitable mixtures thereof, vegetable oils (such as olive oil) and injectable organic esters such as ethyl oleate. Additionally, Ganaxolone can be dissolved at concentrations of >1 mg/ml using water soluble beta cyclodextrins (e.g. beta-sulfobutyl-cyclodextrin and 2-hydroxypropylbetacyclodextrin. Proper fluidity can be maintained, for example, by the use of a coating such as lecithin, by the maintenance of the required particle size in the case of dispersions, and by the use of surfactants. Ganaxolone formulations suitable for subcutaneous injection may also contain additives such as preserving, wetting, emulsifying, and dispensing agents. Prevention of the growth of microorganisms can be ensured by various antibacterial and antifungal agents, such as parabens, benzoic acid, benzyl alcohol, chlorobutanol, phenol, sorbic acid, and the like. It may also be desirable to include isotonic agents, such as sugars, sodium chloride, and the like. Prolonged drug absorption of the injectable pharmaceutical form can be brought about by the use of agents delaying absorption, such as aluminum monostearate and gelatin. Ganaxolone suspension formulations designed for extended release via subcutaneous or intramuscular injection can avoid first pass metabolism and lower dosages of ganaxolone will be necessary to maintain plasma levels of about 50 ng/ml. In such formulations, the particle size of the ganaxolone particles and the range of the particle sizes of the ganaxolone particles can be used to control the release of the drug by controlling the rate of dissolution in fat or muscle.

V. Sterile Ganaxolone Formulations

Some of the ganaxolone formulations described herein can be sterile filtered. This property obviates the need for heat sterilization, which can harm or degrade ganaxolone, as well as result effective particle size growth.

Sterile filtration can be difficult because of the required small particle size of the composition. However, this method is suitable and commonly used for dispersions comprising nanoparticles. Filtration is an effective method for sterilizing homogeneous solutions when the membrane filter pore size is less than or equal to about 0.2 microns (200 nm) because a 0.2 micron filter is sufficient to remove essentially all bacteria. Sterile filtration is normally not used to sterilize conventional suspensions of micron-sized ganaxolone because the ganaxolone particles are too large to pass through the membrane pores.

Because Some of the ganaxolone-complex formulations described herein can be sterilized via autoclaving, and because the formulations can have a very small ganaxolone effective average particle size, some sterilized ganaxolone formulations are suitable for parenteral administration. Additionally, a sterile ganaxolone formulation is particularly useful in treating immunocompromised patients, infants or juvenile patients, patients with head trauma and the elderly.

VI. Combination Therapies

The compositions and methods described herein may also be used in conjunction with other well known therapeutic reagents that are selected for their particular usefulness against the condition that is being treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the proliferative disease, the condition of the patient, and the actual choice of compounds used. The determination of the order of administration, and the number of repetitions of administration of each therapeutic agent during a treatment protocol, is well within the knowledge of the skilled physician after evaluation of the disease being treated and the condition of the patient.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In some embodiments, the ganaxolone formulation is administered with at least one other anti-convulsant agent. In other embodiments, the ganaxolone formulation is administered with at least one other anti-epileptic agent. In still other embodiments, the ganaxolone formulation is administered with at least one other anti-anxiety agent. In yet other embodiments, the ganaxolone formulation is administered with at least one other anti-depression agent.

VII. Pharmacokinetic Profiles of the Ganaxolone Formulations

The ganaxolone formulations and dosage forms described herein display pharmacokinetic profiles that can result in $C_{min}$ ganaxolone blood plasma levels at steady state from about 10 ng/ml to about 100 ng/ml. In one embodiment, the ganaxolone formulations described herein provide blood plasma levels immediately prior to the next dose ($C_{min}$) at steady state from about 25 ng/ml to about 100 ng/ml. In another embodiment, the ganaxolone formulations described herein provide $C_{min}$ blood plasma levels at steady state from about 40 ng/ml to about 75 ng/ml. In yet another embodiment, the ganaxolone formulations described herein provide $C_{min}$ blood plasma levels at steady state of about 50 ng/ml. In addition to the improved steady state pharmacokinetics, the present ganaxolone formulations can provide controlled release of ganaxolone such that the $C_{max}/C_{min}$ ratio blood plasma levels of ganaxolone is less than or equal to 4 at steady state for an orally administered dispersion and 3 or less with a solid dosage form. In one embodiment, the ganaxolone formulations described herein provide for the controlled release of ganaxolone such that the $C_{max}/C_{min}$ ratio blood plasma levels of ganaxolone ranges from about 1.5 to 3.5 at steady state. In another embodiment, the ganaxolone formulations described herein provide for the controlled release of ganaxolone such that the $C_{max}/C_{min}$ ratio blood plasma level of ganaxolone is about 3.0 at steady state.

VIIa. Increased Ganaxolone Exposure

The ganaxolone formulations and dosage forms described herein exhibit, in one particular aspect, increased exposure in the fasted state as compared to prior conventional ganaxolone formulations administered at the same dose under the same conditions.

As previously stated, elevated blood plasma levels of ganaxolone can result in undesirable side effects. Thus, lower doses of ganaxolone which can achieve the same or better therapeutic effects as those observed with larger doses of conventional ganaxolone formulations are desired. Such lower doses can be realized with the ganaxolone formulations described herein as a result of the greater exposure observed with the present ganaxolone formulations as compared to conventional ganaxolone formulations. The ganaxolone formulations described herein exhibit exposure in the fasted state as compared to conventional ganaxolone formulations in a range of between at least about 100% and about 500%, preferably between about 150% and about 300%, of the specified therapeutic parameter (e.g., AUC 0-∞ or $AUC_{0-\tau}$) when τ is greater or equal to 24 hours. In one embodiment, the ganaxolone formulation is an aqueous dispersion exhibiting a bioavailability in the fasted state as compared to conventional ganaxolone formulations in a range of between about 150% and about 300%. In another embodiment, the ganaxolone formulation is an oral solid dosage form exhibiting a exposure in the fasted state as compared to conventional ganaxolone formulations in a range of between about 150% and about 400%. In still another embodiment, the ganaxolone formulation is an intranasal dosage form exhibiting enhanced pharmacodynamic effects as compared to a similar oral dose of the conventional formulation. In yet another embodiment, the ganaxolone formulation is a buccal dosage form exhibiting a exposure as compared to conventional ganaxolone formulations in a range of between about 200% and about 800%.

For example, Monaghan et al. have previously published that conventional ganaxolone formulations administered to human subjects in a high fat fed state display pharmacokinetic profiles such that the $AUC_{(0-\infty)}$ blood plasma values ranges from about 1,564±566 (ng/h/ml) to about 2826±316 (ng/h/ml) with doses of 900 mg to 1500 mg, respectfully. By comparison, the $AUC_{(0-\infty)}$ blood plasma values of an administered dose of 900 mg to 1500 mg of the ganaxolone formulation described herein is at least 50% higher than the $AUC_{(0-\infty)}$ blood plasma values exhibited by conventional formulation of ganaxolone administered in the fasted state at the same dosage under the same conditions.

VIIIb. Reduced $C_{max}/C_{min}$ Blood Plasma Ratios of Ganaxolone

The ganaxolone formulations described herein can exhibit reduced $C_{max}/C_{min}$ blood plasma ratios of ganaxolone at steady state as compared to conventional ganaxolone formulations administered at the same dose under the same conditions. For example, Monaghan et al. have previously published that conventional ganaxolone formulations display pharmacokinetic profiles such that multiple doses of conventional ganaxolone formulations given over the course of 14 days resulted in $C_{max}/C_{min}$ blood plasma ratios of ganaxolone of 13.8 (50 mg), 4.4 (200 mg), and 6.7 (500 mg). By comparison, for some embodiments of the invention the $C_{max}/C_{min}$ blood plasma ratios of the ganaxolone formulations described herein are less than 4 at steady state. In one embodiment, the ganaxolone formulations described herein provide for $C_{max}/C_{min}$ blood plasma ratios of ganaxolone range from about 1.5 to 3.5 at steady state. In another embodiment, the ganaxolone formulations described herein provide $C_{max}/C_{min}$ blood plasma ratios of ganaxolone of about 2.5 at steady state. In some embodiments, a transdermal ganaxolone formulation provides $C_{max}/C_{min}$ blood plasma ratios of ganaxolone of less than 1.5 at steady state.

VIIIc. Controlled Exposure Profiles

In certain embodiments, about 40% of the ganaxolone is released from the dosage form within about 3 hours and about 95% of the ganaxolone is released from the dosage form within about 10 hours after administration. In yet another embodiment, about 30% of the ganaxolone is released from the dosage form within about 3 hours and about 90% of the ganaxolone is released from the dosage form within about 10 hours after administration. In yet another embodiment, about 80% of the ganaxolone is released from the dosage form within about 2 hours and about 90% of the ganaxolone is released from the dosage form within about 10 hours after administration.

VIIId. Reduced Fed/Fasted Effects Associated with the Administration of Ganaxolone It is generally known in the art that if a positive fed/fasted effect is seen with a pharmaceutical agent, it is typically related to the dose of the active agent administered such that a lower dose of an active agent will have a lower ratio of $AUC_{(fed)}/AUC_{(fasted)}$ and a higher dose of an active agent will have a higher ratio of $AUC_{(fed)}/AUC_{(fasted)}$. In addition, it is known that dosage forms which substantially eliminate the effects of food on the therapeutic window (levels for efficacy vs. levels giving side effects) are safer than those dosage forms which do not. Thus dosage forms that provide reduced fed/fasted effects provide decreased risks and reduce the potential for side effects, thereby increasing subject safety and compliance. Fed/fasted conditions are in accordance with FDA guidelines for testing drug exposure in the fed and fasted states.

Conventional formulations of ganaxolone display large fed/fasted effects in a manner that is not limited to dose dependency. The ganaxolone formulations described herein are less effected by the fed or fasted state of the subject being administered the formulation. The systemic exposure of the ganaxolone formulations described herein is less sensitive to the type of meal ingested than conventional ganaxolone formulations. This means that there is a reduced difference in the $AUC_{(0-\tau)}$ values of ganaxolone when the ganaxolone formulations are administered in the fed versus the fasted state at therapeutically effective doses. Thus, described herein are ganaxolone formulations that can substantially reduce the effect of food on the pharmacokinetics of ganaxolone. In one embodiment, the ganaxolone formulation is an aqueous dispersion that when administered to a human under two years old, provides a ratio of the $AUC_{(0-\infty)}$ or $AUC_{(0-\tau)}$ values of ganaxolone, when administered in the fed versus the fasted state, of less than about 4. In another embodiment, the ganaxolone formulation is a solid oral dosage form that when administered to a human over twelve years old provides a the ratio of the $AUC_{(0-\tau)}$ values of ganaxolone, when administered in the fed versus the fasted state, of less than about 3. In still another embodiment, the ganaxolone formulation is a solid oral dosage form that when administered to a human over twelve years old provides a ratio of the $AUC_{(0-\tau)}$ values of ganaxolone, when administered in the fed versus the fasted state, of less than about 2. In yet another embodiment, the ganaxolone formulation is a solid oral dosage form that when administered to a human over twelve years old provides a ratio of the $AUC_{(0-\tau)}$ values of ganaxolone, when administered in the fed versus the fasted state, of less than about 1.5. In still another embodiment, the ganaxolone formulation is a solid oral dosage form that when administered to a human over twelve years old provides a ratio of the $AUC_{(0-\tau)}$ values of ganaxolone, when administered in the fed versus the fasted state, ranging from about 3 to about 1.5. In another embodiment, the ganaxolone formulation is a solid oral dosage form that when administered to a human over twelve years old provides a ratio of the $AUC_{(0-\tau)}$ values of ganaxolone, when administered in the fed versus the fasted state, of about 2.

VIII. Dose Amounts

The ganaxolone formulations described herein are administered and dosed in accordance with good medical practice, taking into account the clinical condition of the individual patient, the site and method of administration, scheduling of administration, and other factors known to medical practitioners. In human therapy, the dosage forms described herein deliver ganaxolone formulations that maintain a therapeutically effective amount of ganaxolone of at least 20 ng/ml or typically at least about 50 ng/ml in plasma at steady state while reducing the side effects associated with an elevated $C_{max}$ blood plasma level of ganaxolone.

In various other embodiments of the present invention, the amount ganaxolone administered to a subject via a solid dosage form to achieve a therapeutically effective concentration ganaxolone is typically in the range of about 50 mg to about 800 mg or from about 300 mg to about 700 mg. In one embodiment, a ganaxolone formulation is administered in a solid dosage form at a concentration of about 250 mg to about 650 mg. In another embodiment, the ganaxolone formulation is administered in a solid dosage form at concentration of about 300-400 mg. In another aspect, the solid oral dosage form can be administered twice a day (b.i.d). In yet another aspect, the solid oral dosage form is a controlled release dosage form administered b.i.d. providing a pulsatile release of ganaxolone such that the $C_{max}$ of blood plasma ganaxolone is reduced to avoid adverse effects while simultaneously reducing fed/fasted effects and maintaining total exposure ($AUC_{(0-\infty)}$).

A therapeutically effective concentration of an oral aqueous suspension or dispersion comprising a ganaxolone formulation described herein, administered according to the methods described herein, is typically in the range of about 20 mg/ml to about 150 mg/ml final concentration. In one embodiment, a ganaxolone formulation is administered as an aqueous oral suspension at a concentration of about 25 mg/ml to about 100 mg/ml final concentration. In another embodiment, a ganaxolone formulation is administered as an aqueous oral suspension at a concentration of about 50 mg/ml final concentration. The aqueous oral suspensions comprising a ganaxolone formulation described herein can be administered both as a single dose per day or given multiple times within a 24 hour period. In one aspect, the aqueous oral suspension can be administered three times a day (t.i.d). In another aspect, the aqueous oral suspension can be administered twice a day (b.i.d.).

Contemplated compositions of the present invention provide a therapeutically effective amount of ganaxolone over an interval of about 30 minutes to about 8 hours after administration, enabling, for example, once-a-day, twice-a-day, three times a day, and etc. administration if desired.

In further embodiments, greater than about 95%; or greater than about 90%; or greater than about 80%; or greater than about 70% of the ganaxolone dosed by weight is absorbed into the bloodstream within 8 hours after administration.

In other embodiments, the pharmaceutical formulations provide a release profile for an immediate release dosage form of the ganaxolone, whereby using methods described in Example 29, whereby about 804% (or about 70% or about 90%) of the ganaxolone is released from the dosage form within about 1 hours in SGF and for a delay release ganaxolone dosage form about 60% of the (or preferably 70% or 80%) is released from the composition within about 3 hours in SGF.

IX. Methods of Manufacturing Ganaxolone Formulations Comprising Submicron Particles The ganaxolone formulations described herein can comprise ganaxolone particles having a D50 of less than about 500 nm. The starting ganaxolone composition can be predominantly crystalline, predominantly amorphous, or a mixture thereof. These ganaxolone particles can be made by using any method known in the art for achieving particle sizes of less than 500 nm including, for example, milling, homogenization, supercritical fluid fracture or precipitation techniques. Exemplary methods are described in U.S. Pat. Nos. 4,540,602 and 5,145,684, each of which is specifically incorporated by reference.

Methods of making compositions comprising nanoparticles are also described in U.S. Pat. Nos. 5,518,187; 5,718, 388; 5,862,999; 5,665,331; 5,662,883; 5,560,932; 5,543,133;

5,534,270; 5,510,118; 5,470,583 and U.S. Pub. Appl. 2004/0067251, each of which is specifically incorporated by reference.

A. Milling to Obtain Ganaxolone Dispersions Comprising Submicron Particles

The milling process can be a dry process, e.g., a dry roller milling process, or a wet process, i.e., wet-grinding. In some embodiments, this invention is practiced in accordance with the wet-grinding process described in U.S. Pat. Nos. 4,540,602, 5,145,684, 6,976,647 and EPO 498,482, the disclosures of which are hereby incorporated by reference. Thus, the wet grinding process can be practiced in conjunction with a liquid dispersion medium and dispersing or wetting agents such as described in these publications. Useful liquid dispersion media include water, safflower oil, aqueous salt solutions, ethanol, n-butanol, hexane, glycol and the like. The dispersing, and/or wetting agents can be selected from known organic and inorganic pharmaceutical excipients such as described in U.S. Pat. Nos. 4,540,602 and 5,145,684, and can be present in an amount of 2.0-70%, preferably 3-50%, and more preferably 5-25% by weight based on the total weight of formulation.

The grinding media for the particle size reduction step can be selected from rigid media preferably spherical or particulate in shape, e.g., beads. However, grinding media in the form of other non-spherical shapes are expected to be useful in the practice of this invention.

The grinding media preferably can have a mean particle size up to about 500 microns. In other embodiments of the invention, the grinding media particles have a mean particle size preferably less than about 500 microns, less than about 100 microns, less than about 75 microns, less than about 50 microns, less than about 25 microns, less than about 5 microns, less than about 3 mm, less than about 2 mm, less than about 1 mm, less than about 0.25 mm, or less than about 0.05 mm. For fine grinding, the grinding media particles preferably are from about 0.05 to about 0.6 mm, more preferably, about 0.1 to about 0.4 mm in size. Smaller size grinding media will result in smaller size drug particles as compared to the same conditions using larger sized grinding media.

In selecting material, grinding media with higher density, e.g., glass ($2.6 \text{ g/cm}^3$), zirconium silicate ($3.7 \text{ g/cm}^3$), and zirconium oxide ($5.4 \text{ g/cm}^3$), are generally preferred for more efficient milling. Zirconium oxide, such as 95% Zirconium oxide stabilized with magnesia, zirconium silicate, and glass grinding media provide particles having levels of contamination which are believed to be acceptable for the preparation of therapeutic or diagnostic compositions. However, other media, such as stainless steel, titania, agate, glass, alumina, and approx. 95% zirconium oxide stabilized with yttrium, are believed to be useful. In addition, polymeric media having a density typically from about 1 to about 2 $\text{g/cm}^3$ are also expected to be useful.

If polymeric grinding media is utilized, then the grinding media can comprise particles consisting essentially of the polymeric resin. Alternatively, the grinding media can comprise particles comprising a core having a coating of the polymeric resin adhered thereon. The polymeric resin preferably has a density from 0.8 to 3.0 $\text{g/cm}^3$. Higher density resins are preferred inasmuch as it is believed that these provide more efficient particle size reduction.

In general, polymeric resins suitable for use herein are chemically and physically inert, substantially free of metals, solvent and monomers, and of sufficient hardness and friability to enable them to avoid being chipped or crushed during grinding. Suitable polymeric resins include but are not limited to crosslinked polystyrenes, such as polystyrene crosslinked with divinylbenzene, styrene copolymers, polycarbonates, polyacetals, such as Delrin™, vinyl chloride polymers and copolymers, polyurethanes, polyamides, poly(tetrafluoroethylenes), e.g., Teflon™, and other fluoropolymers, high density polyethylenes, polypropylenes, cellulose ethers and esters such as cellulose acetate, polyhydroxymethacrylate, polyhydroxyethyl acrylate, silicone containing polymers such as polysiloxanes, and the like. The polymeric polymer can be biodegradable. Exemplary biodegradable polymeric polymers include poly(lactides), poly(glycolide) copolymers of lactides and glycolide, polyanhydrides, poly(hydroxyethyl methacylate), poly(imino carbonates), poly(N-acylhydroxyproline)esters, poly(N-palmitoyl hydroxyproline) esters, ethylene-vinyl acetate copolymers, poly(orthoesters), poly(caprolactones), and poly(phosphazenes). In the case of biodegradable polymers, contamination from the media itself advantageously can metabolize in vivo into biologically acceptable products which can be eliminated from the body.

The core material preferably can be selected from materials known to be useful as grinding media when fabricated as spheres or particles. Suitable core materials include but are not limited to zirconium oxides (such as 95% zirconium oxide stabilized with magnesia or yttrium), zirconium silicate, glass, stainless steel, titania, alumina, ferrite, and the like. Preferred core materials have a density greater than about 2.5 $\text{g/cm}^3$. The selection of high density core materials is believed to facilitate efficient particle size reduction.

Useful thicknesses of the polymeric polymer coating on the core are believed to range from about 1 to about 500 microns, although other thicknesses outside this range may be useful in some applications. The thickness of the polymer coating preferably is less than the diameter of the core.

The cores can be coated with the polymeric resin by techniques known in the art. Suitable techniques include spray coating, fluidized bed coating, and melt coating. Adhesion promoting or tie layers can optionally be provided to improve the adhesion between the core material and the resin coating. The adhesion of the polymer coating to the core material can be enhanced by treating the core material to adhesion promoting procedures, such as roughening of the core surface, corona discharge treatment, and the like.

In some embodiments, ganaxolone can be prepared in submicron particle size, e.g., less than about 500 nm. In certain embodiments, the particles can be prepared having an effective particle size by weight of less than about 400 nm. In certain embodiments, particles having an effective particle size by weight of less than 300 nm can be prepared in accordance with the present invention. In other embodiments, particles having an effective particle size by weight of less than 200 nm and about 100 nm can be prepared in accordance with the present invention.

Grinding can take place in any suitable grinding mill. Suitable mills include an airjet mill, a roller mill, a ball mill, an attritor mill, a vibratory mill, a planetary mill, a sand mill and a bead mill. A high energy media mill is preferred when small particles are desired. The mill can contain a rotating shaft.

The preferred proportions of the grinding media, ganaxolone, the optional liquid dispersion medium, and dispersing, wetting or other particle stabilizing agents present in the grinding vessel can vary within wide limits and depends, for example, the size and density of the grinding media, the type of mill selected, the time of milling, etc. The process can be carried out in a continuous, batch or semi-batch mode. In high energy media mills, it can be desirable to fill 80-95% of the volume of the grinding chamber with grinding media. On the other hand, in roller mills, it frequently is desirable to leave the grinding vessel up to half filled with air, the remaining volume comprising the grinding media and the liquid dispersion media, if present. This permits a cascading effect within the vessel on the rollers which permits efficient grinding. However, when foaming is a problem during wet grinding, the vessel can be completely filled with the liquid dispersion medium or an anti-foaming agent may be added to the liquid dispersion.

The attrition time can vary widely and depends primarily upon the particular drug substance or imaging agent, mechanical means and residence conditions selected, the initial and desired final particle size and so forth. For roller mills, processing times from several days to weeks may be required. On the other hand, milling residence times of less than about 2 hours are generally required using high energy media mills.

After attrition is completed, the grinding media is separated from the milled ganaxolone particulate product (in either a dry or liquid dispersion form) using conventional separation techniques, such as by filtration, sieving through a mesh screen, and the like.

In one aspect of the invention, the grinding media comprises beads having a size ranging from 0.05-4 mm, preferably 0.1-0.4 mm. For example, high energy milling of ganaxolone with yttrium stabilized zirconium oxide 0.4 mm beads for a milling residence time of 25 minutes to 1.5 hours in recirculation mode at 2500 RPM. In another example, high energy milling of ganaxolone with 0.1 mm zirconium oxide balls for a milling residence time of 2 hours in batch mode. Additionally, the milling temperature should not exceed 50° C. as the viscosity of the suspension may change dramatically. Elevated temperatures also may result in precipitation of certain polymers in the milling slurry and will increase wear on the mill seals. If supplies of milled suspension exceeds the void milling chamber volume then this process will require recycling the material to a cooled holding tank and re-milling of the material until the desired particle (D50) size and appropriate properties are achieved in continuous mode and the mill is also jacketed with cooling. In another aspect, the mill can be jacketed to help control internal temperatures in both continuous or batch mode. The milling concentration is from about 10% to about 30% ganaxolone by weight vs. the milling media weight. The milling media is defined as the weight of the slurry that is milled minus the weight of the drug in that slurry. In one embodiment, the concentration is 25% ganaxolone by weight vs. the milling media(weight). In one embodiment, the milling media contains at least one agent to adjust viscosity so that the desired particles are suspended evenly, and a wetting and/or dispersing agent to coat the initial ganaxolone suspension so a uniform feed rate may be applied in continuous milling mode. In another embodiment, batch milling mode is utilized with a milling media containing at least one agent to adjust viscosity and/or provide a wetting effect so that the ganaxolone is well dispersed amongst the grinding media.

Xa. Milling to Obtain Stable Particles

A concern with the preparation of any small particle suspension is the stability of the milled particles. The milled particles after a period of time (e.g., four weeks) after milling may tend to agglomerate and result in increased particle size as compared to the particles size immediately after milling. When creating small particle formulations (<500 nm) most compositions never stabilize and continue to grow until large particles (1-30 microns) are realized. The rate at which these particles grow depends on the composition and the residence time of milling. The art around producing small particle compositions of organic molecules has focused on various methods and compositions to suppress particle growth or aggregation. One unanticipated and novel concept discussed herein is adding complexing agent(s) to initially provide rapid particle size growth over a curing period which then becomes a very stable small molecule formulation. This growth in particle size is especially observed initially after adding methylparaben with or without propylparaben or benzoic acid/sodium benzoate. A non-preservative complexing agent is methylanthranilate.

The final stable particle size as measured by volume-weighted-median (D50) is dependent upon the concentration of the complexing agents and/or milling residence time. When the concentration of complexing agents was kept constant, the post-milling growth of particles correlates closely with residence time. Therefore, certain aspects of the present invention are directed to the unexpected observation that the residence time that the active agent particles (e.g., ganaxolone particles) are subjected to during the milling process, has an impact on the variability of the subsequent growth in particles size after milling.

The milling residence time is defined by the following equation:

$$\text{Milling Residence Time} = (\text{milling chamber void volume/milling slurry volume}) \times \text{milling time} \quad \text{(Equation 1)}.$$

Within Equation 1 the void chamber volume is the void space in the mill chamber that can be occupied by the milling slurry. It is calculated by estimating the bead void space in the beads (for 0.4 mm yttrium-stabilized zirconium oxide beads, the bead void space is approximately 36-40% of the beads volume) and void chamber volume is the volume of the milling chamber–the volume of the beads+the bead void space (all in the same volume units). When milling under re-circulating conditions (passing multiple times through a mill by creating a loop between a milling slurry in a vessel and the mill, the disclosed residence times are obtained using flow rates varying from ¼ of the estimated void volume/minute to 3 times (3×) the estimated void chamber volume/minute. Ideally flow rates of 0.5× void chamber volume per minute to 1.5× void volume per minute are used.

As demonstrated in the examples, it has been observed that after obtaining a desired particle size, continued milling which does not significantly reduce the particle size any further, does produce more growth stable particles as compared to the shorter milling residence time. Ganaxolone complex particle size can be controlled by the amount of complexing agent or by re-milling stable particles after curing. See Example 45, which shows that re-milling stabilizes ganaxolone complex particle size. One factor that may contribute to the growth of the particle size is the association of a complexing agent with a ganaxolone particle. It is also possible that this complex can further associate with other particle excipients, e.g., a viscosity enhancing agent or wetting agent. These complexes which are initially reversible under sonication, harden over time to become larger, permanent particles. (See FIG. 1). The curing time is the time needed for the complex to harden and become a stable particle. The effect of the milling residence time may affect the variability of size growth due to that prolonged milling produces more particles with smoother surfaces that have less area for contact and are less prone to aggregation. As will be shown below, one can obtain stable ganaxolone suspensions containing particles with D50's of 100-350 nm by milling a slurry for less time and adding a complexing agent or by milling a slurry at higher speeds for longer periods of time.

With the understanding that milling residence time has a significant impact on ganaxolone stability additional milling experiments were performed. The objectives of the additional milling experiments were (a) to prepare ganaxolone formulations comprising particles having a range of particle sizes including particles with a volume-weighted D50 of less than 500 nm; (b) to prepare ganaxolone formulations comprising particles with D50 of less than 500 nm containing at least one complexing agent; (c) to prepare ganaxolone formulations comprising particles of (a) and (b) that show minimal particle size growth in simulated gastric and intestinal fluids at 36-38° C.; (d) to prepare ganaxolone formulations comprising particles of (a) to (c) that are flavored with artificial flavoring, sweetened with a sweetener, preserved to pass anti-microbial effectiveness testing and other ingredients to enhance palatability. The results of these experiments are presented at the Examples section.

Based on this unexpected observation, certain embodiments of the present invention provide pharmaceutical particles comprising ganaxolone thereof which exhibit a stable growth profile over time, i.e., the particles provide a ratio of D50 four weeks after milling or 4 weeks after a curing period if a complexing agent is added to D50 at the end of milling of 1.5:1 or less. The novel nature of adding a small molecule complexing agent is seen in some embodiments where one can reproducibly increase the particle size mode (highest populated particle size) by about 2-fold in 5-7 days. After this period the particle size and mode is stable for many months.

Certain embodiments of the invention also provide a method of stabilizing the particle growth of pharmaceutical particles comprising milling an active agent (including, but not limited to ganaxolone thereof) for a sufficient time for the particles to provide a ratio of D50 four weeks after milling to D50 at the end of milling of 1.5:1 or less.

In further embodiments, the particles have a ratio of D50 four months after curing or after a long milling residence time to of about 1.25:1 or less; or about 1.15:1 or less.

In order for the milled ganaxolone particles of the present invention to provide a growth stable profile with ganaxolone particles in the 100-350 nm range (D50), the particles have a preferred milling residence time of at least 40 minutes if a complexing agent is added, at least 100 minutes, or at least 120 minutes without a complexing agent added. However, these times are not meant to be limiting. The residence time necessary for obtaining a growth stable formulation can be ascertained by one of skill in the art, given the guidance provided by the present disclosure.

The resultant particles of the milling process disclosed herein can have a D50 of less than 500 nm, less than 400 nm, less than 300 nm, less than 200 nm or less than 100 nm. The resultant particles can also have a D90 of less than 1 micron, less than 500 nm, less than 400 nm, less than 300 nm, less than 200 nm.

For stable particle compositions disclosed herein, the particles can optionally include a complexing agent as disclosed herein. The complexing agent can be a preservative such as methylparaben, propylparaben, benzoic acid/sodium benzoate, a phenolic compound, an organic acid, an organic acid salt, an inorganic acid, an inorganic salt, or a combination thereof.

The processes utilized to obtain the stable particles can be any procedure known to one skilled in the art for producing small particles, e.g., the processes described in Section IXA herein.

The end product of the milling processes to obtain growth stable particles can comprise the active agent particles suspended in a dispersing agent (i.e., a suspension).

Xb. Complexing Agents as Particle Growth Stabilizers

Addition of a complexing agent during or preferably post-milling was found to improve the physical stability of ganaxolone particles formulations (e.g. liquid suspension formulations). The improvement in physical stability is believed to be the result of the formation of complex's of ganaxolone particles and the complexing agent which causes an increase in ganaxolone particle size. Without being bound by theory, it is hypothesized that the increase in ganaxolone particle size in complexing agent containing formulations is achieved through a particle complex forming process. For example, the complexing agent(s) can act as an aggregating or binding agent for ganaxolone particles to stick to each other or to form a ganaxolone-aggregates associated with the complexing agent and possibly other ingredients in the suspension. These aggregates are relatively week during the early stages (first 2-3 days) of the complex formation, e.g. in the case of adding methylparaben or methylparaben and propylparaben or parabens and benzoic acid/sodium benzoate This is evident as sonication of the formulation in this stage can reduce the particle size of the complex, apparently due to the loose nature of the newly-formed complexes. Over a period of time, the aggregates harden, or cure, and the particle size of the aggregates cannot be reduced by sonication. At this point, the curing process is complete. This complex forming process is illustrated in FIG. 1.

Different complexing agents affect the complex formations differently. Formulations are given as wt %/w (weight %/total formulation weight).

The cured ganaxolone-particles appear to have much better physical stability than ganaxolone particles that do not contain the complexing agent. Once the ganaxolone particle complexes are formed, no further substantial increase in ganaxolone particle size is observed. Ganaxolone particles that were milled for less than 2 hours milling residence time and do not contain complexing agents continue to increase gradually in size over a number of months (FIG. 3.).

Addition of a complexing agent during or preferably post-milling was found to improve the physical stability of ganaxolone particles formulations (e.g. liquid suspension formulations). The improvement in physical stability is believed to be the result of the formation of complex's of ganaxolone particles and the complexing agent which causes an increase in ganaxolone particle size. Without being bound by theory, it is hypothesized that the increase in ganaxolone particle size in complexing agent containing formulations is achieved through a particle complex forming process. For example, the complexing agent(s) can act as an aggregating or binding agent for ganaxolone particles to stick to each other or to form a ganaxolone-aggregates associated with the complexing agent and possibly other ingredients in the suspension. These aggregates are relatively weak during the early stages (first 2-3 days) of the complex formation, e.g. in the case of adding methylparaben, or methylparaben and propylparaben, or parabens and benzoic acid/sodium benzoate. This is evident as sonication of the formulation in this stage can reduce the particle size of the complex, apparently due to the loose nature of the newly-formed complexes. Over a period of time, the aggregates harden, or cure, and the particle size of the aggregates cannot be reduced by sonication. At this point, the curing process is complete. This complex forming process is illustrated in FIG. 1.

The particle size range (in addition to milling residence time) prior to contact with the particles growth stabilizer also affects the aggregate curing process. In some embodiments, ganaxolone particles of about 140 nm grew to about 300 nm after curing. On the other hand, ganaxolone particles of about 300 nm only grew to about 350 nm after curing.

In certain embodiments, the complexing agent can be a preservative. The complexing agent is selected from the group consisting of organic acids, carboxylic acids, acid salts of amino acids, sodium metabisulphite, ascorbic acid and its derivatives, malic acid, isoascorbic acid, citric acid, tartaric acid, sodium sulphite, sodium bisulfate, tocopherol, water- and fat-soluble derivatives of tocopherol, sulphites, bisulphites and hydrogen sulphites, anthranilic acid and esters thereof, para-aminobezoic acid and esters, 2,6-di-t-butyl-alpha-dimethylamino-p-cresol, t-butylhydroquinone, di-t-amylhydroquinone, di-t-butylhydroquinone, butylhydroxytoluene (BHT), butylhydroxyanisole (BHA), methylparaben, ethylparaben, propylparaben as well as the paraben salts, pyrocatechol, pyrogallol, propyl/gallate, and nordihydroguaiaretic acid, phosphoric acids, phenols, sorbic and benzoic acids, sodium benzoates, esters, derivatives and isomeric compounds, ascorbyl palmitate, pharmaceutically acceptable salts thereof, and mixtures thereof.

Parabens are esters of para-hydroxybenzoic acid. Parabens which can be utilized in the present invention include methylparaben, ethylparaben, propylparaben, and butylparaben. Other parabens which can be utilized in the present invention include isobutylparaben, isopropylparaben, benzylparaben. Pharmaceutically acceptable salts, e.g., sodium and potassium salts, can also be utilized in the present invention. Especially preferred parabens for use in the present invention include methylparaben and propylparaben and their sodium salts. If the sodium salts of parabens are utilized an equimolar amount of an organic acid, e.g., citric acid should be added. Further evidence that methyl and propyl paraben are acting as a complexing agent is that in the preferred embodiments where 25 wt % ganaxolone containing 0.1%-0.3% sodium lauryl sulfate and 2-5 wt % HPMC (Pharmacoat 603) are milled with a residence time of 35-40 minutes with a particle size D50 range from 120-170 nm and 0.1% methylparaben and 0.02% propylparaben are added, the particle size mode (most populated particle size range) approximately doubles, the composition becomes visibly thick and not possible to filter through 5 um or below filters and after 5-10 days, the particles stop growing and stable particles are realized. As will be shown later, the complexed and cured particles exhibit other desirable attributes that the non-complexed formulations do not have. More compelling evidence of the role of methylparaben and propylparaben in the formation of Ganaxolone particle complexes is that running anti-microbial effectiveness studies under USP conditions shows a typical preservative effect during the first 7-14 days, which is then lost and microbial growth rebounds as there is little methylparaben and propylparaben available to act as a preservative. In fact the preferred ganaxolone oral suspensions use two or three preservatives to obtain sufficient anti-microbial effectiveness to pass US and European preservative testing.

The complexing agent can be present in any suitable amount, e.g., from about 0.001% to about 5%, from about 0.01% to about 2.5%, from about 0.015% to about 1%, from about 0.1% to about 0.5% or from about 0.02% to about 0.1%, based on the weight of the milled slurry.

Certain embodiments of the invention are directed to the initial particle growth due to the association of the ganaxolone particles and the complexing agent. These embodiments are directed to pharmaceutical particles comprising ganaxolone thereof associated with a complexing agent, the particles exhibiting a ratio of D50 after incubation in SGF or SIF at 36-38° C. for 1-3 hours to D50 prior to SGF or SIF incubation of less than about 3:1; less than about 2.7:1, less than about 2.5:1, less than about 2:1, or less than about 1.5:1. In certain embodiments, the invention is directed to pharmaceutical particles comprising ganaxolone thereof aggregated with a complexing agent, the particles exhibiting a ratio of D50 after incubation in SGF or SIF for 1-3 hours to D50 prior to incubation of from about 1.5:1 to about 3:1; from about 1.8:1 to about 2.7:1 or about 2:1 to about 1.5:1.

Certain embodiments of the invention are directed to the "uncured" ganaxolone complexes which are not tightly bound as evidenced by reduction of particle size by sonication. These embodiments are directed to pharmaceutical particles comprising ganaxolone thereof aggregated with a particle growth stabilizer, the particles exhibiting a ratio of D50 after incubation in SGF or SIF for 1 hour at 37° C. and sonication for 1 minute to D50 prior to incubation of less than about 2:1, less than about 1.7:1, less than about 1.5:1 or less than about 1.4:1. Other embodiments exhibit a ratio of D50 after incubation in SGF or SIF for 1 hour and sonication for 1 minute to D50 prior to storage of from about 1:2 to about 2:1, from about 1.3:1 to about 1.8:1 or from about 1.3:1 to less than about 1.5:1.

Certain embodiments of the invention are directed to the "cured" complexes which exhibit stable particle size. These embodiments are directed to pharmaceutical particles comprising ganaxolone thereof complexed with a complexing agent, the particles cured for a sufficient time until an endpoint is reached such that the D50 does not change by more than about 5% as measured over 3 days after curing. In other embodiments, the particles are cured for a sufficient time until an endpoint is reached such that the D50 does not change by more than about 12%, more than about 10%, more than about 8% or more than 5% over 1 month after the curing period.

In further embodiments, the particles are cured for a sufficient time until an endpoint is reached such that the D50 does not change by more than about 5% (over the instrument's variability at the measure particle size) after 20 days after curing, 40 days after curing, 60 days after curing, or 80 days after curing storage conditions of 5° C. to 25° C.)

The endpoint needed to reach stable particles can be ascertained by one skilled in the art. For example, the endpoint can be reached in about 5 days to about 25 days; in about 5 days to about 7 days, in about 7 days to about 14 days, in about 14 days to about 21 days, or about 10 days to about 15 days.

In certain embodiments, the particles have a D50 prior to storage of less than 350 nm, less than 250 nm or less than 150 nm. In other embodiments, the particles have a D50 prior to storage of from about 50 nm to about 350 nm, from about 75 nm to about 250 nm or from about 100 nm to about 150 nm.

The formulation comprising the ganaxolone-complex particles can comprise the complexes suspended in a dispersing agent (i.e., a suspension).

The addition of a complexing agent in the ganaxolone suspension formulations was also found to reduce side effects of ganaxolone while achieving adequate exposure. Without being bound by theory, it is believed that the lower side effect is achieved through larger overall particle size distribution of the ganaxolone-preservative complexes while adequate exposure is achieved through larger surface area of the complex versus a single particle of the same size.

In certain embodiments, desirable formulations can be obtained by using appropriate amounts of a complexing agent, a hydrophilic polymer such as HPMC and/or PVA and other components in ganaxolone suspension formulations to achieve an optimal balance between maximum bioavailability and minimal side effects. An exemplary ganaxolone suspension formulation comprises about 5 wt % ganaxolone, about 5 wt % HPMC, about 0.1 wt % SLS, about 0.1 wt % methylparaben, about 0.02 wt % propylparaben, 0.09% sodium citrate, 0.12% citric acid, 0.06% sodium citrate, 0.03% simethicone emulsion (30% in water) and about 1 wt % PVA, based on the total weight of the final suspension formulation. Additional ingredients such as flavoring agent and sweetener can be added at appropriate levels to make theses formulations more palatable. Another exemplary formulation comprises the same composition as immediately above except with HPMC levels reduced to 2.5%, and PVA removed.

Ganaxolone suspensions comprising HPMC, SLS, methylparaben, propylparaben, and PVA was found to provide desirable pharmacokinetic results in animal studies. A composition without PVA gave higher exposure (2-fold) but also gave higher sedation scores in dogs. Whether PVA is desirable or not in humans will depend on the relative therapeutic ratios.

Cured ganaxolone particulate complexes are more desirable as these compositions will provide a more uniform result due to a decreased change in particle size over time, better thermal stability and less aggregation in the gastrointestinal tract.

As discussed previously, ganaxolone has very low aqueous solubility. One method of improving ganaxolone bioavailability is through the use of smaller ganaxolone particles (e.g., less than about 500 nm). However, an increase in bioavailability will be expected to also result in an increase in side effects (e.g., sedation). Cured formulations comprising ganaxolone-complexes having appropriate particle size (e.g. 200 to 350 nm) can minimize side effects while maintaining adequate exposure. For solid dose forms of Ganaxolone where disintegration can be controlled by other techniques and with drugs without a sedative side effect, maximal dissolution and the smallest stable particle size will usually encompass the most preferred embodiments. As will be demonstrated later, once the curing period is complete, the material can be re-milled to obtain smaller stable particles if desired.

It has also been found that formulations containing ganaxolone complexes reduce the variability in pharmacokinetic parameters between ganaxolone dosed in the fed and fasted states. Example T, below, demonstrates the effect of preservative in ganaxolone particles on Cmax and AUC (0-τ).

In view of the unexpected effect of methylparaben and propylparaben on Cmax and AUC (0-τ) of ganaxolone particles, the present invention is directed to pharmaceutical compositions, wherein the ratio of the fasting Cmax provided by composition(s) with ganaxolone complexes with those to the Cmax provided by the composition without the paraben complexes is less than about 1:2; less than about 1.6 or less than about 1:1.4 In certain embodiments, the ratio of the fasting AUC (0-τ) provided by the composition with a complexing agent to the AUC (0-τ) provided by the composition without the complexing agent is less than 1.4:1; less than about 1.3:1 or less than about 1.2:1. In other embodiments, the ratio of the fed Cmax provided by the stable composition with the complexing agent to the Cmax provided by the composition without the complexing agent is less than about 1:1.4; less than about 1:1.2 or less than about 1:1. The present invention is also directed to formulations containing stable ganaxolone compositions with complexing agents, wherein the ratio of the fed AUC (0-τ) to the fasted AUC (0-τ) provided by the composition is from about 1.5:1 to about 5:1, from about 2:1 to about 4:1, or from about 2.5:1 to about 3:1. In other aspects, the ratio of the fed Cmax to the fasted Cmax provided by the composition is from about 2:1 to about 7:1, from about 2.5:1 to about 5:1, or from about 2.8:1 to about 3.8:1.

Xc. Vinyl Polymers as Pharmacokinetic Modifiers

The use of vinyl polymers (e.g., polyvinyl alcohol (PVA)) during or post-milling appears to have little effect on post-milling particle size under storage conditions at ambient temperature. However, data suggests that vinyl polymers do prevent flocculation of ganaxolone particles in simulated gastric fluid (SGF) and simulated intestinal fluid (SIF). The reduction in flocculation of ganaxolone particles in SGF and SIF is greater in ganaxolone suspension formulations containing vinyl polymers and complexing agents. Once the curing period is over, the ganaxolone complex particles are stable and the added stabilization of PVA to suppress agglomeration/flocculation is not observed.

The use of vinyl polymers was also found to reduce ganaxolone exposure levels and reduce the exposure variability between the fed and fasted state. The use of vinyl polymers in ganaxolone formulations (e.g., in suspensions) was further found to reduce the ratio of Cmax to AUC (0-τ). Data demonstrating the effect of vinyl polymers on the exposure variability between the fed and fasted state and the ratio of Cmax to AUC (0-τ) is shown in Example 18, table 7, wherein PVA is exemplified.

The preferred vinyl polymer of the present invention is polyvinyl alcohol. The amount of the vinyl polymer can be in an amount from about 0.01% to about 5%, based on the total weight of the particles, or can be in an amount of from about 0.1% to about 2%, based on the total weight of the particles or from about 0.5% to about 1.5%, based on the total weight of the liquid formulation.

In view of this unexpected effect of vinyl polymers on the pharmacokinetics of ganaxolone, certain embodiments of the present invention are directed to pharmaceutical compositions comprising particles comprising ganaxolone thereof and a vinyl polymer, the particles having a D50 of less than about 500 nm. In certain embodiments, the particles have a D90 of less than about 500 nm.

The pharmaceutical compositions of the present invention containing ganaxolone and a vinyl polymer can have the ratio of the fasting Cmax provided by the composition with the vinyl polymer to the Cmax provided by the composition without the vinyl polymer of less than about 0.75:1; less than about 0.60:1 or less than about 0.50:1.

In certain embodiments, the ratio of the fasting Cmax provided by the composition with the vinyl polymer to the Cmax provided by the composition without the vinyl polymer is more than about 0.20:1; more than about 0.30:1 or more than about 0.40:1.

In other embodiments, the ratio of the fasting AUC (0-τ) provided by the composition with the vinyl polymer to the AUC (0-τ) provided by the composition without the vinyl polymer is less than about 0.8:1; less than about 0.70:1 or less than about 0.6:1.

The certain embodiments, the ratio of the fed Cmax provided by the composition with the vinyl polymer to the Cmax provided by the composition without the vinyl polymer is less than about 0.95:1; less than about 0.85:1 or less than about 0.75:1.

In other embodiments, the ratio of the fed Cmax provided by the composition with the vinyl polymer to the Cmax provided by the composition without the vinyl polymer is more than about 0.20:1; more than about 0.30:1 or more than about 0.40:1.

In further embodiments, the ratio of the fed AUC (0-τ) provided by the composition with the vinyl polymer to the AUC (0-τ) provided by the composition without the vinyl polymer is less than about 0.9:1; less than about 0.80:1 or less than about 0.7:1.

In certain embodiments, the ratio of the fed AUC (0-τ) to the fasted AUC (0-τ) provided by the PVA composition is from about 1:1 to about 5:1, from about 1.5:1 to about 4:1, or from about 2:1 to about 3:1

In other embodiments, the ratio of the fed Cmax to the fasted Cmax provided by the PVA composition is from about 1.5:1 to about 2.5:1, from about 1.6:1 to about 2.4:1, or from about 1.8:1 to about 2.2:1.

The use of vinyl polymers with ganaxolone also results in reduced flocculation of the particles. In certain embodiments containing vinyl polymers, the D50 does not increase more than about 25%, not more than about 20% or not more than about 15% after 3 hours in SGF. In other embodiments, the D50 does not increase more than about 25%, not more than about 20% or not more than about 15% after 3 hours in SIF.

In embodiments containing ganaxolone and a vinyl polymer, the ganaxolone can be complexed with ingredients such as parabens, organic acids, organic acid salts, aromatic acids and aromatic esters, inorganic acids, inorganic salts, pharmaceutically acceptable salts or a combination thereof (see above).

In certain embodiments containing both vinyl polymers and at least one complexing agent, the D50 does not increase more than about 15%, not more than about 12% or not more than about 8% after 1 hour in SGF. In other embodiments, the D50 does not increase more than about 15%, not more than about 10% or not more than about 8% after 1 hour in SIF.

A pharmaceutical composition comprising particles comprising ganaxolone, the particles having a D50 of less than 500 nm, the composition providing a ratio of fed AUC (0-τ) to fasted AUC (0-τ) in beagle dogs from about 1:1 to about 2.5:1, from about 1.2:1 to about 1.9:1, or from about 1.4:1 to about 1.8:1.

While certain formulations have been exemplified which provide particular pharmacokinetic parameters, certain embodiments of the invention are directed to ganaxolone formulations which provide particular pharmacokinetic profiles, regardless of the particular excipients utilized in the formulation. The profiles include (i) a ratio of fed Cmax to fasted Cmax from about 1.5:1 to about 4:1, from about 1.6:1 to about 3:1, or from about 1.8:1 to about 2.5:1, (ii) an AUC (0-24) from about 100 to about 375 ng*h/mL or from about 150 to about 325 ng*h/mL for a 200 to a 500 mg ganaxolone administered to an adult human in the fasted state, (iii) a Cmax from about 25 to about 85 ng/mL for after a 200 to a 500 mg ganaxolone dose administered to an adult subject in the fasted state, (iv) an AUC (0-24) hours from about 250 to about 1200 ng*h/mL or from about 400 to about 1000 ng*h/mL for after a 200 to a 500 mg ganaxolone dose administered to an adult subject in the fed state, and (v) a Cmax from about 60 to about 350 ng/mL or from about 80 to about 275 ng/mL after a 200 to a 500 mg ganaxolone dose administered to an adult subject in the fed state.

XI. Milling with Simethicone as an Anti-Foaming Agent

Foaming during the nanosizing of pharmaceutical products can present formulation issues and can have negative consequences for particle size reduction. For example, high levels of foam or air bubbles in the mill can cause a drastic increase in viscosity rendering the milling process inoperable. Even a very low level of air presence can dramatically reduce milling efficiency causing the desired particle size unachievable. This may be due to the resultant air in the mill cushioning the milling balls and limiting grinding efficiency. The air also can form a microemulsion with the milled ingredients which presents many issues with respect to the delivery of an accurate dose and palatability.

Simethicone is a known anti-foaming agent. However, simethicone is not water soluble and therefore would be expected to interfere with a laser/light scattering particle size determination. Therefore, simethicone would not be expected to be a suitable anti-foaming agent to be utilized in the particle reduction of pharmaceutical agents.

Regardless of this expectation, the present invention is directed to the observation that simethicone is suitable to be used as an anti-foaming agent in the reduction of particle size of pharmaceutical products as it does not interfere with the measurement of the particles. This may be due to simethicone being transparent to tungsten and laser light.

Simethicone can be added to the milling process, e.g., as a 30% emulsion sold by Dow Corning (Dow Corning 7-9245 or Dow Corning Q7-2587), however, any suitable percentage of simethicone in any suitable formulation can be utilized.

The amount of 30% simethicone emulsion utilized in the particle reduction procedures of the present invention can be any suitable amount, e.g., 500 ppm or less, or 350 ppm or 100 ppm or less, to eliminate or substantially eliminate the foam of the ganaxolone milling slurry, facilitating exclusion of air from the mill. One skilled in the art would be able to ascertain the amount of simethicone from different percentages of simethicone formulations In view of the observation that simethicone is a suitable anti-foaming agent for use in particle reductions, certain embodiments of the present invention are directed to a method of milling pharmaceutical products comprising incorporating a pharmaceutically active agent, a suitable amount of simethicone, milling beads and optional pharmaceutically acceptable excipients into a mill; and milling mixture for a suitable time to obtain nanosized particles. In preferred embodiments, the active agent is ganaxolone thereof. The optional pharmaceutically acceptable excipients can be any of the excipients utilized in preparing small particles as disclosed herein.

The simethicone can be added as its pure liquid form (100%) or can be mixed with a suitable vehicle prior to incorporation into the milling process of the present invention. For example, the simethicone can be added in the form of a diluted liquid, including not limited to, a solution or an emulsion, or a suspension. The concentration of simethicone in the liquid can be from about 1% to about 99%; from about 20% to about 80% or from about 20% to about 50%. Preferably, the simethicone is in a 30% emulsion.

The amount of simethicone present in the milling slurry can be any suitable amount which provides the intended benefits described above. Typical amount employed with good results ranges from 50-300 ppm.

In certain embodiments, the recovered ganaxolone particles contain a trace amount of simethicone in the final product. The final product comprising ganaxolone particles may comprise from about 0.001% to about 0.1% simethicone, or from about 0.005% to about 0.05% simethicone, based on the totals weight of the composition.

The end product of the milling processes utilizing simethicone can comprise the active agent particles suspended in a dispersing agent (i.e., a suspension).

XIb. Microprecipitating to Obtain Ganaxolone Dispersions Comprising Nanoparticles Ganaxolone particles can also be prepared by homogeneous nucleation and precipitation in the presence of a wetting agent or dispersing agent as described in U.S. Pat. No. 5,560,932 and U.S. Pat. No. 5,665,331, which are specifically incorporated by reference. Such ganaxolone particles are stable and do not show and appreciable increase in effective particle size over time. This is a method of preparing stable dispersions of ganaxolone in the presence of one or more dispersing or wetting agents and one or more colloid stability enhancing surface active agents. Such a method comprises, for example: (1) dispersing ganaxolone in a suitable liquid media; (2) adding the mixture from step (1) to a mixture comprising at least on dispersing agent or wetting agent such that at the appropriate temperature, the ganaxolone is dissolved; and (3) precipitating the formulation from step (2) using an appropriate anti-solvent (e.g., water). The method can be followed by removal of any formed salt, if present, by dialysis or filtration and concentration of the dispersion by conventional means. In one embodiment, the ganaxolone particles are present in an essentially pure form and dispersed in a suitable liquid dispersion media. A preferred liquid dispersion medium is water. However, other liquid media can be used including, for example, aqueous salt solutions, oils (e.g., safflower, olive or cremephor), and solvents such as ethanol, t-butanol, hexane, and glycol. The pH of the aqueous dispersion media can be adjusted by techniques known in the art. In this embodiment, the ganaxolone particles comprise a discrete phase having been admixed with a dispersing agent or wetting agent. Useful dispersing agents or wetting agents are experimentally determined, but effectively minimize the difference in lipophilicity of ganaxolone and the dispersion media by inducing a non-covalent ordered complex between the media, the wetting agent, and ganaxolone.

XIc. Homogenization to Obtain Ganaxolone Dispersions Comprising Nanoparticles

In yet another embodiment, the ganaxolone particles described herein are produced by high pressure homogenization (see generally U.S. Pat. No. 5,510,118). Such a method comprises dispersing ganaxolone particles in a liquid dispersion medium, followed by subjecting the dispersion to repeated homogenization to reduce the particle size of the ganaxolone to the desired effective average particle size. The ganaxolone particles can be reduced in size in the presence of at least one or more dispersing agents or wetting agents. Alternatively, the ganaxolone particles can be contacted with one or more dispersing agents or wetting agents either before or after attrition. Other compounds, such as a diluent, can be added to the ganaxolone/dispersing agent composition before, during, or after the size reduction process. In one embodiment, unprocessed ganaxolone can then be added to a liquid medium in which it is essentially insoluble to form a premix. The concentration of the ganaxolone in the liquid medium can vary from about 0.1-60% w/w, and preferably is from 5-30% (w/w). It is preferred, but not essential, that the dispersing agents or wetting agents be present in the premix. The concentration of the dispersing agents or wetting agents can vary from about 0.1 to 90%, and preferably is 1-75%, more preferably 20-60%, by weight based on the total combined weight of the ganaxolone and dispersing agents or wetting agents. The apparent viscosity of the premix suspension is preferably less than about 1000 centipoise. The premix then can be transferred to the microfluidizer and circulated continuously first at low pressures, then at maximum capacity having a fluid pressure of from about 3,000 to 30,000 psi until the desired particle size reduction is achieved. The particles must be reduced in size at a temperature which does not significantly degrade the drug substance or cause significant particle size growth through solubilization. Next, one of two methods can be used to collect the slurry and re-pass it in a microfluidizer. The "discreet pass" method collects every pass through the microfluidizer until all of the slurry has been passed through before re-introducing it again to the microfluidizer. This guarantees that every substance or particle has "seen" the interaction chamber the same amount of times. The second method re-circulates the slurry by collecting it in a receiving tank and allowing the entire mixture to randomly mix and pass through the interaction chamber.

Dispersing agents and/or wetting agents, if not present in the premix, can be added to the dispersion after attrition in an amount as described for the premix above. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20-80 kHz for a time of about 1 to 120 seconds.

The relative amount of ganaxolone and dispersing agents and/or wetting agents can vary widely. The dispersing agents and/or wetting agents preferably are present in an amount of about 0.1-10 mg per square meter surface area of ganaxolone. The dispersing agents or wetting agents can be present in an amount of 0.1-90%, preferably 5-50% by weight based on the total weight of the dry ganaxolone particles during the particle size reduction.

The resulting ganaxolone dispersion is stable and consists of the liquid dispersion medium and the above-described particles. The dispersion of ganaxolone particles can be spray coated onto sugar spheres or beads or onto a pharmaceutical excipient in a fluid-bed spray coater by techniques well known in the art.

XId. Fluid Bed Spray-Granulation to Obtain Amorphous Ganaxolone Compositions

In still another embodiment, the ganaxolone particles described herein are produced by spraying-drying or by spray-drying into a fluid bed. Such a method comprises spraying a mixture of ganaxolone and at least one solubility enhancer and/or wetting agent and/or viscosity enhancing agent and optionally a crystallization inhibitor compound in solvent comprised of one or more organic solvents or a mixture of water and one or more alcohols, under conditions that allow the solvent to be removed from said mixture fast enough in the case of a fluidized bed to deposit amorphous or semi-amorphous material onto a carrier bead or in the case of direct spray drying onto the excipients mixture producing a powder.

In one embodiment, the process generally carried out by a) introducing a carrier excipient in the form of a dry powder, spray granules or microgranules into a fluidized bed drier in which the bed is kept at from about 40° C. to about 200° C., preferably about 50° C. to about 100° C.; b) spraying onto the fluidized bed of excipient a pharmaceutically acceptable alcohol (e.g., ethanol, n-butanol, methanol, and mixtures thereof) or organic solvent (acetone, ethyl acetate, toluene) solution comprising ganaxolone and at least one solubility enhancer (e.g. Cholesterol, Vitamin E TPGS, Cremophor and a crystal inhibitor (e.g. Povidone K-12, Hydroxypropylmethylcellulose acetate stearate (HPMCAS) and a binder (lactose, sucrose, starch) which can become amorphous upon spray drying such that stable particles of ganaxolone solution exist in a mixture with the carrier excipient, wherein said stable particles of ganaxolone are amorphous or a combination of amorphous and crystalline material with broad particle size range from 200 nm to 2 microns. The resulting ganaxolone particles are stable and maintain increased kinetic dissolution properties as determined by standard dissolution methods (in vitro) over a 1 year period at 25° C. in a solid dosage form. The ganaxolone containing mixture can be further processed into a solid dosage form or packaged for reconstitution into an aqueous dispersion.

In another embodiment, the process is carried out by a) introducing a carrier excipient in the form of a dry powder, spray granules or microgranules into a fluidized bed drier in which the bed is kept at from about 50° to about 200° C., preferably about 50° to about 100° C.; b) spraying onto the fluidized bed of excipient a water-containing mixture of ganaxolone and at least one solubility enhancer, a crystal inhibitor, and a dispersing agent such that stable particles containing ganaxolone exist in a mixture with the excipient, wherein said stable particles of ganaxolone have an effective particle size of about 500 nm to about 1 μm. The resulting ganaxolone particles are stable and do not appreciably increase in effective particle size over time The carrier excipient is preferably a highly water-soluble compound or polymer. The resulting mixture of water soluble carrier excipient, such as a sugar or sugar alcohol, and ganaxolone is advantageous because the carrier excipients can disperse into water, thereby increasing the dissolution rate of ganaxolone particles in aqueous media.

Useful carrier excipients that can be employed in the fluidized bed for pharmaceutical compositions include, but are not limited to, saccharides, such as sugars and sugar alcohols (for example, lactose or sucrose, mannitol, or sorbitol), starches, flour, cellulose preparations and/or salts such as carbonates, bicarbonates and phosphates, for example, tricalcium phosphate or calcium hydrogen phosphate.

Sugars and sugar alcohols used as a carrier excipient include sugar or sugar alcohols having a molecular weight of less than 500 daltons, and capable of easily dispersing and dissolving in water, thereby improving dissolution rate of ganaxolone. Examples of sugars and sugar alcohols usable in the present invention include xylitol, mannitol, sorbitol, arabinose, ribose, xylose, glucose, mannose, galactose, sucrose, lactose, and the like. They can be used alone, or as a mixture of two or more of these compounds. In one embodiment, the sugars are sucrose or mannitol.

Useful solubility enhancers, other than organic solvents, that can be employed in the fluidized bed for pharmaceutical compositions include, but are not limited to, propylene glycol, PEG having a molecular weight greater than 400 daltons, cholesterol, letichin, cremophor, Vitamin E TPGS, triacetin, olive oil and castor oil.

Useful crystal inhibitors that can be employed with spray drying for pharmaceutical compositions include, but are not limited to, hydroxypropylmethylcellulose acetate stearate, polyvinylpyrrolidones (e.g., povidone K-12), and propylene glycol.

The ganaxolone particles generated by any of the methods described herein can be utilized in solid or aqueous liquid dosage formulations, such as controlled release formulations, pulsatile dosage forms, multiparticulate dosage forms, solid dose fast melt formulations, lyophilized formulations, tablets, capsules, aqueous dispersions, or aerosol formulations.

XII. Methods of Making Small Particle Ganaxolone Formulations

Small particle ganaxolone formulations can be manufactured using the methods described in, for example, in U.S. Pat. Nos. 4,783,484, 4,826,689, 4,997,454, 5,741,522 and 5,776,496, each of which is specifically incorporated by reference.

Such methods include: (1) forming a solution of ganaxolone in a suitable organic solvent. This can occur as the ganaxolone is synthesized as a dissolved solid, or it can be done by simply dissolving particles of ganaxolone in the solvent of choice. Any solvent that is miscible in water is satisfactory, and includes for example, dimethylacetamide (DMA), dimethylformamide (DMF) and dimethyl sulfoxide (DMSO). (2) diluting the solution with a non-solvent that does not cause ganaxolone to precipitate. The non-solvent causes greater dispersion of the dissolved molecules of ganaxolone in the liquid phase. Greater dilution of the solution with non-solvent produces larger particles, and less dilution of the solution with non-solvent produces smaller particles. The non-solvent should not precipitate the ganaxolone when it is added to the solution. Non-solvents in which the compound is slightly more soluble than in water are preferred, for example, include lower aliphatic alcohols, such as ethanol. Also, proportions of non-solvent to solvent at a ratio of 2 or more can produce 1 to 3 micron sized particles (depending on other parameters); and ratios of less than 2 produce submicron particles, at least as applied to DMSO solutions diluted with ethanol. (3) To precipitate the ganaxolone from the solution in a desired particle size, an aqueous solution of a surfactant and or soluble binders and dispersing agents is prepared in sufficient quantity to effect complete precipitation of the ganaxolone and to stabilize the resulting suspension of particles against aggregation. The surfactant provides the stabilization against aggregation, and the water is the precipitating agent. Presence of extra surfactant is advisable to ensure stabilization so that precipitated particles suspended in liquid do not aggregate, forming particles of an improperly large size. Surfactants are chosen for their compatibility with the compound and their ability to stabilize a suspension of ganaxolone particles. For example, a solution of 5% C-30 or 0.1% C-15 polyvinylpyrrolidone (PVP) in water is preferred; but 5% Pluronic F-68, 0.33% gelatin, 0.33% gelatin plus 0.6% Hetastarch, 0.33% gelatin plus 0.002% propylene glycol, 2% polyvinylpyrrolidone/vinyl acetate copolymer, and 0.33% gelatin plus 2% sucrose can also be used. Another embodiment uses 5% HPMC (Pharmacoat 603), 0.3% SLS and 1% PVA. To precipitate ganaxolone particles in the desired sizes, the aqueous solution and the organic solution are combined under controlled conditions of temperature, ratio of infusion rate to stirring rate, and the proportion of non-solvent to solvent in the dispersed solution. The precipitation of ganaxolone occurs exothermically, heating the organic solution and resulting suspension. The temperature of the solution and resulting suspension is controlled to achieve the particle size of precipitate that is desired. Higher solution temperatures during precipitation produce larger particles, and lower solution temperatures during precipitation produce smaller particles. Also, faster infusion rates at constant stirring rate of organic solution produce smaller particles, and slower infusion rates produce larger particles. (4) When the precipitation is complete, extra aqueous surfactant solution can be added to stabilize the suspended ganaxolone particles against agglomeration. The extra solution can be added at a rapid rate, since all the ganaxolone is now precipitated in uniform sized particles. The precipitated particles are promptly separated from the organic solvents to prevent re-dissolving and re-precipitation of particles at undesirable sizes. Centrifuging is the preferred way to do this. Promptly after separating the particles from the organic liquid, the particles are washed or rinsed with normal saline solution to remove solvent and excess surfactant.

The ganaxolone particles generated by the methods described herein can be utilized in solid or aqueous liquid dosage formulations, such as controlled release formulations, solid dose fast melt formulations, lyophilized formulations, tablets, capsules, aqueous dispersions, or aerosol formulations.

XIII. Other Formulations Utilizing Small Particles of Ganaxolone

In certain embodiments, the present invention is directed to a pharmaceutical composition comprising particles comprising (i) ganaxolone thereof, (ii) a cellulosic polymer and (iii) sodium lauryl sulfate; wherein 90% of the particles by weight have an effective particle size of less than about 500 nm. Another embodiment comprises (i), (ii), (iii) and (iv) a complexing agent In other embodiments, the particles comprising (i), (ii) and (iii) above, and (i), (ii), (iii) and (iv) can have any effective particle size, range, or any other characteristic (e.g., pharmacokinetic profile) as disclosed herein. Additionally an ionic dispersion modulator and a water soluble spacer can be added. These formulations can also contain a polymer selected from the group consisting of polyvinylpyrrolidone, polysaccharides, copolymers of vinyl acetate and vinyl pyrrolidone, polyvinyl alcohol, copolymers of vinyl acetate and vinyl alcohol, carboxymethylcellulose and mixtures thereof.

In certain embodiments, the cellulosic polymer of (ii) is hydroxypropylmethylcellulose (Pharmacoat 603).

In certain embodiments, the present invention is directed to a pharmaceutical composition comprising particles comprising (i) ganaxolone thereof, (ii) a polymer selected from the group consisting of polyvinylpyrrolidone, polysaccharides, copolymers of vinyl acetate and vinyl pyrrolidone, polyvinyl alcohol, copolymers of vinyl acetate and vinyl alcohol, carboxyalkylcelluloses, and mixtures thereof, and (iii) a material selected from the group consisting of sodium lauryl sulfate and dioctyl sodium sulfosuccinate, wherein 90% of the particles by weight have an effective particle size of less than about 500 nm. In other embodiments, the particles comprising (i), (ii) and (iii) above, can have any effective particle size, range, or any other characteristic (e.g., pharmacokinetic profile) as disclosed herein. These formulations can also contain a cellulosic polymer.

In certain embodiments, the polymer of (ii) is a copolymer of vinyl acetate and vinyl pyrrolidone.

In certain embodiments, the ionic dispersion modulator is an organic or inorganic salt which does not contain a sulfonic acid or sulfonic acid/inorganic salt counterion group at the end of an alkyl chain containing more than one saturated carbon atom bonded to the carbon atom bearing the sulfonic acid moiety.

In certain embodiments, the water soluble spacer is a saccharide or inorganic salt which do not contain a sulfonic acid or sulfonic acid/inorganic salt counterion group at the end of an alkyl chain containing more than one saturated carbon atom bonded to the carbon atom bearing the sulfonic acid moiety.

The formulations of the present invention can also include a complexing agent including but are not limited to parabens, organic acids, organic acid salts, aromatic acids and aromatic esters inorganic acids, inorganic salts, and combinations thereof. Complexing agents do not contain a sulfonic acid or sulfonic acid/inorganic salt counterion group at the end of an alkyl chain containing more than one saturated carbon atom bonded to the carbon atom bearing the sulfonic acid moiety.

The formulations of the present invention can also include preservatives including but are not limited to parabens, organic acids, organic acid salts, aromatic acids, aromatic esters, inorganic acids, inorganic salts, pharmaceutically acceptable salts and combinations thereof.

Wetting agents such as sodium lauryl sulfate also do not appear to affect the post milling particle size under storage conditions at ambient temperature. However, addition of wetting agents during the milling process does improve the processing properties such as reduction of back pressure and more efficient grinding by reducing the overall viscosity of the milling slurry.

An anti-foaming agent can also be added to improve the milling process. For example, presence of simethicone (e.g., at 0.01% level) during the milling process Did not alter characterization of the formulation and greatly improved the efficiency and reliability of the milling process. The addition of simethicone also produces a final aqueous formulation that will foam less and provide more accurate dosing for the patient. In certain embodiments, the ranges of ganaxolone, HPMC, PVA, SLS, parabens, benzoic acid/sodium benzoate and simethicone in the milling and the final suspension formulations are given in TABLE 1 as a weight percent (wt %) based on the total weight of the respective compositions.

TABLE 1

| Component | Milling Compositional Range, wt % to total weight | Formulation Compositional Range, wt % to total weight |
|---|---|---|
| GNX | 10 to 30 | 3 to 20 |
|  | Or 15 to 27 | Or 4 to 10 |
|  | Or 10 to 25 | Or 4 to 6 |
| HPMC | 2 to 10 | 2 to 10 |
|  | Or 2 to 6 | Or 2 to 6 |
| PVA | 0 to 5 | 0 to 5 |
|  | Or 0.5 to 2.5 | 0.5 to 2.5 |
| SLS | 0 to 1 | 0 to 1 |
|  | Or 0.1 to 0.5 | 0.1 to 0.5 |
| Simethicone, 100% or 3x levels if 30% emulsion used | 0 to 1 | 0 to 1 |
|  | Or 0 to 0.04 | Or 0 to 0.04 |
| Methylparaben | 0 to 0.25 | 0 to 0.25 |
|  | Or 0 to 0.1 | Or 0 to 0.1% |
| Propylparaben | 0 to 0.25 | 0 to 0.25 |
|  | Or 0 to 0.04 | Or 0 to 0.04 |
| Sodium Benzoate/ Benzoic acid | 0 to 0.2 | 0 to 0.2 |

The particles disclosed above can be prepared according to any of the methods disclosed herein or by the methods described in U.S. Pat. Nos. 6,375,986; 6,428,814; 6,432,381; 6,592,903; 6,908,626; or 6,969,529; the disclosures of which are hereby incorporated by reference.

In certain embodiments, the invention is directed to a pharmaceutical composition comprising particles comprising (i) ganaxolone thereof, (ii) a polymer selected from the group consisting of polyvinylpyrrolidone, polysaccharides, copolymers of vinyl acetate and vinyl pyrrolidone, polyvinyl alcohol, copolymers of vinyl acetate and vinyl alcohol, carboxyalkylcelluloses, cellulosic polymers and mixtures thereof, and (iii) a material selected from the group consisting of sodium lauryl sulfate and dioctyl sodium sulfosuccinate (DOSS) and (iv) an ionic dispersion modulator and (v) a water soluble spacer, wherein 90% of the particles by weight have an effective particle size of less than about 500 nm (or any effective particle size, range, or any other characteristic as disclosed herein), wherein the composition comprises (a) an immediate release component comprising a first portion of the particles and providing an immediate release of the ganaxolone or pharmaceutically acceptable salt thereof; and (b) a controlled release component comprising a second portion of the particles and providing a controlled release of the ganaxolone or pharmaceutically acceptable salt thereof.

In certain embodiments, the controlled release component provides a release selected from the group consisting of sustained release or delayed release.

In certain embodiments, the controlled release component comprises a coating comprising a hydrophobic material, coated on the second portion of particles.

In certain embodiments, the controlled release component comprises a matrix comprising the second portion of particles dispersed in a hydrophobic material.

In certain embodiments, the immediate release component and the controlled release component are independently selected from the group consisting of a tablet, a pill, multiparticulates, a powder, a capsule, a solid dispersion, a solid solution, a pellet, or a granule.

In certain embodiments, the hydrophobic material is selected from the group consisting of an acrylic polymer, a cellulosic polymer, shellac, zein, fatty alcohols, hydrogenated fats, fatty acid esters, fatty acid glycerides, hydrocarbons, waxes, stearic acid, stearyl alcohol, and mixtures thereof.

In certain embodiments, the hydrophobic material is an enteric polymer.

In certain embodiments, the enteric polymer is selected from the group consisting of shellac, acrylic polymers, cellulose derivatives, polyvinyl acetate phthalate and mixtures thereof.

In certain embodiments, the delayed release component provides a dose of the ganaxolone or pharmaceutically acceptable salt thereof delayed by from about 2 hours to about 12 hours after administration.

In certain embodiments, the delayed release component provides a dose of the ganaxolone or pharmaceutically acceptable salt thereof delayed by from about 2 hours to about 8 hours after administration.

In certain embodiments, the delayed component provides a dose of the ganaxolone or pharmaceutically acceptable salt thereof delayed by from about 3 hours to about 7 hours after administration.

In certain embodiments, the controlled release component provides a sustained release of the ganaxolone or pharmaceutically acceptable salt thereof for about 2 hours to about 6 hours after administration.

In certain embodiments, the controlled release component provides a sustained release of the ganaxolone or pharmaceutically acceptable salt thereof for about 3 hours to about 10 hours after administration.

In certain embodiments, the coating further comprises a plasticizer, a colorant, a detackifier, a surfactant, an antifoaming agent, a lubricant or a mixture thereof.

In certain embodiments, the immediate release component and the controlled release component independently comprise one or more pharmaceutically acceptable additives from the group consisting of carriers, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, antifoaming agents, antioxidants, preservatives, or one or more combinations thereof.

The pharmaceutical dosage forms disclosed herein having an immediate release component and a controlled release component in this section (XIII) can provide any pharmacokinetic profile as disclosed herein.

The dosage forms can be prepared according to any of the methods disclosed herein or by the methods described in U.S. Pat. Nos. 5,209,746; 5,213,808; 5,221,278; 5,260,068; 5,260,069; 5,308,348; 5,312,390; 5,318,588; 5,340,590; 5,391,381; 5,456,679; 5,472,708; 5,508,040; 5,840,329; 5,980,508; 6,214,379; 6,228,398; 6,248,363; 6,514,518; 6,569,463; 6,607,751; 6,627,223; 6,730,325; 6,793,936; 6,902,742 and 6,923,988, the disclosures of which are hereby incorporated by reference.

XII. Methods of Use of Ganaxolone Formulations

The ganaxolone formulations described herein can be administered in therapeutically effective amounts for the treatment of a subject that has had or is anticipating a convulsive state including, but not limited to, status epilepticus, epileptic seizures or spasms. Specific types of epileptic seizures include, but are not limited to, tonic-clonic (Grand Mal), partial (Focal) seizures, catamenial seizures, acute repetitive seizure, psychomotor (complex partial) seizures, absence (Petit Mal) seizure, and myoclonic seizures.

The ganaxolone formulations described herein can also be used for the treatment of Infantile Spasms (IS). Infantile Spasm is a specific type of seizure seen in an epilepsy syndrome of infancy and early childhood known as West Syndrome. The onset is predominantly in the first year of life, typically between 3-6 months. The typical pattern of IS is a sudden bending forward and stiffening of the body, arms, and legs; although there can also be arching of the torso. Spasms tend to begin soon after arousal from sleep. Individual spasms typically last for 1 to 5 seconds and occur in clusters, ranging from 2 to 100 spasms at a time. Infants may have dozens of clusters and several hundred spasms per day. Infantile spasms usually stop by age 5, but are often replaced by other seizure types. West Syndrome is characterized by infantile spasms, abnormal and chaotic brain wave patterns, and mental retardation.

Additional conditions where the ganaxolone small particle formulations described herein can be used to treat include, but are not limited to, anxiety, stress, panic, depression and depression related disorders (e.g., post-partum depression), insomnia, premenstrual syndrome, Post Traumatic Stress Disorder (PTSD), substance abuse withdrawal (e.g. alcohol, benzodiazepine, barbiturate and cocaine), and hypertension. The ganaxolone formulations described herein can also be used in the treatment of pain, migraine headaches and headaches (including migraine) associated with the pre and peri-menstrual period.

Other conditions diseases which the ganaxolone formulations described herein can be used to treat include sphingolipid storage diseases, such as Neimann Pick Type-C(NPC) and Mucolipidosis Type IV (ML-IV) lipid accumulation.

Additionally, the ganaxolone formulations described herein can be used for the treatment of neurodegenerative diseases including, but not limited to, AIDS-associated dementia, Alzheimer's disease, Huntington's disease, and Parkinson's disease diseases.

Actual dosage levels of the ganaxolone formulations described herein may be varied to obtain an amount of active ingredient that is effective to obtain a desired therapeutic response for a particular composition and method of administration. The selected dosage level therefore depends upon the desired therapeutic effect, on the route of administration, on the desired duration of treatment, and other factors. However, one aspect of the formulations and compositions described herein is to provide ganaxolone formulations that comprise therapeutically effective amounts of ganaxolone such that the ganaxolone blood plasma levels being maintained at steady state are from about 10 ng/ml to about 100 ng/ml ($C_{min}$) upon administration. In one embodiment, the ganaxolone formulations described herein can be used for the treatment of Infantile Spasms or an epilepsy related disorder wherein the formulation provides a therapeutically effective amount of ganaxolone ($C_{min}$) of about 25 to 50 ng/ml of ganaxolone in the blood plasma at steady state. In another embodiment, the ganaxolone formulations described herein can be used for the treatment of a non-epilepsy related disorder wherein the formulation provides a therapeutically effective amount of ganaxolone ($C_{min}$) of about 15 to 30 ng/ml of ganaxolone in the blood plasma at steady state.

XIII. Pharmacokinetic Analysis

Any standard pharmacokinetic protocol can be used to determine blood plasma concentration profile in humans following administration of a ganaxolone formulation described herein, and thereby establish whether that formulation meets the pharmacokinetic criteria set out herein. For example, a randomized single dose crossover study can be performed using a group of healthy adult human subjects. The number of subjects should be sufficient to provide adequate control of variation in a statistical analysis, and is typically about 10 or greater, although for certain purposes a smaller group can suffice. Each subject receives administration at time zero a single dose (e.g., 300 mg) of a test formulation of ganaxolone, normally at around 8 am following an overnight fast. The subjects continue to fast and remain in an upright position for about 4 hours after administration of the ganaxolone formulation. Blood samples are collected from each subject prior to administration (e.g., 15 minutes) and at several intervals after administration. For the present purpose it is preferred to take several samples within the first hour and to sample less frequently thereafter. Illustratively, blood samples could be collected at 15, 30, 60 and 120 minutes after administration, and then every hour from 2 to 10 hours after administration. Additional blood samples may also be taken later, for example at 12 and 24 hours after administration. If the same subjects are to be used for study of a second test formulation, a period of at least 7 days should elapse before administration of the second formulation. Plasma is separated from the blood samples by centrifugation and the separated plasma is analyzed for ganaxolone by a validated high performance liquid chromatography/tandem weight spectrometry (LC/APCI-MS/MS) procedure such as, for example, Ramu et al., Journal of Chromatography B, 751 (2001) 49-59).

Plasma concentrations of ganaxolone referenced herein are intended to mean total ganaxolone concentrations including both free and bound ganaxolone. Any formulation giving the desired pharmacokinetic profile is suitable for administration according to the present methods. Exemplary types of formulations giving such profiles are liquid dispersions and solid dose forms of the ganaxolone formulation described herein. Aqueous dispersions of ganaxolone are stable at temperatures from 4° C. up to 40° C. for at least 3 months.

EXAMPLES

This invention is further illustrated by the following examples that should not be construed as limiting. Those of skill in the art of pharmaceutical formulation will readily appreciate that certain modifications to the examples described herein may be needed, particularly for changes in formulation batch size. Any methods, materials, or excipients which are not particularly described will be generally known and available those skilled in the drug design and assay and pharmacokinetic analysis. The particle size data, for examples in which a ganaxolone particle size is reported, were obtained using a Horiba LA-910 Laser Light Scattering Particle Size analyzer (Horiba Instruments, Irvine, Calif.) and reported as volume weighted median (D50). Studies of ganaxolone particles in liquids, beads, powders and immediate release dosage forms in SGF and SIF are performed by dispersing an appropriate amount of the ganaxolone formulation into 20 mL of SGF or SIF in a vial to obtain a measuring concentration of ganaxolone of about 0.5 mg/mL. For example, in one embodiment, 200 mg of a ganaxolone suspension formulation containing 5 wt % of ganaxolone and appropriate levels of HPMC, PVA, SLS, and preservatives was dispersed into 20 mL of SGF or SIF in a vial for measurement. The vial is immersed in an oil bath kept at 36 to 38° C. for 3 h. The sample is assessed visually for signs of flocculation and particle size is measured on a Horiba LA-910 to obtain D50 values.

Abbreviations

The following abbreviations are used in the examples below. Other abbreviations used in the examples will be understood by those of skill in the art of pharmaceutical formulations.

| | |
|---|---|
| GNX | Ganaxolone |
| HDPE | High Density Polyethylene |
| HPMC | Hydroxypropylmethylcellulose |
| PVA | Polyvinyl alcohol |
| SLS | Sodium Lauryl Sulfate |
| DOSS | Sodium docusate |
| SGF | Simulated gastric fluid |
| SIF | Simulated intestinal fluid |
| WT | Weight |

Example 1

The purpose of this example is to describe the preparation of an aqueous dispersion of ganaxolone comprising particles having an effective particle size of less than 500 nm.

Crystalline ganaxolone is premixed with polyvinylpyrrolidinone/vinyl acetate (S-630), and sodium lauryl sulfate at concentrations of 30%, 10%, and 0.1% (weight/weight of milling slurry) in deionized water, respectively, and milled under high energy milling conditions (Dyno®-Mill (Willy Bachofen AG)) water jacketed with a grinding media consisting of $ZrO_2$ having a size ranging 0.4 to 0.6 mm. The crystalline ganaxolone is milled with the grinding media for a total of 1 hour. The milling temperature is not allowed to exceed 50° C. The milling concentration is about 30% ganaxolone by weight vs. the milling media. The milling media contains about 10% weight/volume of the PVP/VA(S-630) and 0.1% SLS. The resulting blended ganaxolone dispersion is separated from the grinding media by filtration through a 5 micron filter to yield a ganaxolone dispersion which can then be evaluated for performance in animal pharmacokinetics. Liquid aqueous dispersions are formulated by diluting the milled dispersion with deionized water to a final concentration of 50 mg/ml after the addition of sucrose, methyl and propylparaben and artificial strawberry flavoring (0.005% volume/volume).

Example 2

The purpose of this example is to describe the preparation of an aqueous dispersion of ganaxolone comprising particles having an effective particle size of about 150 nm.

Crystalline ganaxolone is premixed with polyvinylpyrrolidinone/vinyl acetate (S-630), and dioctyl sodium sulfosuccinate at concentrations of 30%, 2.5%, and 0.05% (weight/weight) in deionized water, respectively, and milled under high energy milling conditions (Dyno®-Mill (Willy Bachofen AG)) water jacketed with a grinding media consisting of zirconium oxide beads having a size ranging 0.1 to 0.2 mm. The crystalline ganaxolone is milled with the grinding media for a total of 1 hour. The milling temperature is not allowed to exceed 50° C. The milling concentration is about 30% ganaxolone by weight vs. the milling media. The milling media contains about 10% weight/weight of the PVP/VA(S-630) and 0.05% DOSS (weight/weight) and deionized water. The resulting blended ganaxolone dispersion is separated from the grinding media by filtration through a 5 micron to yield a ganaxolone dispersion which can then be evaluated for performance in animal pharmacokinetics. Liquid aqueous dispersions are formulated by diluting the milled dispersion with deionized water to a final concentration of 50 mg/ml after the addition of sucrose, methyl and propylparaben and artificial strawberry flavoring (0.01% volume/volume).

Example 3

The purpose of this example is to describe the preparation of an aqueous dispersion of ganaxolone comprising particles having an effective particle size of about 150 nm.

Crystalline ganaxolone is premixed with hydroxypropylmethylcellulose, and DOSS at concentrations of 25%, 10%, and 0.3% (weight/weight) in deionized water, respectively (in alternative methods, the HPMC can be in a range from about 0.5% to 5% or 1.5% to 3%), and milled under high energy milling conditions (Dyno®-Mill (Willy Bachofen AG)) water jacketed with a grinding media consisting of zirconium oxide beads having a size ranging 0.1 to 0.2 mm. The crystalline ganaxolone is milled with the grinding media for a total of 1 hour. The milling temperature is not allowed to exceed 50° C. The milling concentration is about 25% ganaxolone by weight vs. the grinding media. The grinding media consists of 0.1 to 0.2 mm $ZrO_2$ beads filling 85% of the grinding vessel volume (volume/volume). The resulting blended ganaxolone dispersion is separated from the grinding media by filtration through a 5 micron filter to yield a ganaxolone dispersion which can then be evaluated for performance in animal pharmacokinetics. Liquid aqueous dispersions are formulated by diluting the milled dispersion with deionized water Containing 2% HPMC and 0.1% SLS (Weight/Weight) to a final concentration of 20 mg/ml for animal testing. A suitable dispersion for human use would require the addition of sucrose, methyl and propylparaben and artificial strawberry flavoring (0.005% volume/volume).

Example 4

The purpose of this example is to describe the preparation of an aqueous dispersion of ganaxolone comprising particles having an effective particle size of about 100 nm.

Crystalline ganaxolone is premixed with hydroxypropylmethylcellulose, and sodium lauryl sulfate at concentrations of 25%, 2%, and 0.1% (weight/weight) in deionized water, respectively (in alternative methods, the HPMC can be in a range from about 0.5% to 10% or 1.5% to 3%), and milled under high energy milling conditions (Dyno®-Mill (Willy Bachofen AG)) water jacketed with a grinding media consisting of zirconium oxide beads having a size ranging 0.1 to 0.2 mm. The crystalline ganaxolone is milled with the grinding media for a total of 2 hours at 15 meters/sec ejection velocity. The milling temperature is not allowed to exceed 50° C. The milling concentration is about 25% ganaxolone by weight vs. the milling media. The milling media contains about 2% weight/weight of the HPMC and 0.1% SLS (w/w) in deionized water. The resulting blended ganaxolone dispersion is separated from the grinding media by filtration through a 5 micron filter to yield a ganaxolone dispersion which can then be evaluated for performance in animal pharmacokinetics by diluting with distilled water containing 2% HPMC and 2.5% sucrose (w/w) to a final concentration of 20 mg/ml).

Example 5

In Example 5, ganaxolone particles with an effective particles size under 500 nm were obtained utilizing the parameters of Example 1 utilizing 30% ganaxolone, 10% polyvinylpyrrollidinone/vinyl acetate, 0.3% DOSS, 0.1 to 0.2 mm $ZrO_2$ beads at 85% volume with a milling residence time of about 30 minutes.

Example 6

In Example 6, ganaxolone particles with an effective particles size under 500 nm were obtained utilizing the parameters of Example 1 utilizing 30% ganaxolone, 10% HPMC, 0.3% DOSS, 0.1 to 0.2 mm $ZrO_2$ beads at 85% volume with a milling residence time of about 30 minutes.

Example 7

In Example 7, ganaxolone particles with an effective particles size under 200 nm were obtained utilizing the parameters of Example 1 utilizing 30% ganaxolone, 2% HPMC, 0.1% SLS, 0.1 to 0.2 mm $ZrO_2$ beads at 80% volume with a milling residence time of about 2 hours.

Example 8

In Example 8, ganaxolone particles with an effective particles size under 250 nm were obtained utilizing the parameters of Example 1 utilizing 30% ganaxolone, 10% polyvinylpyrrollidinone/vinyl acetate, 0.1% SLS, 0.4 to 0.6 mm glass beads at 85% volume with a milling residence time of about 1 hour.

Example 9

The dispersion from a previous example, before addition of flavoring/sweeteners/preservatives is sprayed in a fluidized bed granulator (e.g. Wurster column) maintaining a bed temperature of 80° C. onto sucrose spherical beads of about 50 um diameter. The ganaxolone composition is sprayed at a level of about 30-40% weight to bead weight and is dried. These ganaxolone microparticulate beads can be filled into gelatin capsules for an immediate release formulation or some of the beads may be re-introduced into the granulator and an Eudragit L30 D 55 dispersion is applied with spray guns facing downward to a 0.5% coating level (weight/weight). These coated beads can now be used with the uncoated beads in a automatic capsule filler at a 40%/60% ratio (uncoated/coated) to provide a 300 mg Ganaxolone dose in a total weight of about 800 mg.

Example 10

Dissolution Testing for Ganaxolone Formulations

Generally, all experiments are conducted at 36° C. to 38° C. The dissolution medium preferably is SGF or SIF containing 10% of sodium lauryl sulfate (SLS). The volume of the medium is 900 mL. The operating speeds are 75 rpm for Apparatus 1 (basket) and 50 rpm for Apparatus 2 (paddle) for solid-oral dosage forms and 25 rpm for suspensions. A 40-mesh screen is used in almost all baskets, but other mesh sizes may be used when the need is documented by supporting data.

Apparatus 2 is generally preferred for tablets. Apparatus 1 is generally preferred for capsules and for dosage forms that tend to float or that disintegrate slowly. A sinker, such as a few turns of platinum wire, may be used to prevent a capsule from floating.

The test time is generally 30 to 60 minutes, with a single time point specification for pharmacopeia purposes. To allow for typical disintegration times, test times of less than 30 minutes are to be based on demonstrated need. Dissolution test times and specifications usually are established on the basis of an evaluation of dissolution profile data. Typical specifications for the amount of active ingredient dissolved, expressed as a percentage of the labeled content (Q), are in the range of 70% to 80% Q dissolved. A Q value in excess of 80% is not generally used, as allowance needs to be made for assay and content uniformity ranges.

For an oral dispersion, add 20 ml or a volume equivalent to 1000 mg ganaxolone to each Type II vessel at 75 RPM paddle speed containing 500 mL SGF containing 10% SLS at 36 to 38° C. and at 45 minutes obtain a 5 ml sample via syringe. Filter 3 ml from each container through a syringe fitted filter disk (0.05 micron) into an eppendorf type centrifuge tube and centrifuge at 10000 RPM for 30 minutes. Carefully pipette 2 ml of supernatant from the tube into a 10 ml volumetric flask. Dilute to 10 ml with methanol and stopper and invert at least 5 times.

Analyze a sample from each volumetric in duplicate with a validated HPLC assay as follows:
Column: Waters, SunFire, 250×4.6 mm, 5 um
Mobile phase: ACN/MeOH/water=65/5/30 (v/v)
Flow rate: 1.0 ml/min
Detection: RI
Sample conc.: 0.1 to 0.4 mg/ml mg/ml in MeOH
Run time: 45 min
Injection volume: 50 ul
Ganaxolone: RT~20 min
Make a standard solution of ganaxolone at 1 mg/ml in methanol and dilute to 0.5, 0.25 and 0.125 mg/ml in methanol and inject 50 μl of each concentration before and after each duplicate run. Plot the results against the standard curve to determine the % ganaxolone dissolved. For a pulsatile or delayed release solid dosage form, the general method is similar except that 10% SLS in SGF is used initially (first hour) and then the media is replaced with SIF containing 10% SLS and another dissolution period is evaluated (3 hours). Using USP intestinal fluid adjusted to pH 6.8, approximately 70% of the weight of the enteric coated Ganaxolone particles will be released within 3 hours at 75 RPM paddle speed.
For drug release profiles for Ganaxolone formulations, see Example 29.

Example 11

Purpose-bred Beagle dogs are obtained and housed in a USDA-approved facility in accordance with AAALAC guidelines. Expected dog weights are from 8 to 12.0 kg at the beginning of the evaluation, and are weighed prior to each period of the study. Animals are block randomized into groups of 3 per treatment. Each study will test ganaxolone formulations (as described in Examples 1-3) along with a reference group which is administered a conventional ganaxolone-α-cyclodextrin formulation (reference formulation). Fasted animals are fasted overnight without water prior to each study day. Designated fed dogs are fed a can (about 400 gm) of Alpo "Chunky with Beef for Dogs," which has 55% of total calories from fat, approximately 45 minutes prior to dosing. When administering aqueous dispersions, test ganaxolone aqueous dispersion formulations and ganaxolone reference formulations are diluted with deionized water within 2 hours of dosing to deliver about 10 mg/kg ganaxolone in a volume of 2.0 ml/kg. If the liquid suspension is to be administered without dilution, a dose of 5 to 10 mg/kg is given via oral gavage followed by a 7.5 to 10 ml/kg water flush. When administering ganaxolone capsules, both test capsule and reference capsules are given in a dose of about 10 mg/kg. Capsules are administered orally as is typical. Standard laboratory chow and water are offered ad libitum 4 h after dosing. To eliminate the variability of drug absorption among the dogs, all studies should be conducted in a randomized crossover design. Approximately 2 milliliters of blood sample are withdrawn with a 21G needle and via direct venipuncture sampling at predose, 15 min, 30 min, 1 h, 2 h, 4 h, 6 h, 8 h, 10 h, 24 h and 48 h. Blood is immediately transferred to a potassium EDTA blood collection tube (VACUTAINER, Becton Dickinson, Franklin Lakes, N.J., USA) and is stored on ice until the samples are centrifuged at 2500-4000 rpm for 15 min. The plasma is transferred to polypropylene tubes, and samples are stored at −70° C. until analyzed by liquid chromatography/tandem weight spectrometry (LC/MS/MS).

A validated method using liquid chromatography/atmospheric pressure chemical ionization tandem weight spectrometry (LC/APCI-MS/MS) for the determination of ganaxolone in dog plasma is used for the analysis of the all samples. This method is conducted in accordance with the validated method previously published (Ramu et al Journal of Chromatography B, 751 (2001) 49-59).

Example 12

PK Data Processing

WinNonlin v. 3.1 (Scientific Consulting, Inc., Apex, N.C.) is used for non-compartmental analysis of the data. Area under the plasma concentration-time curve ($AUC_{0-72\ h}$) is calculated from observed plasma concentrations from 0 to 72 h. Any plasma concentrations below the limit of quantitation are set equal to zero. Geometric and arithmetic mean and geometric standard error of the mean (S.E.M.) of AUC, observed maximum plasma concentration ($Cm_{ax}$), and time of $C_{max}$ ($T_{max}$) can be calculated with Microsoft Excel. Treatment and animal effects on the AUC values and observed $C_{max}$ are determined with the statistical programs of SAS (SAS Institute, Inc., Cary, N.C., USA). Also, an interaction model with dog, formulation, and fed/fasted state is examined to confirm the interaction of food with formulation. The AUC and $C_{max}$ values are log-transformed to normalize the distributions. The Wilcoxon matched-pairs signed ranks test is used to evaluate differences in $T_{max}$ values between groups. Differences are only considered significant at $p \leq 0.05$.

Example 13

Ganaxolone Sub-Micron Particle Suspensions

Ganaxolone submicron particle suspension formulations comprising HPMC, SLS and PVA as stabilizers show useful stability profiles under storage conditions. Submicron particle formulations containing 5 wt % ganaxolone based on the total weight of the formulation and varying amounts of HPMC, SLS and PVA were stored at ambient temperature for 7 months. Visual assessments were made with regard to appearance of these formulations. The results are shown in Table 2.

TABLE 2

Non-preserved ganaxolone particle formulations containing HPMC, SLS and PVA

| Entry | HPMC (wt %) | SLS (wt %) | PVA (wt %) | Visual Assessment after 7 Months |
|---|---|---|---|---|
| 1 | 2 | 0.2 | 1 | white suspension, trace amount of solid on bottom |
| 2 | 2 | 0.2 | 1.5 | white suspension, small amount solid at bottom |
| 3 | 2 | 0.2 | 2 | white suspension, small amount of solid at bottom |
| 4 | 2 | 0.2 | 2.5 | white suspension, some solid at bottom |
| 5 | 2 | 0.2 | 3 | settled, partially clear liquid on top |
| 6 | 2 | 0.2 | 3.5 | settled, near clear liquid on top |
| 7 | 2 | 0.2 | 4 | settled, clear liquid on top |
| 8 | 5 | 0.3 | 1 | white suspension, no apparent settling |
| 9 | 5 | 0.3 | 1.5 | white suspension, small amount of solid at bottom |
| 10 | 5 | 0.3 | 2 | white suspension, some solid at bottom |
| 11 | 5 | 0.3 | 2.5 | white suspension, some solid at bottom |
| 12 | 5 | 0.3 | 3 | two layers, partially clear layer on top |
| 13 | 5 | 0.3 | 3.5 | settled, clear liquid on top |
| 14 | 5 | 0.3 | 4 | settled, clear liquid on top |
| 15 | 5 | 0.2 | 1 | white suspension, no apparent settling |
| 16 | 2.5 | 0.2 | 1.25 | white suspension, no apparent settling |

Example 14

Physical Stability in Gastric and Intestinal Fluids

Physical stability of ganaxolone particle suspension formulations in simulated gastric and intestinal fluids were tested at 36-38° C. unstirred unless otherwise specified.

Ganaxolone suspension formulations containing HPMC and a surfactant such as SLS or sodium docusate or DOSS, prepared as described in Example 39 underwent flocculation in SGF and SIF. Test results for two formulations, Ex-39F (15% GNX, 7.5% HPMC and 0.3% SLS) and Ex-39E (15% GNX, 2.5% HPMC and 0.1% DOSS) are shown in Table 3. The particle size growth occurred primarily in the first 1 to 1.5 h after the SGF or SIF treatment, as the D50 values reached micron levels after 90 min (entries 2 and 3, Table 3). It is interesting to note that these formulations are quite stable in deionized water (entries 1 and 5).

TABLE 3

Stability of ganaxolone particle formulations containing only HPMC and SLS or DOSS in various fluids (initial D50: 106 nm) at 36° C. to 38° C.

| Entry | Formulation | Testing Conditions | D50 |
|---|---|---|---|
| 1 | Ex-39F | Water, 90 min | 148 nm |
| 2 | Ex-39F | SIF, 90 min | 1.341 um |
| 3 | Ex-39F | SGF, 90 min | 1.722 um |
| 4 | Ex-39F | Water, 3 h | 124 nm |
| 5 | Ex-39F | SIF, 3 h | 2.581 um |
| 6 | Ex-39F | SGF, 3 h | 1.787 um |
| 7 | Ex-39E | SGF, 100 min | 1.382 um |
| 8 | Ex-39F | 0.2N NaCl solution, 90 min | 1.349 um |

Example 15

Ganaxolone Suspension Formulations Containing Polyvinyl Alcohol (PVA)

The stabilization effect of PVA is demonstrated by formulation Ex-40A. This formulation was prepared by diluting the final milling slurry as described in Example 40 (Ex-40) with a diluent containing appropriate amounts of HPMC, PVA and SLS (Table 4, entries 1 and 2) in deionized water. After 3 h, the D50 values grew only about 19 nm from an initial of 142 nm. As a comparison, the milling slurry Ex-40 which does not contain PVA underwent flocculation under the same conditions with the D50 value increasing to 360 nm in SIF and 699 nm in SGF from the same initial value of 142 nm (entries 4-5). Further, formulation Ex-49A, having nearly identical composition to those of formulation Ex-40A except containing no PVA, showed a D50 value of 300 nm after 3 h in simulated gastric fluid, an increase of 176 nm from the initial D50 of 124 nm (entry 4).

TABLE 4[1]

Effect of PVA on Ganaxolone Suspension Stability in SGF and SIF

| Entry | Formulation | GNX % | HPMC % | SLS % | PVA % | D50 (nm) | Test Conditions |
|---|---|---|---|---|---|---|---|
| 1 | Ex-40A | 5 | 5 | 0.3 | 1 | 161 | SGF, 3 h |
| 2 | Ex-40A | 5 | 5 | 0.3 | 1 | 157 | SIF, 3 h |
| 3 | Ex-49A | 5 | 5 | 0.1 | 0 | 300 | SGF, 3 h |
| 4 | Ex-40 | 25 | 2 | 0.1 | 0 | 699 | SGF, 3 h |
| 5 | EX-40 | 25 | 2 | 0.1 | 0 | 360 | SIF, 3 h |

[1]Percentages based on w %/total formulation wt and condition include storage at 36° C. to 38° C. without stirring Example 16

Effect of Ganaxolone/HPMC Ratio on Ganaxolone Suspension Formulation Stability in SGF and SIF Ganaxolone to HPMC ratio is important to ganaxolone suspension formulation stability in SGF and SIF. Ganaxolone suspension formulations containing 15 wt % ganaxolone, 3 wt % HPMC, 1 wt % PVA, 0.1 wt % methylparaben, 0.02 wt % propylparaben, and 0.05-0.2 wt % SLS in deionized water showed increase in D50 value of 155 to 261 nm in SGF (entries 2-3, Table 5) after 2 h. The increase in D50 does not correlate with the concentrations of SLS. Diluting these formulations with additional HPMC to 5 wt % ganaxolone and 5 wt % HPMC while keeping other components constant resulted in particle size growth of only <28 nm in 70 min (entries 5-11 and 13, Table 5). As shown in Table 2, the particle size growth primarily occurred during the first 1 to 1.5 h of treatment. Thus these formulations were significantly more stable in SGF than those having larger ganaxolone to HPMC ratios. Increasing HPMC level to 8.5% provided little additional stabilization benefit. The data also showed that the exact level of SLS in these formulations had little impact on gastrointestinal stability.

Formulations in entries 14-16 of Table 5 had 0.2% methylparaben and had similar stability performance in SGF and SIF.

TABLE 5

Gastric and Intestinal Stabilities of Ganaxolone Particles

| Entry | GNX wt % | HPMC wt % | SLS wt % | Methyl Paraben wt % | Propyl Paraben wt % | PVA wt % | D50 (nm) | Test Conditions[1] |
|---|---|---|---|---|---|---|---|---|
| 1 | 5 | 3 | 0.05 | 0.1 | 0.02 | 1 | 171 | Initial |
| 2 | 15 | 3 | 0.05 | 0.1 | 0.02 | 1 | 331 | SGF, 2 h |
| 3 | 15 | 3 | 0.1 | 0.1 | 0.02 | 1 | 326 | SGF, 2 h |
| 4 | 15 | 3 | 0.2 | 0.1 | 0.02 | 1 | 432 | SGF, 2 h |
| 5 | 5 | 5 | 0.2 | 0.1 | 0.02 | 1 | 180 | initial |
| 6 | 5 | 5 | 0.2 | 0.1 | 0.02 | 1 | 182 | SGF, 70 min |
| 7 | 5 | 5 | 0.2 | 0.1 | 0.02 | 1 | 190 | SIF, 70 min |
| 8 | 5 | 5 | 0.1 | 0.1 | 0.02 | 1 | 209 | SGF, 70 min |
| 9 | 5 | 5 | 0.05 | 0.1 | 0.02 | 1 | 204 | SGF, 70 min |
| 10 | 5 | 5 | 0.025 | 0.1 | 0.02 | 1 | 207 | SGF, 70 min |
| 11 | 5 | 5 | 0.017 | 0.1 | 0.02 | 1 | 203 | SGF, 70 min |
| 12 | 5 | 8.5 | 0.017 | 0.1 | 0.02 | 1 | 201 | SGF, 70 min |
| 13 | 5 | 5 | 0.025 | 0.1 | 0.02 | 2 | 202 | SGF, 70 min |
| 14 | 5 | 5 | 0.017 | 0.2 | 0.02 | 1 | 185 | Initial |
| 15 | 5 | 5 | 0.017 | 0.2 | 0.02 | 1 | 209 | SGF, 3 h |
| 16 | 5 | 5 | 0.017 | 0.2 | 0.02 | 1 | 213 | SIF, 3 h |

[1]Test temperature is the same as that described in Example 14.

Example 17

Formulations Containing Sodium Benzoate as Preservatives

Ganaxolone suspension formulations containing sodium benzoate as preservatives with citric acid/sodium citrate (pH 4.0) as buffering agents were also evaluated. With 0.17 wt % sodium benzoate, 0.13 wt % citric acid and 0.01 wt % sodium citrate added, two formulations containing of 5 wt % ganaxolone, 5 wt % HPMC, 1 wt % PVA, and 0.1 wt % SLS in deionized water with initial D50 values of 196 and 321 nm respectively showed good stability against flocculation in both SGF and SIF (Table 6).

TABLE 6

SGF and SIF stabilities of ganaxolone suspension formulations containing sodium benzoate as preservatives

| Entry | citric acid, wt % | Sodium benzoate, wt % | Sodium Citrate, wt % | D50 (nm) no sonication/1 min sonication | Testing Conditions[1] |
|---|---|---|---|---|---|
| 1 | 0.13 | 0.17 | 0.01 | 196/176 | Initial |
| 2 | 0.13 | 0.17 | 0.01 | 222/191 | SGF, 3 h |
| 3 | 0.13 | 0.17 | 0.01 | 248/201 | SIF, 3 h |
| 4 | 0.13 | 0.17 | 0.01 | 321/314 | Initial |
| 5 | 0.13 | 0.17 | 0.01 | 327/320 | SGF, 3 h |
| 6 | 0.13 | 0.17 | 0.01 | 328/321 | SIF, 3 h |

[1]Test temperature is the same as that described in Example 14.

Example 18

Effect of PVA on Cmax

The addition of PVA to ganaxolone suspension formulations reduces the $C_{max}$ levels. $C_{max}$ levels were determined for ganaxolone suspension formulations containing 1:1 GNX/HPMC (wt %), SLS (0.2-0.4% SLS/GNX), and with and without PVA (20% PVA/GNX). Particles of 110 nm, 140 nm, and 320 nm were orally administered into beagle dogs at a dose of 5 mg/kg under fed and fasted conditions. The pharmacokinetics results are shown in Table 7. The formulation with no PVA (Ex-18A) achieved higher exposure than those with PVA (Ex-18B and Ex-18C). However, addition of PVA reduced variability between the fed and fasted states especially for the AUC values. The ratio of $C_{max}$ to AUC was also lower with PVA added. Formulation Ex-18C is identical to Ex-18B except for added preservatives (0.1 wt % MP, 0.02 wt % PP and 0.09 wt % sodium benzoate at pH 4) and particle size is larger due to the presence of the preservative. It is surprisingly found that the Ex-18C formulation had higher exposure than Ex-18B formulation despite that the particle size (D50) of Ex-18C is more than double those of Ex-18B (320 nm vs. 140 nm). The Ex-18C formulation shows even less variability as well as enhanced total exposure as compared to the smaller particle size formulation (Ex-18A). The food effect is slightly greater in the optimized suspension due to prolonged drug absorption due to larger particle size.

TABLE 7

Comparative PK results in beagle dogs for ganaxolone suspension formulations with and without PVA at comparable dose levels (5 mg/kg)

| Formulation Reference | Particle Size (D50) | PVA/Preservative | $C_{max}$ (ng/mL) | $AUC_{0-72\,hr}$ (ng*h/mL) | Food Intake |
|---|---|---|---|---|---|
| Ex-18A | 110 nm | None/None | 448 ± 96 | 2422 ± 1059 | Fasted |
| Ex-18A | 110 nm | None/None | 1194 ± 104 | 4637 ± 2600 | Fed |
| Ex-18B | 140 nm | Yes/None | 268 ± 36 | 1643 ± 295 | Fasted |
| Ex-18B | 140 nm | Yes/None | 640 ± 92 | 3525 ± 1190 | Fed |
| Ex-18C | 320 nm | Yes/Yes | 243 ± 40 | 1855 ± 321 | Fasted |
| Ex-18C | 320 nm | Yes/Yes | 642 ± 40 | 5512 ± 681 | Fed |

Data provided in Table 8 further demonstrates the reduced variability between fed and fasted state for ganaxolone formulations containing PVA. The Ex-18D formulation has a particle size of 120 nm, which is very similar to that of Ex-18A above. This formulation was identical to EX-18A except PVA was added. In this study, a fed/fasted effect of 1.6-1.7×$AUC_{0-72}$(fed): $AUC_{0-72}$(fasted) was obtained.

TABLE 8

| Group # | $AUC_{(0-72)}$ (ng*h/mL) MEAN | SD | $AUC_{inf}$ (ng*h/mL) MEAN | SD | $C_{max}$ (ng/mL) MEAN | SD |
|---|---|---|---|---|---|---|
| Formulation Ex-18D in Fasted Males | 1440 | 460 | 1616 | 474 | 273 | 45 |
| Formulation Ex-18D | 2403 | 422 | 2624 | 430 | 563 | 92 |

TABLE 8-continued

| Group # | $AUC_{0-72}$ hr (ng*h/mL) MEAN | SD | $AUC_{inf}$ (ng*h/mL) MEAN | SD | $C_{max}$ (ng/mL) MEAN | SD |
|---|---|---|---|---|---|---|
| Formulation Ex-18D in Fed Males | 2 | 2403 | 422 | 2624 | 430 | 563 | 192 |

Example 19

Use of Simethicone in the Milling Process

Presence of simethicone (e.g., at 0.1 wt % level) during the milling process results in more stable ganaxolone suspensions (i.e. the particles experienced less post-milling particle size growth compared to those produced without simethicone during the milling). The experimental results for two nearly identical milling runs except simethicone levels are shown in Table 9.

TABLE 9

| Milling Run | Size (g) | Ingredients (Concentrations) During Milling, wt % | Simethicone during milling, wt % | Residence Time (min) | D50 (end of milling) | D50 (fullycured) |
|---|---|---|---|---|---|---|
| Ex-42 | 1200 | ganaxolone(25%), HPMC(5%), SLS (0.1%), PVA (1%), methylparaben (0.1%), propylparaben (0.02%) | 0.1% | 27.5 | 180 | 327 |
| Ex-44 | 1200 | ganaxolone (25%), HPMC(3%), SLS (0.1%), PVA (1%), methylparaben (0.1%), propylparaben (0.02%) | 0 | 25.4 | 162 | 380 |

TABLE 8-continued

| Group # | $AUC_{(0-72)}$ (ng*h/mL) MEAN | SD | $AUC_{inf}$ (ng*h/mL) MEAN | SD | $C_{max}$ (ng/mL) MEAN | SD |
|---|---|---|---|---|---|---|
| in Fed Males | | | | | | |

Data provided in Table 8 further demonstrates the reduced variability between fed and fasted state for ganaxolone formulations containing PVA. The Ex-18D formulation has a particle size of 120 nm, which is very similar to that of Ex-18A above. This formulation was identical to EX-18A except PVA was added. In this study, a fed/fasted effect of 1.6-1.7 $AUC_{0-72}$(fed): $AUC_{0-72}$(fasted) was obtained.

TABLE 8

| Group # | $AUC_{0-72}$ hr (ng*h/mL) MEAN | SD | $AUC_{inf}$ (ng*h/mL) MEAN | SD | $C_{max}$ (ng/mL) MEAN | SD |
|---|---|---|---|---|---|---|
| Formulation Ex-18D in Fasted Males | 1 | 1440 | 460 | 1616 | 474 | 273 | 45 |

Example 20

Control of Particle Size by Adjusting the Residence Time of Milling

Milling runs in deionized water are conducted with 1 wt % PVA and appropriate amounts of preservatives in addition to HPMC (3 to 5 wt %) and SLS (0.05 to 0.1 wt %) utilizing 0.1-0.2 mm zirconium oxide beads (entries 1-4, Table 3). Each wt % is based on the total weight of the milling mixture (without zirconium oxide beads). For entries 1, 3, and 4, the preservatives were 0.1 wt % methylparaben and 0.02 wt % propylparaben and for entry 5, the preservative was 0.1 wt % sodium benzoate buffered with 0.12 wt % citric acid and 0.0093 wt % sodium citrate. After the effective particle size (D50 reached between 150-170 nm, runs 2 and 3 were stopped, while run 1 was allowed to continue. Data suggests that continued milling did not reduce the particle size any further. However, it did produce more stable particles compared to the runs with shorter residence time. Further, after run 3 was re-milled two days later (D50 303 nm) under the same conditions for additional 69 min of residence time (entry 5), the particles became even more stable.

Milling runs were also conducted with only HPMC and SLS. PVA and preservatives were added post-milling (entries 5-9, Table 10). As in the case of run 1, longer residence time resulted in more stable particles.

TABLE 10

Post-Milling Particle Size Growth vs. Residence Time

| Milling Run | D50 at end of milling (nm)[e] | Residence Time (min) | Increase in D50 4 weeks after milling (nm) |
|---|---|---|---|
| 1[a] | 153 | 75 | 39 |
| 2[b] | 160 | 25 | 201 |
| 3[c] | 162 | 25.4 | 209 |
| 4[d] | 167 | 69 | 23 |
| 5[f] | 143 | 33 | 177 |
| 6[f] | 139 | 35 | 156 |
| 7[f] | 155 | 34 | 160 |
| 8[f] | 163 | 24 | 217 |
| 9[f] | 142 | 68 | 52 |

[a]Ganaxolone concentration (15%), PVA (1%), methylparaben (0.1%) and propylparaben (0.02%) were present during milling;
[b]Ganaxolone concentration (25%), PVA (1%), sodium benzoate (0.1%), citric acid (0.12%), sodium citrate (0.0093%) and simethicone (0.025%) were present during milling;
[c]Ganaxolone concentration (25%), PVA (1%), methylparaben (0.1%), propylparaben (0.02%) were present during milling;
[d]Milling slurry of entry 3 (2x diluted) was re-milled after 2 days;
[e]Particle size was measured on a Horiba LA-910 particle size analyzer;
[f]PVA (1%), methylparaben (0.1%), propylparaben (0.02%) were added post-milling.

Example 21

Preparation of Pharmaceutically Useful Ganaxolone Suspension Formulations (50 mg/mL) from the Milling Slurry Method A (one-step dilution): A milling slurry of known ganaxolone concentration prepared as described in Examples 37-52 is diluted with appropriate amount of diluent containing appropriate levels of excipients and other necessary components such as preservatives, flavoring, sweetener and antifoaming agent to achieve 50 mg/mL drug concentration.

Method B (two-step dilution): A milling slurry prepared as described in Examples 37-52 is first diluted to an intermediate drug concentration (ca. 80 mg/mL) with appropriate amount of diluent containing appropriate levels of excipients and all necessary components such as preservatives, flavoring and sweetener, antifoaming agent. For example, for a milling slurry with an initial ganaxolone concentration of 25 wt % is diluted by mixing one part of the milling slurry with two parts of the diluent will give the intermediate concentration of 8 wt % which is roughly equivalent to 80 mg/mL (assuming the density of the slurry is about 1 g/mL). The appropriate concentrations of excipients and other components are chosen for the diluent so that all components are present at the desired levels after the intermediate dilution. The precise ganaxolone concentration is then determined by appropriate assay (e.g. HPLC). The final dilution is performed with appropriate amount of diluent containing the correct levels of all excipients and other components.

Example 22

Effect of HPMC, SLS, and PVA Levels on Paraben-Containing Ganaxolone Suspension Formulations The effect HPMC, SLS, and PVA levels on the stability of paraben-containing ganaxolone particle formulations was studied. Each of the aqueous suspension formulations contains 5 wt % ganaxolone, 0.1 wt % methylparaben, 0.02 wt % propylparaben, each based on the total weight of the formulation, and varying amounts of HPMC, SLS and PVA in deionized water. Visual Assessments were conducted after 7 months of storage at ambient temperature to assess the formulation stability. The compositions and the stability results are shown in Table 11.

TABLE 11

Paraben-containing ganaxolone suspension formulations containing HPMC, SLS and PVA

| Entry | HPMC (wt %) | SLS (wt %) | PVA (wt %) | Visual Assessment after 7 Months |
|---|---|---|---|---|
| 1 | 2 | 0.1 | 3.5 | settled, partially clear liquid on top |
| 2 | 5 | 0.3 | 1 | white suspension, small amount of solid at bottom |
| 3 | 5 | 0.3 | 1.5 | white suspension, some solid at bottom |
| 4 | 5 | 0.3 | 2 | white suspension, some solid at bottom |
| 5 | 5 | 0.3 | 2.5 | white suspension, some solid at bottom |
| 6 | 5 | 0.3 | 3 | white suspension, small partially clear layer on top |
| 7 | 5 | 0.3 | 3.5 | settled, clear liquid on top |
| 8 | 5 | 0.3 | 4 | settled, clear liquid on top |
| 9 | 3 | 0.2 | 1 | white suspension, some solid on bottom |
| 10 | 3 | 0.2 | 1.5 | white suspension, substantial solid on bottom |
| 11 | 3 | 0.2 | 2 | white suspension, substantial solid on bottom |
| 12 | 3 | 0.2 | 2.5 | settled, partially clear liquid on top |
| 13 | 3 | 0.2 | 3 | settled, partially clear liquid on top |
| 14 | 3 | 0.2 | 3.5 | settled, near clear liquid on top |
| 15 | 3 | 0.2 | 4 | settled, clear liquid on top |

The data of Table 11 shows that 5 wt % HPMC 0.3 wt % SLS at 0.3 wt % ganaxolone formulations showed good stability with the amount 1 wt % to 3 wt % PVA range (entries 2-6). When PVA levels are further increased to 3.5 to 4 wt % while the other components are held constant, some settlement of particles at the bottom and clear liquid on the top of the formulations was observed (entries 7 & 8).

Formulations listed in entries 9-11 showed good stability with the amount of PVA ranging from 1 wt % to 2 wt % while the amounts of HPMC (3 wt %) and SLS (0.2 wt %) were held constant. When the PVA level increased to 2.5 to 4 wt % while the other components were held constant some settlement of particles at the bottom and clear liquid on the top of the formulations (entries 12-15) was observed.

There appears to be an optimal compositional range for obtaining good formulation stability. Less than or equal to 3.5 wt % of PVA (or 0.5 to 2.5 wt %) is desirable in obtaining good stability of paraben containing ganaxolone formulations, especially at 5 wt % (or 3 wt %) or lower HPMC concentrations.

Example 23

Effect of Preservative on Ganaxolone Suspension Formulation Stability in SGF and SIF The effect of a preservative on ganaxolone suspension formulation stability in SGF and SIF were studied. Formulations listed in entries 1-6, Table 12A contained 8-9.5 wt % of GNX, 4-4.8 wt % of HPMC, 0.24-0.29 wt % SLS, 6-7 wt % of sucrose, based on the total weight of the formulation. Various amounts of parabens as shown in Table 12A were added immediately prior to dispersion and storage in SGF and SIF at 36-38° C.

It can be seen from Table 12A that parabens have a stabilizing effect on the ganaxolone particle formulations in SGF and SIF when added immediately prior to dispersion into these media. The median particle size (D50) grew to around 200-270 nm from the initial value of 106 nm. These results compared favorably to those of the base formulations (without paraben) whose D50 exceeded 1 micron after 90 minutes in SGF or SIF as shown in Table 2. Furthermore, one minute of sonication of the formulations after one-hour of storage reduces the particle sizes to around 141 to 147 nm.

Significantly, when parabens or sodium benzoate were added as complexing agents after milling and the ganaxolone particles were allowed to cure to reach the end pint where the particles become stable, dispersion and storage in SGF and SIF at 36-38° C. for 3 h caused virtually no increase in particle size (D50). The results are shown in Table 12B.

TABLE 12A

Effect of methylparaben and propylparaben on physical stability of ganaxolone suspension formulations (Initial D50 106 nm)

| Entry | Methyl-paraben wt % | Propyl-paraben wt % | D50 no sonication, nm (1 min sonication) | Test Conditions 36 to 38° C. |
|---|---|---|---|---|
| 1 | 0.07 | 0 | 251 (144) | SGF, 1 h |
| 2 | 0.07 | 0 | 187 (141) | SIF, 1 h |
| 3 | 0 | 0.014 | 269 (144) | SGF, 1 h |
| 4 | 0 | 0.014 | 191 (141) | SIF, 1 h |
| 5 | 0.1 | 0.02 | 218 (147) | SGF, 1 h |
| 6 | 0.1 | 0.02 | 208 (142) | SIF, 1 h |

TABLE 12B

Test results in SGF and SIF for cured ganaxolone particles complexed with a complexing agent[a]

| Entry | Complexing agent/amount (% w/w) | Initial D50 unsonicated (1 min sonication) | D50 no sonication, nm, after storage in SGF, 3 h (1 min sonication) | D50 no sonication, nm, after storage in SIF, 3 h (1 min sonication) |
|---|---|---|---|---|
| 1 | Methylparaben/0.1% Propylparaben/0.02% | 314 nm (311 nm) | 326 nm (313 nm) | 344 nm (330 nm) |
| 2 | Sodium benzoate/0.09% Citric acid/0.12% Sodium citrate/0.093% | 321 nm (314 nm) | 322 nm (312 nm) | 329 nm (313 nm) |

[a]The composition of the test formulation are: 5% ganaxolone, 5% HPMC, 0.1% SLS (all based on total weight of the formulation).

Example 24

The Synergistic Effect of Preservative and PVA in Combination on Physical Stability of Ganaxolone Suspension Formulations The synergistic effect of a preservative and PVA combination on ganaxolone suspension formulation physical stability was studied. All formulations contained 4.5-8 wt % GNX, 2.2-4 wt % HPMC, 0.09-0.24 wt % SLS, 4.5-9 wt % sucrose, based on the total weight of the formulation, and varying amounts of paraben and PVA as shown in Table 13.

TABLE 13

Synergistic effects of parabens and PVA on stabilizing ganaxolone suspension formulation in SGF and SIF (initial D50 120 nm)

| Entry | Methyl-paraben, wt % | Propyl-paraben wt % | PVA, wt % | D50, nm (1 min sonication) | Test Conditions[1] |
|---|---|---|---|---|---|
| 1 | 0.1 | 0.02 | 0 | 218 (147) | SGF, 1 h |
| 2 | 0.1 | 0.02 | 0 | 208 (142) | SIF, 1 h |
| 3 | 0.07 | 0.015 | 1.3 | 149 (139) | SGF, 1 h |
| 4 | 0.08 | 0.016 | 1.1 | 150 (138) | SIF, 1 h |

[1]Test temperature is the same as that described in Example 14.

Results in Table 13 indicate that ganaxolone suspension formulations containing both parabens and PVA showed additional physical stability in both simulated gastric (SGF) and intestinal (SIF) fluids. While the ganaxolone particle size in formulations containing only parabens grew more than 80 nm in 1 h in both gastric and intestinal fluid (Table 13, entries 1-2), those in formulations containing ca. 1% PVA in addition to the parabens grew only slightly (less than 30 nm) (entries 3-4). These results suggest synergies between parabens and PVA in stabilizing the ganaxolone particles in gastric and intestinal fluids. Furthermore, one minute of sonication of the formulations containing both parabens and PVA after one-hour of storage reduces the particle sizes to around 138 to 139 nm.

Example 25

Effects of Multiple Preservatives on Pharmacokinetics (PK)

In the following examples, the effect of the combination of parabens and sodium benzoate and/or benzoic acid on pharmacokinetics was studied, versus the effect of sodium benzoate and/or benzoic acid without parabens. The particle sizes for both formulations were similar (320 nm for Ex-18C and 360 nm for Ex-25A). Studies were conducted using both fasted and fed beagle dogs and the PK results are summarized in Table 14.

Results in Table 14 indicate that paraben/sodium benzoate/benzoic acid combined preserved ganaxolone suspension formulations provide a lower food effect (about 3 times) than sodium benzoate alone formulations (about 4 times) at 5 mg/kg. Moreover, the paraben/sodium benzoate/benzoic acid combined preserved formulation showed significant improvement in exposure variability as compared to the sodium benzoate only formulation.

TABLE 14

Comparative PK results in beagle dogs (5 mg/kg, fed/fasted) for ganaxolone particle formulations preserved with sodium benzoate only and sodium benzoate/parabens combination.

| Formulation | Preservatives | $C_{max}$ (ng/mL) | AUC0-72 hours (ng*h/mL) | Food Intake |
|---|---|---|---|---|
| Ex-25A | Sodium benzoate/benzoic acid | 267 ± 93 | 1551 ± 264 | Fasted |
| Ex-25A | Sodium benzoate/benzoic acid | 802 ± 157 | 6352 ± 2469 | Fed |
| Ex-18C | Parabens + sodium benzoate/benzoic acid | 243 ± 40 | 1855 ± 321 | Fasted |
| Ex-18C | Parabens + sodium benzoate/benzoic acid | 642 ± 40 | 5512 ± 681 | Fed |

For liquid formulations amounts of formulation components are given as weight percent of the total formulation weight (w %/w) unless otherwise indicated. For solid dosage forms formulation components are given as a percent of ganaxolone (w %/GNX). For example, in a solid dosage form, 100% HPMC indicates that the weight of HPMC in the formulation is equal to the weight of ganaxolone in the formulation.

Particle size measurements for liquid ganaxolone suspensions are made using a Horiba LA 910 Particle Size Analyzer adding liquid ganaxolone suspension via a 5 ml pipette into the Horiba chamber (containing approx. 125 ml distilled water that has been blanked) to achieve a tungsten light transmittance of 75 to 80%. Other settings are a recirculation setting of 4, stirring setting of 1, and relative refractive index of 115-010.

Example 26

Spray Layered Ganaxolone Formulation 100 g of a sphere (20-35 mesh) are added to a Glatt GPCG-3 fluidized bed with Wurster column insert (4 inch), inlet temperature of 50 to 60° C. and air temp of 30 to 50° C. (total air volume approx. 150-200 cubic cm/hr). A 17.6% total solids content slurry containing ganaxolone (197 nm, 71% of solids content), hydroxymethylpropylcellulose (Pharmacoat 603, 14.9% of solids), SLS (0.1% of solids), sucrose (13.4% of solids), and 30% simethicone emulsion (DC7-9245, 0.1% of solids) with total weight of sprayed suspension being 697 g (574 ml water), is sprayed (bottom spray) through 1.2 mm nozzles at 10 ml/min and 1.5 bar of pressure until a layering of 123% % is achieved as compared to initial bead weight.

Dispersion in water (1 g in 300 ml) at 36-38° C. spinning at 75 RPM demonstrated complete disintegration within 10 minutes. Dissolution of ganaxolone coated sugar beads into SGF or SIF at 0.5 mg/ml at 36-38° C. for 1 hour showed agglomeration (settling in container) and effective particle size of >5 um.

Example 27

Preparation of Dried Solid Ganaxolone Particle Formulations

Ganaxolone particle suspension (1.0 g), prepared as described above in Examples 37-52 is placed in a 25 ml glass scintillation vial fitted onto a Buchi rotary evaporator. The vial is spun at approx. 150 rpm and the water bath temperature is set between 70-90° C. Vacuum is gradually applied for the initial 2 minutes to minimize bumping. After bumping is no longer a problem, full vacuum is applied (approx. 2-4 mbar) until a powder free of any water or visible condensation is observed (approx. 10 min). The vial is then dried on the evaporator for an additional 10-15 minutes.

In cases where additional components are required to be added to the ganaxolone particle suspension prior to drying, these components are weighed into the vial first and approx. 0.5 g of deionized water is added to obtain a complete solution. To this solution is then added 1.0 g of the ganaxolone particle suspension. The content in the vial is swirled manually. After the content is thoroughly mixed, the vial is fitted onto a Buchi rotary evaporator to dry the content as described above.

Example 28

Preparation of Simulated Gastric and Intestinal Fluid
Simulated Intestinal Fluid (SIF)

Monobasic potassium phosphate (6.8 gm) and sodium hydroxide (0.616 gm) are added into 250 ml of distilled water in a 1000 ml volumetric flask and swirled until dissolved. 700 ml distilled water is added and the pH checked. The pH is adjusted to pH 6.8+/−0.1 by adding either 0.2N sodium hydroxide or 0.2N hydrochloric acid and the volume is brought to 1000 ml.
Simulated Gastric Fluid (SGF)

Sodium chloride (2 gm), 750 ml distilled water, and 7.0 ml of concentrated hydrochloric acid are added into a 1000 ml volumetric flask. The flask is swirled to mix and the volume brought to 1000 ml with distilled water. The pH should be approx. 1.2.

Example 29

Dispersion Tests of Solid Ganaxolone Particle Formulations in Simulated Gastric and Intestinal Fluid The solid ganaxolone particle formulation is dispersed in simulated gastric and intestinal fluid and their dispersibility is monitored by visual assessment for flocculation and particle size measurement using a Horiba-LA-910 particle analyzer. The detailed procedure is described below.
In-Process Immediate Release Blend or Liquid Dispersion In a 25 ml translucent HDPE vial (total fill volume) with HDPE cap is placed appropriate amount of ganaxolone formulation (e.g. 9.8 mg dried ganaxolone powder containing 76% ganaxolone and appropriate levels of excipients) to achieve a final ganaxolone concentration of approx 0.5 mg/ml when diluted with 15 ml of simulated gastric or intestinal fluid. After adding the dispersant, the vial is shaken manually until formulation is completely dispersed. The vial is then placed in a heated oil bath at 37° C. unstirred unless specified otherwise until the desired test time. The vial is removed from the bath and inspected visually for signs of flocculation. It is then shaken before particle size measurement using a Horiba-LA-910 particle analyzer. Typically the materials are incubated for 3 hours to approximate the human gastric emptying period.
Particle Size Measurement If measuring coated beads where the bead core contains insoluble materials, calculate the weight of bead core in the SIF or SGF experiment, disperse an equal weight of core beads into the same volume of SIF or SGF and pour the entire amount into 120 gm of distilled water in the Horiba LA-910 chamber. Blank the instrument and drain. Add 120 gm distilled water and pour the entire quantity of incubated formulation (in 15 ml SGF or SIF) into the Horiba chamber. Measure the particle size. This process subtracts any particle size interference from the core beads. In the case of MCC cores, which are insoluble, measure the particle size by the method used for liquid suspension. After the initial particle size measurement of the re-dispersed ganaxolone formulation, sonicate at the low power setting on the Horiba LA-910 for 1 minute, unless specified otherwise, and re-measure the particle size. As for any suspension or dispersion study the D50 difference as well as overlapping the 2 traces can give a qualitative indication of how much of the formulation forms a loose agglomerate.

Dispersion of Ganaxolone Suspensions, Tablets and Capsules (Immediate and Delayed Release)

Place the ganaxolone solid dosage form in a type II dissolution apparatus with basket at 37° C. containing SGF at a 0.5 to 1.0 mg/ml ganaxolone concentration for the immediate release component. Stir at 75 RPM and sample at 1 hour for the particle size. Measure the particle size as described above (15 mL aliquot) using a direct measurement method if all excipients are water soluble or by filtering through a 5 micron filter or by blanking using the same blend quantity minus ganaxolone dispersed under the same conditions as the immediate release ganaxolone coated beads above. If a delayed release or pulsatile release dosage, after the SGF incubation, replace the SGF with SIF (to make 0.5 to 1 mg/ml of ganaxolone in the delayed release component. Utilize the same conditions as for SGF but let stir for 3 hours. Sample and measure the particle size as described above for the SGF portion of the study.

Example 30

Ganaxolone Dispersion Test Results

Table 15 shows test results for a ganaxolone particle suspension formulation (12.6% ganaxolone, 2.6% HPMC, 6.026% SLS, 0.018% simethicone emulsion (30% simethicone in water) and 2.4% sucrose) and two other dried forms (rotary evaporation dried and spray layered onto sucrose or microcrystalline cellulose beads). The spray layered form was prepared by evaporating the layering slurry onto sugar beads (Paulaur 30/35 mesh) through a fluidized bed coating process yielding approximately 35% ganaxolone loading (% wt GNX/% total bead wt), as assayed by HPLC-refractive index. Although the initial liquid formulation had D50 values of 343 and 361 nm after 3 h in both gastric and intestinal fluids at 36-38° C., the two dried forms had D50 values in the range of 11-25 micrometers in the same test. Further, the action of 1 minute sonication did not return D50 to its original value.

TABLE 15

Dispersion Results of Ganaxolone suspension containing HPMC, SLS, Sucrose and Simethicone (no complexing agent added) or after the removal of water via Rotary Vacuum Evaporation (Rotovap) or Spray Layered onto Sugar Beads

| Entry | Dosage Form | D50 (μm)/ D50 after 1 min sonication | Visual Observation | Dispersion conditions[1] |
|---|---|---|---|---|
| 1 | layering slurry | 0.211/0.202 | Uniform suspension | Initial |
| 2 | layering slurry | 0.343/0.291 | Flocculated | SGF, 3 h |
| 3 | layering slurry | 0.361/0.247 | Flocculated | SIF, 3 h |
| 4 | Rotvap Dried | 0.325/0.305 | Uniform suspension | Distilled water, ambient, 5 min |
| 5 | Rotvap Dried | 11.1/2.2 | flocculation | SGF, 100 min |
| 6 | Rotvap Dried | 11.3/3.1 | flocculation | SIF, 100 min |
| 7 | Layered on sugar beads | 19.5/8.8 | flocculation | SGF, 3 h |
| 8 | Layered on sugar beads | 25.5/7.6 | flocculation | SIF, 3 h |

[1]Temperature for SGF and SIF tests is the same as that described in Example 14.

Example 31

Effects of Sucrose, HPMC, SLS and PVA on Ganaxolone Particle Formulations without a Complexing Agent (Table 16)

As the data in Table 16 shows, higher level of SLS resulted in less particle growth upon dispersion in simulated gastric and intestinal fluids (entries 1-2) for non-complexed ganaxolone particle formulations. Doubling the sucrose level from 46.6 to 98.3%, while keeping the SLS level constant showed positive, but smaller effects on dispersion (entry 3). Addition of ca. 10% PVA showed similar effect to that of doubling sucrose level at the same SLS level (entry 4).

TABLE 16

Dispersion Test Results of Dried Non-Complexed Ganaxolone Particle Formulations ((initial D50: 147 nm, from Milling run Ex-21) in Both Simulated Gastric and Intestinal Fluids

| Entry | Sucrose % (w/GNX) | HPMC % (w/GNX) | SLS % (w/GNX) | PVA % (w/GNX) | D50 (μm)/ 1 min sonication | Dispersion Conditions[1] |
|---|---|---|---|---|---|---|
| 1 | 46.6 | 22.1 | 0.93 | 0 | 24.7/1.2 | SGF |
|   |      |      |      |   | 14.9/1.6 | SIF |
| 2 | 46.6 | 22.1 | 2.79 | 0 | 0.984/0.26 | SGF |
|   |      |      |      |   | 1.21/0.28 | SIF |
| 3 | 98.3 | 22.1 | 0.98 | 0 | 13.9/0.30 | SGF |
|   |      |      |      |   | 12.2/0.28 | SIF |
| 4 | 48.8 | 22.1 | 0.98 | 9.75 | 12.3/3.19 | SGF |
|   |      |      |      |      | 11.2/4.22 | SIF |

[1] Conditions are the same as Example 14

Example 32

Dispersion of Solid Ganaxolone Particle Formulations with a Paraben Complexing Agent

Example 32a

Solid Particles Prepared from 6-Month Old Suspension Formulation Containing a Complexing Agent Solid ganaxolone particles prepared from a 6-month old stable suspension formulation as described in Example 45 (Ex-45) containing 52% HPMC, 10.4% PVA, 1.25% parabens, and 1.0% SLS re-dispersed well in both simulated gastric and intestinal fluids at 36-38° C. (entry 5, Table 17). Addition of 54.8% of sucrose further improved the re-dispersibility especially in simulated gastric fluid (entry 3). Adding additional 2.3% SLS to this formulation further reduced particle growth upon dispersion, particularly in simulated gastric fluid (entry 4). Doubling the sucrose level also provided positive stabilization effect (entry 2).

TABLE 17

Dispersion Test Results of Dried Stable Ganaxolone Formulations containing a complexing agent ((Ex-45) in Simulated Gastric and Intestinal Fluids (D50: 205 nm)

| Entry | Sucrose % (w/GNX) | HPMC % (w/GNX) | SLS % (w/GNX) | Parabens[a] % (w/GNX) | D50 (μm)/ 1 min sonication | disperse conditions[b] |
|---|---|---|---|---|---|---|
| 1 | 104.2 | 52.1 | 1.0 | 1.25 | 0.203 | DI water, ambient |
| 2 | 104.2 | 52.1 | 1.0 | 1.25 | 0.329/0.215 | SGF, 2 h |
|   |       |      |     |      | 0.333/0.217 | SIF, 2 h |
| 3 | 54.8 | 52.1 | 1.0 | 1.25 | 0.363/0.213 | SGF, 3 h |
|   |      |      |     |      | 0.333/0.216 | SIF, 3 h |
| 4 | 54.8 | 52.1 | 3.3 | 1.25 | 0.314/0.211 | SGF, 3 h |
|   |      |      |     |      | 0.328/0.219 | SIF, 3 h |
| 5 | 0 | 52.1 | 1.0 | 1.25 | 0.408/0.285 | SGF, 3 h |
|   |   |      |     |      | 0.367/0.283 | SIF, 3 h |

[a]1.04% methylparaben and 0.21% propylparaben;
[b]Temperature for SGF and SIF tests is the same as that described in Example 14.

Example 32b

Solid Particles Prepared from a 1 Week Old Ganaxolone Suspension Formulation Containing Methylparaben as the Complexing Agent Solid ganaxolone particles prepared from a 1-week old methylparaben suspension formulation containing 0.98% methylparaben in addition to 24.4% HPMC, 0.15% simethicone (30% emulsion in water), 1.46% SLS were tested for dispersion in both simulated gastric and intestinal fluids at 36-38° C. (Table 18). Consistent with previous observations, higher level of SLS resulted in less particle size growth upon dispersion (entry 2) in both gastric and intestinal fluid. Addition of 25% sucrose to the above formulation further reduced particle size growth upon dispersion (entry 3). Addition of 9.76% PVA provided less obvious benefit.

TABLE 18

Dispersion Test Results of Dried Ganaxolone (GNX) Particle Formulations Prepared from Milling Slurry Containing Methylparaben in Gastric and Intestinal Fluids (initial: 310 nm nm): Effects of Sucrose, SLS, PVA and Simethicone (all % expressed as wt %/GNXwt)

| Entry | Sucrose % | HPMC % | 30% SE | SLS % | Methyl-paraben % | PVA % | D50 (μm)/ D50 (μm) after 1 min sonication | Dispersion Conditions[1] |
|---|---|---|---|---|---|---|---|---|
| 1 | 0 | 24.4 | 0.15 | 1.46 | 0.98 | 0 | 30.0/0.333 | A |
|   |   |      |      |      |      |   | 19.5/0.312 | B |
| 2 | 0 | 24.4 | 0.15 | 2.93 | 0.98 | 0 | 5.6/0.303 | A |
|   |   |      |      |      |      |   | 8.2/0.302 | B |

TABLE 18-continued

Dispersion Test Results of Dried Ganaxolone (GNX) Particle Formulations
Prepared from Milling Slurry Containing Methylparaben in Gastric
and Intestinal Fluids (initial: 310 nm nm): Effects of Sucrose,
SLS, PVA and Simethicone (all % expressed as wt %/GNXwt)

| Entry | Sucrose % | HPMC % | 30% SE | SLS % | Methyl-paraben % | PVA % | D50 (μm)/ D50 (μm) after 1 min sonication | Dispersion Conditions[1] |
|---|---|---|---|---|---|---|---|---|
| 3 | 25 | 24.4 | 0.15 | 2.93 | 0.98 | 0 | 0.517/0.291 | A |
|   |    |      |      |      |      |   | 0.807/0.288 | B |
| 4 | 24.4 | 24.4 | 0.15 | 2.93 | 0.98 | 9.76 | 2.29/0.309 | A |
|   |      |      |      |      |      |      | 2.13/0.328 | B |
| 5 | 0 | 24.4 | 0.49 | 2.93 | 0.98 | 0 | 9.02/0.304 | A |
|   |   |      |      |      |      |   | 11.23/0.314 | B |
| 6 | 0 | 24.4 | 0.98 | 2.93 | 0.98 | 0 | 7.66/0.315 | A |
|   |   |      |      |      |      |   | 9.44/0.311 | B |

[1]Re-disperse conditions: A, simulated gastric fluid, 36-38° C., 3 h; B. Simulated intestinal fluid, 36-38° C., 3 h. SE = Simethicone Example 33

Head to Head Comparison of Re-Dispersibility in Simulated Gastric And Intestinal Fluids of Solid Ganaxolone Particles: with and without a Complexing Agent (Methylparaben) Added Two liquid ganaxolone particles formulations were prepared as described in Examples 51 and 52 respectively: one contained 0.98% methylparaben in addition to 24.3% HPMC and 1.46% SLS (Ex-51) and the other one contained only comparable levels of HPMC and SLS (Ex-52). When these two liquid formulations tested side by side in simulated gastric and intestinal fluid at 37° C., the complexing agent containing formulation Ex-51 (entry 1, Table 19) showed significantly less particle size growth compared to the formulation Ex-52 without the complexing agent (entry 2, Table 19). With additional amounts of HPMC and SLS added (entries 3-4, table 19), similar results were obtained. These results are consistent with those discussed earlier. Solid ganaxolone particles prepared from the suspensions listed in entries 3-4, Table 19 were re-dispersed in simulated gastric and intestinal fluid, the paraben-containing formulation showed less particle size growth than its no-paraben counterpart (entries 3-4, Table 20).

TABLE 19

Gastric and intestinal stability study of formulations prepared
from Ex-51 and Ex-52: Effect of Methyl paraben as the complexing
agent (formulations tested as suspension)

| Entry | HPMC (w/GNX) | SLS % (w/GNX) | Methyl-paraben %(w/GNX) | D50 (μm) No Sonication/1 min sonication | Test conditions[1] |
|---|---|---|---|---|---|
| 1 | 24.4 | 1.46 | 0.98 | 0.382/0.324 | A |
|   |      |      |      | 0.394/0.326 | B |
| 2 | 23.5 | 1.41 | 0 | 0.897/0.290 | A |
|   |      |      |   | 7.36/0.283 | B |
| 3 | 47.1 | 2.82 | 0 | 0.828/0.258 | A |
|   |      |      |   | 0.933/0.267 | B |
| 4 | 48.8 | 2.93 | 0.98 | 0.350/0.314 | A |
|   |      |      |      | 0.353/0.313 | B |

[1]dispersion conditions: A, simulated gastric fluid, 36-38° C., 3 h; B. Simulated intestinal fluid, 36-38° C., 3 h.

Additional comparative dispersion studies of solid ganaxolone particles with and without parabens were carried out in simulated gastric and intestinal fluids. Ganaxolone particles with 0.98% methylparaben as the complexing agent (allowed to cure for 1 week) showed significant less particle growth upon dispersion at 37° C. than that containing no complexing agent (entries 2-3, Table 20). Presence of 9.4-9.8% PVA did not significantly alter the dispersion behaviors of solid ganaxolone particles with and without the complexing agent (entries 1&4, 2&3, table 20). For formulation listed in entry 4, Table 19, addition of ca 52% of sucrose significantly reduced particle size growth upon dispersion (entry 8, table 6.6). However, doubling the sucrose level did not show any significant additional benefit (entry 9, Table 20). Similar trends were observed for solid ganaxolone formulations containing no complexing agent (entries 6&7, 10&11, Table 20). Compared with formulation listed in entry 8, Table 20, lowering the levels of sucrose, HPMC and SLS resulted in larger particle size upon dispersion, especially in simulated intestinal fluid (entry 5, Table 20).

TABLE 20

Comparative Dispersion Results of Dried Ganaxolone Particle Formulations Prepared from a ganaxolone suspension with Methylparaben (Ex-51, 24.4% HPMC, 0.98% methylparaben, initial D50: 148 nm, complexed D50: 310 nm cured for 7 days at 20° C.) and without Methylparaben (Ex-52, D50: 147 nm) in Gastric and Intestinal Fluids: Effects of Sucrose, SLS, PVA

| Entry | Sucrose % (w/GNX) | HPMC (w/GNX) | SLS % (w/GNX) | PVA % (w/GNX) | Methylparaben % (w/GNX) | D50 (μm) No sonication/1 min sonication | disperse conditions[1] |
|---|---|---|---|---|---|---|---|
| 1 | 0 | 48.3 | 2.90 | 9.8 | 0.98 | 0.69/0.332 | SGF, 3 h |
|   |   |   |   |   |   | 1.14/0.336 | SIF, 3 h |
| 2 | 0 | 46.6 | 2.80 | 9.4 | 0 | 4.04/0.768 | SGF, 3 h |
|   |   |   |   |   |   | 3.57/0.677 | SIF, 3 h |
| 3 | 0 | 47.1 | 2.82 | 0 | 0 | 4.02/1.12 | SGF, 3 h |
|   |   |   |   |   |   | 4.13/1.24 | SIF, 3 h |
| 4 | 0 | 48.8 | 2.93 | 0 | 0.98 | 0.636/0.314 | SGF, 3 h |
|   |   |   |   |   |   | 1.28/0.322 | SIF, 3 h |
| 5 | 15.4 | 32.9 | 1.9 | 0 | 1.3 | 0.754/0.317 | SGF, 3 h |
|   |   |   |   |   |   | 2.64/0.322 | SIF, 3 h |
| 6 | 47.0 | 23.5 | 2.8 | 0 | 0 | 2.89/0.303 | SGF, 3 h |
|   |   |   |   |   |   | 15.87/0.296 | SIF, 3 h |
| 7 | 94.1 | 23.5 | 2.8 | 0 | 0 | 6.89/0.280 | SGF, 3 h |
|   |   |   |   |   |   | 13.98/0.288 | SIF, 3 h |
| 8 | 51.8 | 49.3 | 3.0 | 0 | 0.98 | 0.366/0.283 | SGF, 3 h |
|   |   |   |   |   |   | 0.413/0.304 | SIF, 3 h |
| 9 | 103.8 | 46.7 | 2.8 | 0 | 0.98 | 0.383/0.292 | SGF, 3 h |
|   |   |   |   |   |   | 0.588/0.304 | SIF, 3 h |
| 10 | 52.1 | 52.1 | 3.1 | 0 | 0 | 2.09/0.301 | SGF, 3 h |
|   |   |   |   |   |   | 3.94/0.316 | SIF, 3 h |
| 11 | 104.4 | 47.1 | 3.1 | 0 | 0 | 2.72/0.293 | SGF, 3 h |
|   |   |   |   |   |   | 5.46/0.301 | SIF, 3 h |

[1]Temperature for SGF and SIF tests is the same as that described in Example 14.

Example 34

Effect of Salts on Dispersion of Dried Ganaxolone Particle Formulations with and without a Complexing Agent Added Sodium chloride is very effective in improving dispersion of a dried ganaxolone particle formulation (described in Example 51) cured with a complexing agent in both simulated gastric and intestinal fluid. The results are shown in Table 21. At 1.5 w %/GNX level, sodium chloride reduced D50 from 13.2 μm to 3.17 μm upon dispersion in simulated gastric fluid at room temperature (entries 1-2). Raising the sodium chloride level to 2.0% relative to ganaxolone, under the same conditions, decreased D50 to 0.548 μm in gastric fluid. Above 3.0%, sodium chloride essentially prevented particle size growth upon dispersion in gastric and intestinal fluid (entries 6-9, 11, Table 21). At low sodium chloride level, additional stabilization effect can be obtained by adding a water soluble spacer which has more plasticity than salts. The water soluble spacer used to illustrate this point is sucrose. As shown in entry 4, at 1.5% sodium chloride level, addition of 2.5% of sucrose (relative to ganaxolone) reduced D50 to the same level as 3.0% sodium chloride. Increasing the sucrose level to 5% provided little additional benefit (entry 3). For the stabilized solid ganaxolone particle formulation containing methylparaben as a complexing agent and cured for >7 days, the increase in D50 values is primarily caused by loose aggregation upon dispersion. A 1 min sonication at the low power setting readily reverses these loose aggregates back to individual smaller particles, as shown in Table 21.

For the regular ganaxolone particle formulation that has not been stabilized by a complexing agent, addition of sodium chloride at a level as high as 23.5% relative to ganaxolone resulted in D50 of 22.7 μm upon dispersion in simulated gastric fluid at room temperature. This significant increase in D50 upon dispersion can only be partially reversed after 1 min low power sonication (entry 12, table 21). The actual particle distribution traces (after 1 min low power sonication) for entries 9 (with methylparaben) and 12 (without methylparaben) are shown in FIG. 5.

TABLE 21

Effect of sodium chloride on dispersion of dried ganaxolone particles (with and without complexing agent) and in simulated gastric and intestinal fluid (SGF and SIF)

| Entry | HPMC % w/GNX | SLS % w/GNX | Simethicone 30% emulsion % w/GNX | Methylparaben % w/GNX | NaCl % w/GNX | Sucrose % w/GNX | D50(μm) no sonication/ D50(μm) after 1 min sonication | Dispersion conditions |
|---|---|---|---|---|---|---|---|---|
| 1 | 24.4 | 1.46 | 0.15 | 0.98 | 0 | 0 | 13.2/0.332 | SGF, 5 min, rt |
| 2 | 24.4 | 1.46 | 0.15 | 0.98 | 1.5 | 0 | 3.17/0.337 | SGF, 5 min, rt |
|   |   |   |   |   |   |   | 4.45/0.353 | SIF, 5 min, rt |
| 3 | 24.4 | 1.46 | 0.15 | 0.98 | 1.5 | 5 | 0.364/0.316 | SGF, 5 min, rt |
|   |   |   |   |   |   |   | 0.396/0.322 | SIF, 5 min, rt |

TABLE 21-continued

Effect of sodium chloride on dispersion of dried ganaxolone particles (with and without complexing agent) and in simulated gastric and intestinal fluid (SGF and SIF)

| Entry | HPMC % w/GNX | SLS % w/GNX | Simethicone 30% emulsion % w/GNX | Methyl-paraben % w/GNX | NaCl % w/GNX | Sucrose % w/GNX | D50(μm) no sonication/ D50(μm) after 1 min sonication | Dispersion conditions |
|---|---|---|---|---|---|---|---|---|
| | | | | | | | 0.490/0.331 | SGF, 3 h, 36-38° C., stirred |
| | | | | | | | 0.561/0.329 | SIF, 3 h, 36-38° C., stirred |
| 4 | 24.4 | 1.46 | 0.15 | 0.98 | 1.5 | 2.5 | 0.395/0.323 | SGF, 5 min, rt |
| | | | | | | | 0.370/0.312 | SIF, 5 min, rt |
| | | | | | | | 0.416/0.326 | SGF, 3 h, 36-38° C., stirred |
| | | | | | | | 0.533/0.331 | SIF, 3 h, 36-38° C., stirred |
| 5 | 24.4 | 1.46 | 0.15 | 0.98 | 2.0 | 0 | 0.548/0.334 | SGF, 5 min, rt |
| | | | | | | | 0.506/0.326 | SIF, 5 min, rt |
| 6 | 24.4 | 1.46 | 0.15 | 0.98 | 3.0 | 0 | 0.355/0.319 | SGF, 5 min, rt |
| | | | | | | | 0.367/0.315 | SIF, 5 min, rt |
| | | | | | | | 0.485/0.329 | SGF, 3 h, 36-38° C., stirred |
| | | | | | | | 0.609/0.334 | SIF, 3 h, 36-38° C., stirred |
| 7 | 24.4 | 1.46 | 0.15 | 0.98 | 6.1 | 0 | 0.338/0.314 | SGF, 5 min, rt |
| | | | | | | | 0.429/0.337 | SIF, 5 min, rt |
| 8 | 24.4 | 1.46 | 0.15 | 0.98 | 12.2 | 0 | 0.353/0.317 | SGF, 5 min, rt |
| | | | | | | | 0.367/0.318 | SIF, 5 min, rt |
| 9 | 24.4 | 1.46 | 0.15 | 0.98 | 24.4 | 0 | 0.344/0.319 | SGF, 5 min, rt |
| 10 | 24.4 | 1.46 | 0.15 | 0.98 | 24.4 | 0 | 0.440/0.322 | SGF, 70 min, 36-38° C. |
| | | | | | | | 0.459/0.324 | SIF, 70 min, 36-38° C. |
| 11 | 24.4 | 1.46 | 0.15 | 0.98 | 36.6 | 0 | 0.346/0.315 | SGF, 5 min, rt |
| | | | | | | | 0.372/0.317 | SIF, 5 min, rt |
| 12 | 23.5 | 1.41 | 0.14 | 0 | 23.5 | 0 | 22.7/8.9 | SGF, 5 min, rt |

Other salts are also effective in improving re-dispersibility of solid ganaxolone particles in simulated gastric and intestinal fluid. Shown in table 22 are test results of sodium citrate.

TABLE 22

Effect of sodium citrate on dispersion of dried ganaxolone particles (complexing agent added) in simulated gastric and intestinal fluid (SGF and SIF)

| Entry | HPMC % w/GNX | SLS % w/GNX | Simethicone 30% emulsion % w/GNX | Methyl-paraben % w/GNX | Na Citrate % w/GNX | D50(μm) No sonication/1 min sonication | Disperse conditions |
|---|---|---|---|---|---|---|---|
| 1 | 24.4 | 1.46 | 0.15 | 0.98 | 24.4 | 0.454/0.333 | SGF, 5 min, rt |
| 2 | 24.4 | 1.46 | 0.15 | 0.98 | 24.4 | 0.820/0.337 | SGF, 70 min, 36-38° C. |
| 3 | 24.4 | 1.46 | 0.15 | 0.98 | 24.4 | 0.982/0.342 | SiF, 70 min, 36-38° C. |

Example 35

Preparation of Solid Ganaxolone Particles Containing Sucrose, Sodium Chloride in Addition to the Milling Excipients The following was placed in a 25 ml glass scintillation vial: 5.13 mg of sucrose crystals and 12.5 mg of 25% wt sodium chloride solution. Deionized water (0.5 g) was then added to dissolve the sucrose crystals and to achieve a homogeneous solution.

Aqueous ganaxolone suspensions (1 g) containing 20.5% ganaxolone, 5.0% HPMC, 0.3% sodium lauryl sulfate, 0.2% methylparaben 0.03% simethicone (30% emulsion in water) (all % w/w) was then added to the vial and the mixture was swirled to mix well. The contents in the vial were then evaporated under reduced pressure (rotary vacuum evaporator at 2-4 mbar) at 70-85° C. until a dry powder was obtained.

The examples listed in Table 23 were prepared in the same fashion with appropriate amounts of each component.

TABLE 23

| Example | Milling Slurry (g) | NaCl solution (25% wt) | Sucrose (g) | Deionized water (g) |
|---|---|---|---|---|
| 1 | 1.0 | 0.3 | 0 | 0.5 |
| 2 | 1.0 | 0.2 | 0 | 0.5 |
| 3 | 1.0 | 0.1 | 0 | 0.5 |
| 4 | 1.0 | 0.05 | 0 | 0.5 |

TABLE 23-continued

| Example | Milling Slurry (g) | NaCl solution (25% wt) | Sucrose (g) | Deionized water (g) |
|---|---|---|---|---|
| 5 | 1.0 | 0.025 | 0 | 0.5 |
| 6 | 1.0 | 0.0125 | 0.01025 | 0.5 |
| 7 | 1.0 | 0.0164 | 0 | 0.5 |

Example 36

Effect of Boiling on Ganaxolone Formulations with and without a Complexing Agent Approx. 2 g of the milling slurry of Ex-51 and Ex-52 prepared as described in Examples 51 and 52 respectively was placed in a 25 ml glass vial and the vial was closed tightly. The vials were heated in 100° C. oil bath. The particle size of Ex-51 which contained methylparaben as complex agent did not change after heating. In contrast, Ex-52 which did not contain a complexing agent increased its D50 and the increase appeared to be time dependent. Also, both formulations became more viscous with Ex-51 becoming a semi-solid (it was diluted with water for particle size measurement).

TABLE 24

| Formulation | Initial D50 (nm) before/after 1 min sonication | D50 (nm) after 20 min at 100° C. | D50 (nm) after 4 h at 100° C. |
|---|---|---|---|
| Ex-51 | 320/298 | 326/311 | 320/310 |
| Ex-52 | 149/140 | 246/207 | 317/302 |

Example 37

Dispersion Test Results of Solid Ganaxolone Particle Formulations with Sodium Benzoate as Curing Agent in Simulated Gastric and Intestinal Fluid Solid ganaxolone particle formulations containing sodium benzoate/benzoic acid as a complexing agent were prepared according to the milling method for formulations with parabens as complexing agent (see method described in Example 52) except using ganaxolone particle suspension containing 21.25% ganaxolone, 5% HPMC, 0.3% Sodium lauryl sulfate, 0.03% simethicone emulsion (30%) with 0.09% sodium benzoate, 0.12% citric acid and 0.0093% sodium citrate added post-milling (all % w/w) (Ex-52) and cured for 12 days at the time of use.

As shown in Table 25, solid ganaxolone particles prepared from milling slurry Ex-52 containing 23.5% HPMC, 1.41% SLS and 0.14% simethicone emulsion (30%) showed poor re-dispersibility. Post-milling addition of sodium benzoate (0.42%), citric acid (0.56%) and sodium citrate (0.043%) to this suspension improved its re-dispersibility in gastric and intestinal fluid (entry 3). As in the case of paraben-containing solid formulations, addition of sodium chloride (23.5%) further reduced its D50 upon dispersion in simulated gastric and intestinal fluid (entry 4).

TABLE 25

| Entry | HPMC % w/GNX | SLS % w/GNX | Simethicone 30% emulsion % w/GNX | Sodium benzoate/citric acid/sodium citrate % w/GNX | NaCl % w/GNX | D50(μm) no sonication/D50 (μm) 1 min sonication | Dispersion conditions |
|---|---|---|---|---|---|---|---|
| 1 | 23.5 | 1.41 | 0.14 | 0 | 0 | 37.2/4.9 | SGF, 5 min rt |
| 2 | 23.5 | 1.41 | 0.14 | 0 | 23.5 | 22.7/8.9 | SGF, 5 min, rt |
| 3 | 23.5 | 1.41 | 0.14 | 0.42/0.56/0.043 | 0 | 16.5/0.747 | SGF, 5 min, rt |
|   |      |      |      |                 |   | 14.3/0.525 | SIF, 5 min, rt |
| 4 | 23.5 | 1.41 | 0.14 | 0.42/0.56/0.043 | 23.5 | 9.0/0.347 | SGF, 5 min, rt |
|   |      |      |      |                 |      | 7.5/0.343 | SIF, 5 min, rt |

Example 38

Filterability of Ganaxolone Particle Suspensions with and without a Complexing Agent (Methylparaben)

Ganaxolone particle suspension (247 mg, Ex-51) containing 20.5% ganaxolone, 5% HPMC, 0.3% sodium lauryl sulfate, 0.2% methylparaben and 0.03% simethicone emulsion (30%) was diluted with deionized water (100 ml) and thoroughly mixed to obtain 0.5 mg/ml ganaxolone concentration.

Ganaxolone particle suspension (235 mg, Ex-52) containing 21.25% ganaxolone, 5% HPMC, 0.3% sodium lauryl sulfate, 0.03% simethicone emulsion was diluted with deionized water (100 mL) and thoroughly mixed to obtain 0.5% mg/ml ganaxolone concentration.

The filterability of the diluted suspensions was evaluated by transmittance (lamp) and particle size change before and after filtration. To obtain about 75% transmittance (lamp) before filtration, for dilute suspension of Ex-51, 10 g was mixed with 120 mL of deionized water in the Horiba LA-910 sample chamber and the particle size was measured. The chamber was drained and rinsed with water. In the chamber was then mixed 10 g of the dilute suspension filtered through a 1 micron glass fiber syringe filter and 120 ml deionized water the particle size was measured.

For the dilute suspension of Ex-52, 25 g of the suspension and 80 ml of deionized water was used. The transmittance (% T lamp) and D50 were compared before and after filtration to determine the amount of ganaxolone particles retained on the filter. Higher transmittance indicates lower particle concentration in the measuring chamber. Further, decreasing D50 after filtration indicates the removal of particles with altered physical properties (aggregates or adhesion onto the membrane) during filtration. As data in Table 26 shows, a significant amount of the ganaxolone particles complexed by methylparaben were retained by the filter as depicted by the loss of lamp transmittance value which indicates how many particles are in the sample chamber (entry 1). This statement is also consistent with significant back pressure encountered during filtration. In contrast, the ganaxolone particles not associated with a complexing agent were not retained by the filter (entry 2). In this case, virtually no back pressure was encountered.

TABLE 26

Filterability of ganaxolone particles with and without a complexing agent

| entry | HPMC % (w/GNX) | SLS % (w/GNX) | Simethicone emulsion 30% (w/GNX) | Methyl-paraben % (w/GNX) | Before filtration D50 (µm) | Before filtration % T (lamp) | After filtration D50 (µm) | After filtration % T (lamp) |
|---|---|---|---|---|---|---|---|---|
| 1 | 24.4 | 1.46 | 0.15 | 0.98 | 0.324 | 77.5 | 0.191 | 94.4 |
| 2 | 23.5 | 1.41 | 0.14 | 0 | 0.152 | 77.1 | 0.146 | 79.1 |

Example 37

Milling of Ganaxolone Particles in Aqueous Medium Containing HPMC and Sodium Lauryl Sulfate (Batch Mode)

Ganaxolone particles in deionized water (180 g) containing a 30 wt % ganaxolone (Marinus Pharmaceuticals Inc., Connecticut, USA), 3 wt % HPMC, and 0.1% (w/w) sodium lauryl sulfate was milled in a DYNO Mill KDL (Willy A. Bachofen A. G., Maschinenfabrik, Basel, Switzerland) with a 300 mL glass batch chamber and utilizing 0.1-0.2 mm zirconium oxide beads (85% of the chamber volume). The milling was conducted for 120 min at a tip speed of 22.5 m/s. The particle size (D50) after milling was 106 nm.

Example 38

Milling of Aqueous Ganaxolone Dispersion Containing HPMC (Continuous Mode)

Powdered ganaxolone aqueous dispersion (1200 g) comprising a mixture of 20 wt % ganaxolone and 3 wt % HPMC was milled in a DYNO Mill KDL with a 600 mL SiC lined continuous chamber and 0.4 mm yttrium stabilized zirconium oxide beads (88% volume loading). The milling slurry was re-circulated via a peristaltic pump (250 mL/min) through a jacketed stainless steel holding tank chilled between 0-12° C. The tip speed was 10 m/s. The product temperature at the outlet was kept below 45° C. The progress of the milling run was followed by particle size measurement (D50) at various time points. After 2 hours of milling, the slurry with a D50 of 330 nm was filtered through a 10 µm cartridge and stored refrigerated.

Example 39

Milling of Aqueous Ganaxolone Dispersion Containing HPMC (Continuous Mode)

Powdered ganaxolone aqueous dispersion (1000 g) comprising a mixture of 15 wt % ganaxolone and 2.5 wt % HPMC was milled in a DYNO Mill KDL as described for Example 38. After 70 min residence time, D50 was 125 nm. The slurry was split into 6 portions (Ex-39A-F) and different excipients were added to each portion. The final amounts of the excipients of each formulation are listed in the Table 27.

TABLE 27

| Formulation | A | B | C | D | E | F |
|---|---|---|---|---|---|---|
| HPMC % (w/w) | 2.5 | 2.5 | 2.5 | 5.0 | 2.5 | 7.5 |
| SLS % (w/w) | 0 | 0 | 0.3 | 0.1 | 0 | 0.3 |
| DOSS % (w/w) | 0 | 0 | 0 | 0 | 0.1 | 0 |

Example 40

Milling of Ganaxolone Particles in Aqueous Medium Containing HPMC and Sodium Lauryl Sulfate (Continuous Mode)

Ganaxolone particles in deionized water (1200 g) containing 15 wt % ganaxolone, 3 wt % HPMC, and 0.05 wt % Sodium lauryl sulfate was milled in a DYNO Mill KDL with a 600 mL SiC lined continuous chamber and 0.4 mm yttrium stabilized zirconium oxide beads (90% volume loading). The milling slurry was re-circulated via a peristaltic pump (250 mL/min) through a jacketed stainless steel holding tank chilled between 0-12° C. The tip speed was 10 m/s. The product temperature at the outlet was kept below 45° C. About 15 min into the milling, additional 0.05% SLS was added as a concentrated solution. The progress of the milling run was followed by particle size measurement (D50) at various residence time points (plot shown in FIG. 4). After milling, the slurry was filtered through a 10 µm cartridge and stored refrigerated. Residence times of approximately 30 minutes or more produced sub-micron ganaxolone particles having D50 of 100 nm to 150 nm.

Example 41

Milling of Ganaxolone Particles in Aqueous Medium Containing HPMC, Sodium Lauryl Sulfate, Polyvinyl Alcohol, Methylparaben and Propylparaben (Continuous Mode)

Ganaxolone particles in deionized water (1000 g) containing 15 wt % ganaxolone, 3 wt % HPMC, 1 wt % polyvinyl alcohol, 0.1 wt % methylparaben, 0.02 wt %, and propylparaben was milled in a DYNO Mill KDL with a 600 mL SiC lined continuous chamber and 0.4 mm yttrium stabilized zirconium oxide beads (90% volume bead loading). The milling was conducted according to the method described in Example 38. During the milling, two portions of 0.025% (w/w) of sodium lauryl sulfate were added as a concentrate solution. After 72.9 min of residence time, the D50 was 153 nm. The milling slurry was split into three containers, additional sodium lauryl sulfate was added to two of the containers so that the total SLS levels reached 0.1 and 0.2% w/w respectively. The slurries were stored at ambient temperature and particle size became fully sable after 6 days (D50 values: 205, 188 and 193 respectively).

Example 42

Milling of Ganaxolone Particles in Aqueous Medium Containing HPMC, Sodium Lauryl Sulfate, Polyvinyl Alcohol, Methylparaben, Propylparaben and Simethicone (Continuous Mode)

Ganaxolone particles in deionized water (1200 g) containing 25 wt % ganaxolone, 5 wt % HPMC, 1 wt % polyvinyl alcohol, 0.1 wt % sodium lauryl sulfate, 0.1 wt % methylparaben, 0.02 wt % propylparaben, and 0.1 wt % simethicone in deionized water was milled in a DYNO Mill KDL with a 600 mL SiC lined continuous chamber and 0.4 mm yttrium stabilized zirconium oxide beads (90% volume bead loading). The milling was conducted according to the method described in Example 38. After 27.5 min of residence time, the D50 was 180 nm. The milling slurry was filtered through a 10 μm cartridge and diluted (2×) with diluent 5% (w/w) HPMC, 1% (w/w) polyvinyl alcohol, 0.1% (w/w) sodium lauryl sulfate, 0.1% (w/w) methylparaben and 0.02% (w/w) propylparaben and 0.1% (w/w) simethicone and stored at ambient temperature for particle size to stabilize. The D50 became 327 nm after the particles were fully cured.

Example 43

Milling of Ganaxolone Particles in Aqueous Medium Containing HPMC, Sodium Lauryl Sulfate, Polyvinyl Alcohol, Sodium Benzoate, Citric Acid and Sodium Citrate (Continuous Mode)

Ganaxolone particles in deionized water (1200 g) containing 25 wt % ganaxolone, 5 wt % HPMC, 1 wt % polyvinyl alcohol, 0.1 wt % sodium benzoate, 0.12 wt % citric acid, 0.1 wt % sodium lauryl sulfate, 0.0093 wt % sodium citrate, and 0.025 wt % simethicone was milled in a DYNO Mill KDL with a 600 mL SiC lined continuous chamber and 0.4 mm yttrium stabilized zirconium oxide beads (90% volume bead loading). The milling was conducted in the same fashion as described in Example 38. After 25.0 min of residence time, the D50 was 160 nm. The milling slurry was filtered through a 10 μm cartridge and stored at ambient temperature. Its particle size (D50) became 361 nm after 4 weeks.

Example 44

Milling of Ganaxolone Particles in Aqueous Medium Containing HPMC, Sodium Lauryl Sulfate, Polyvinyl Alcohol, Methylparaben and Propylparaben (Continuous Mode)

Ganaxolone particles in deionized water (1200 g) containing 25 wt % ganaxolone, 3 wt % HPMC, 1 wt % polyvinyl alcohol, 0.1 wt % sodium lauryl sulfate, 0.1 wt % methylparaben and 0.02 wt % propylparaben was milled in a DYNO Mill KDL with a 600 mL SiC lined continuous chamber and 0.4 mm yttrium stabilized zirconium oxide beads (90% volume bead loading). The milling was conducted according to the method described in Example 43. After 25.4 min of residence time, the D50 was 162 nm. The milling slurry was filtered through a 10 μm cartridge and diluted (2×) with diluent containing 7.5% (w/w) HPMC, 1% (w/w) polyvinyl alcohol, 0.1% 9 w/w) sodium lauryl sulfate, 0.1% (w/w) methylparaben and 0.02% (w/w) propylparaben in water to obtain a liquid dispersion. The dispersion was stored at ambient temperature for particle size to stabilize. The D50 was 306 nm after 2 days and 380 nm in 4 weeks. Additional additives, for example flavoring agent and a sweetener, can be added to the liquid dispersion either before or after curing to obtain the final ganaxolone particle formulation.

Example 45

Re-Milling of Aqueous Ganaxolone Slurry Containing HPMC, Sodium Lauryl Sulfate, Polyvinyl Alcohol, Methylparaben, and Propylparaben (Continuous Mode)

The final milling slurry obtained in Example 44 was re-milled two days later according to the method described in Example 44 for 69 min of residence time. The D50 was 164 nm. It became 200 nm in 7 to 10 days and remained the same when tested 6 months later.

Example 46

Milling of Aqueous Ganaxolone Dispersion Containing HPMC (Continuous Mode)

Powdered ganaxolone aqueous dispersion (1200 g) comprising a mixture of 15 wt % ganaxolone and 3 wt % HPMC was milled in a DYNO Mill KDL as described for Example 38. During milling, 2 portions of 0.05% w/w sodium lauryl sulfate were added to keep the milling slurry fluid. After 50.8 minutes of residence time, D50 was 116 nm.

Example 47

Milling of Aqueous Ganaxolone Dispersion Containing HPMC, Sodium Lauryl Sulfate and Simethicone (Continuous Mode)

Powdered ganaxolone aqueous dispersion (1200 g) comprising a mixture of 30 wt % ganaxolone and 5 wt % HPMC, 0.2 wt % sodium lauryl sulfate and 100 ppm simethicone was milled in a DYNO Mill KDL as described for Example 38. After 24.0 minutes of residence time, D50 was 163 nm.

Example 48

Milling of Aqueous Ganaxolone Dispersion Containing HPMC, Sodium Lauryl Sulfate and Simethicone (Continuous Mode)

Powdered ganaxolone aqueous dispersion (1200 g) comprising a mixture of 25 wt % ganaxolone and 5 wt % HPMC, 0.3 wt % sodium lauryl sulfate and 100 ppm simethicone was milled in a DYNO Mill KDL as described for Example 38. After 67.7 minutes of residence time, D50 was 145 nm.

Example 49

Milling of Aqueous Ganaxolone Dispersion Containing HPMC, Sodium Lauryl Sulfate and Simethicone (Continuous Mode)

Powdered ganaxolone aqueous dispersion (1500 g) comprising a mixture of 25 wt % ganaxolone and 5 wt % HPMC, 0.1 wt % sodium lauryl sulfate and 0.028% simethicone 30% emulsion was milled in a DYNO Mill KDL as described for Example 38, except the tip speed was 15 m/s. After 39 minutes of residence time, D50 was 113 nm.

Example 50

Milling of Aqueous Ganaxolone Dispersion Containing HPMC, Sodium Lauryl Sulfate and Simethicone (Continuous Mode)

Three additional milling runs were performed in the same fashion as described for Example 46 except on larger scales. The residence time was 33, 35, and 34 minutes respectively and at the end of milling, the D50 was 143, 139, and 155 nm (after 1 minute sonication) respectively. The milled slurries from these runs were diluted in a two-step fashion as described in Example 21 to 50 mg/mL ganaxolone formulations with appropriate levels of excipients such as HPMC, PVA and SLS and other desirable components such as preservatives, sweetener and artificial flavors. The D50 values of the 50 mg/mL formulations were 320, 295, and 315 nm respectively.

Example 51

Milling of Aqueous Ganaxolone Dispersion with Complexing Agent for Solid Dosage Form Ganaxolone was wet milled in a 600 ml chamber using a DYNO-Mill KDL equipped with four 64 mm polyurethane agitator discs. The mill was operated at 3000 RPM or a tip speed of 10 m/sec. The mill was loaded with 88 vol % of 0.4 mm yttrium stabilized zirconium oxide beads. The milling slurry (1200 gm) contained 25 wt % ganaxolone, 5 wt % hydroxypropyl methylcellulose (Pharmacoat 603), 0.0333 wt % 30% simethicone emulsion, 0.3 wt % sodium lauryl sulfate and 0.2 wt % methylparaben. This slurry was circulated through the mill via a peristaltic pump and returned to a cooled reservoir where it was re-circulated through the mill. The mill was operated in this recirculation mode, keeping the slurry temperature at 35-40° C., for a total of 410 minutes. Using a free or void volume of 262 ml in the mill, a residence time of 90 minutes was calculated. The product slurry was filtered through a 20 micron polypropylene cartridge filter to give 1185 g of milled ganaxolone slurry. The particle size (D50) measured on a Horiba LA 910 was 164 nm without sonication/153 nm with 1 min. sonication at low power. After 7 days the particle size increased to 320 nm/309 nm sonicated. The D50 did not change after this curing period for the duration of all other studies conducted with this formulation.

Example 52

Milling of Aqueous Ganaxolone Dispersion without Complexing Agent for Solid Dosage Form Ganaxolone was wet milled in a 600 ml chamber using a DYNO-Mill KDL equipped with four 64 mm polyurethane agitator discs. The mill was operated at 4000 RPM or a tip speed of 15 m/sec. The mill was loaded with 88 vol % of 0.4 mm yttrium stabilized zirconium oxide beads. The milling slurry (1200 gm) contained 25 wt % ganaxolone, 5 wt % hydroxypropylmethyl cellulose (Pharmacoat 603), 0.3% sodium lauryl sulfate and 0.033 wt % simethicone emulsion (30% in water, Dow Corning Q7-2587). This slurry was circulated through the mill via a peristaltic pump and returned to a cooled reservoir where it was re-circulated through the mill. The mill was operated in this recirculation mode, keeping the slurry temperature at 40 to 50° C., for a total of 340 minutes. Using a free or void volume of 262 ml in the mill, a residence time of 75 min. is calculated. The product slurry was filtered through a 20 micron polypropylene cartridge filter to give 1271 gm of milled ganaxolone slurry. The particle size (D50) measured on a Horiba LA 910 was 103 nm/102 nm sonicated. After 7 days the particle size increased slightly to 136 nm/112 nm sonicated.

Example 53

Immediate Release Ganaxolone 300 mg Capsules with and without Complexing Agent

Suspensions (1200 grams) in water containing 25 wt % ganaxolone, 5.0% wt % hydroxypropyl methylcellulose (Pharmacoat 603), 0.0333 wt % of 30% simethicone emulsion, and 0.2 wt % sodium lauryl sulfate, either with 0.05 wt % methylparaben (capsule Ex. 1) or with no methylparaben (capsule Ex. 2, 5.2 wt % of HPMC instead of 5 wt %) are prepared. Each wt % is based on the total weight of the suspension.

The ganaxolone particles are milled using conditions as described in Example 51. For formulations with complexing agent (Capsule Form 1), ganaxolone nanoparticles having a particle size (D50) of about 120 nm as measured by Horiba LA 910 particle size analyzer are obtained immediately after milling. This volume-weighted-median particle size grows to about 220 nm after 7 days of curing at ambient temperature, indicating that ganaxolone complex is formed. The D50 does not change after this curing period for the duration of the study. For Capsule Form 2 (without complexing agent), ganaxolone nanoparticles having the same particle size (D50) (about 120 nm) are obtained immediately after milling.

Sucrose (48.5 g) and NaCl (6.5 g) (together about 13 wt % of solids) and water (800 ml) is added to each of the ganaxolone suspensions for Capsule Form 1 and 2 and the resulting mixtures are homogenized for 20 minutes for spray drying. The compositions of the mixtures to be spray dried are given in Table 28.

TABLE 28

Composition of spray mixture prior to spray layering

| | Capsule Example 1 Ganaxolone Complex | | Capsule Example 2 Ganaxolone (No Paraben) | |
|---|---|---|---|---|
| Component | Weight, gram | Wt %/ total solid wt, % | Weight, gram | Wt % based on total solid weight, % |
| Ganaxolone | 300 | 71.7 | 300 | 71.4 |
| HPMC | 60 | 14.3 | 62.4 | 14.9 |
| Simethicone | 0.12 | 0.03 | 0.12 | 0.03 |
| SLS | 2.4 | 0.57 | 2.4 | 0.57 |
| Methylparaben | 0.60 | 0.14 | 0 | 0 |
| Sucrose | 48.5 | 11.6 | 48.5 | 11.5 |
| Sodium chloride | 6.5 | 1.6 | 6.5 | 1.5 |
| Total | 418.12 | 100 | 419.92 | 100 |

For each of Capsule Form 1 and 2, 100 grams of microcrystalline cellulose (MCC) beads (e.g. Celsphere, 30/35 mesh) are added to a Glatt GPCG-3 fluidized bed with Wurster column insert (4 inch), inlet temperature of about 55° C. and air temp of about 40° C. (total air volume approx. 175 cubic cm/hr). About 2000 grams of each spray mixture are sprayed (bottom spray) through 1.2 mm nozzles at 11 mls/ min and 1.5 bar of pressure until a layering of about 400 wt % is achieved as compared to initial beads weight. The theoretical compositions of the spray layered ganaxolone complex particles (Capsule Form 1) and ganaxolone particles (Capsule Form 2) are shown in Table B. Actual Spray layering yields have been >90% theoretical for both form 1 and 2.

TABLE 29

Composition of spray layered particles after spray drying

| Component | Capsule Form 1 Ganaxolone Complex | | Capsule Form 2 Ganaxolone (No Methyl Paraben) | |
|---|---|---|---|---|
|  | Weight, gram | Wt %/ total solid wt, % | Weight, gram | Wt % based on total solid weight, % |
| Ganaxolone | 300 | 57.9 | 300 | 57.7 |
| HPMC | 60 | 11.6 | 62.4 | 12.0 |
| Simethicone | 0.12 | 0.02 | 0.12 | 0.02 |
| SLS | 2.4 | 0.46 | 2.4 | 0.46 |
| Methylparaben | 0.60 | 0.12 | 0 | 0 |
| Sucrose | 48.5 | 9.4 | 48.5 | 9.3 |
| NaCl | 6.5 | 1.25 | 6.5 | 1.25 |
| MCC beads | 100 | 19.3 | 100 | 19.2 |
| Total | 518.12 | 100 | 519.92 | 100 |

The spray layered ganaxolone complex particles (Capsule Form 1) or ganaxolone particles (Capsule Form 2) are then filled into gelatin capsules with a fill weight of 518-520 mg coated beads to achieve a 300 mg dose.

Examples 54

Delayed Release Ganaxolone 300 mg Capsules (with and without Complexing Agent)

Ganaxolone containing immediate release beads (500 g, Capsule Form 1) or ganaxolone multiparticulates (500 g, Capsule Form 2) prepared as described in Example 53 and as shown in Table 30 are loaded directly into a rotary granulator/coater (Freund CF-360 granulator) for enteric coating. The rotating particle bed is sprayed with a coating solution containing 50 wt % Eudragit® L 30-D55, 2.5 wt % talc, 1.5 wt % dibutyl sebecate, 20 wt % ethanol, 23.5 wt % isopropyl alcohol, and 2.5 wt % water. A coating level of about 8 wt % is achieved. The ganaxolone content in each coated bead is about 53.4 wt % based on the total weight of the coated beads.

About 295 mg of uncoated capsule Form 1 or 2 and 240 mg coated beads from capsule Form 1 or 2 thus obtained are hand-filled into gelatin capsule shells, respectively, to form modified release ganaxolone complex 300 mg capsules (Capsule Form 3) or ganaxolone 300 mg modified release capsules without methylparaben (Capsule Form 4). These particulates are substantially insoluble in the stomach due to the enteric coating but substantially soluble in the intestine. The total capsule fill weight is 565 mg.

Example 55

Pulsatile Release Ganaxolone 300 mg Capsules (with and without Complexing Agent)

For Capsule Form 5, uncoated ganaxolone beads obtained for Capsule Form 1 and as described in Table 29 are mixed with coated ganaxolone obtained for Capsule Form 3 (Example 54) at a 60 wt % to 40 wt % ratio to obtain a mixture. About 540 mg of the blended mixture is hand-filled in a hard gelatin capsule to obtain a pulsatile ganaxolone complex 300 mg capsule.

Similarly, for Capsule Form 6, uncoated ganaxolone multiparticulates obtained for Capsule Form 2 and as described in Table 29 are mixed with coated ganaxolone multiparticulates obtained for Capsule Form 4 at a 40 wt % to 60 wt % ratio to obtain a mixture. The ganaxolone content in the mixture is about 55.5 wt %. About 540 mg of the blended mixture is filled in a gelatin capsule to obtain a pulsatile ganaxolone 300 mg capsule (without complexing agent).

Examples 56

Ganaxolone 300 mg Capsules in Swelling Plug Devices (with and without Complexing Agent)

About 520 mg of the beads obtained above in Example 53, Capsule Forms 1 and 2, are hand-filled into a swelling plug device as described previously. The half-capsule shell is made from a poly(methylmethacrylate) material which does not dissolve in the stomach. The open end of the capsule shell is plugged with a cylindrical plug formed from a co-poly(alkylene oxide) crosslinked by reaction with unsaturated cyclic ether group. The plugged capsule half is finally sealed with a water-soluble gelatin to obtain ganaxolone complex 300 mg capsule (Capsule Form 7) and ganaxolone 300 mg capsule (without methyl paraben) (Capsule Form 8).

Example 57

Delayed Release Ganaxolone 300 mg Capsules in Swelling Plug Devices (with and without Complexing Agent)

The sealed devices obtained in Example 56, with and without complexing agent, are further coated with an enteric coating to obtain delayed release ganaxolone complex 300 mg device (Capsule Form 9) and ganaxolone 300 mg device (without methylparaben) (Capsule Form 10). For example, the sealed devices are coated in a Hi-Coater (Vector Corp., Marion, Iowa, USA) with a coating solution containing 50 wt % Eudragit® L 30-D55, 2.5 wt % talc, 1.5 wt % dibutyl sebecate, 20 wt % ethanol, 23.5 wt % isopropyl alcohol, and 2.5 wt % water. A coating level of about 10 wt % is achieved. The coated devices are substantially insoluble in the stomach but substantially release all ganaxolone in the intestine Example 58

Pulsatile Release Ganaxolone Tablets Containing a Modified Release Inner Core and an Immediate Release Coating The following is the process for preparing pulsatile release ganaxolone tablets in accordance with the invention. In this formulation the relative amounts of water-soluble film-forming substance (polyvinylpyrrolidone) and water-insoluble film-forming substance (ethylcellulose) in the second coat of the encapsulated pellets are in the ratio of 1:20.

Ganaxolone particle suspension formulation (12.6% ganaxolone, 2.6% HPMC, 0.026% SLS, 0.018% simethicone emulsion (30% simethicone in water), 0.3% sodium chloride and 2.4% sucrose is dried by rotary evaporation and spray layered onto sucrose beads. The spray layered form is prepared by evaporating the layering slurry onto sugar beads (Paulaur 30/35 mesh) through a fluidized bed coating process yielding approximately 60% ganaxolone loading (% wt GNX/% total bead wt).

The resulting spray layered beads are dried (40° C., 5-10 hr.) and screened, first through a 12-mesh screen to remove aggregates and then over a 20-mesh screen to remove fines.

The ganaxolone containing beads (25 kg) are tumbled in a coating pan and simultaneously dusted with talc (USP, 1.28 kg.) containing blue dye (FD & C Blue No. 1 Lake Dye, 0.0129 kg.) and sprayed with a solution of polyvinylpyrrolidone (0.0570 kg.) and ethylcellulose (50 c.p.s., 1.14 kg.) in ethanol (alcohol, 95%, 27.3 kg). The second coat as thus constituted consists of 2% water-soluble film-forming substance, 46% water-insoluble film forming substance and 52% dusting powder. The resulting encapsulated beads are dried (40° C.) to a moisture content between 0.6% and 1.0% and screened successively through 12-mesh and 20-mesh screens. The encapsulated beads as thus constituted of sugar beads, ganaxolone particles as first coat and PVP, ethylcellulose second coat.

A mixture of anhydrous lactose (4 kg.), microcrystalline cellulose (5.14 kg.), ethylcellulose (50 c.p.s., 2.8 kg.) and hydrogenated vegetable oil (1.19 kg.) is milled, and blended with 25 kg of encapsulated ganaxolone beads. The resulting blend is compressed into tablets, each weighing 700 mg and each containing 300 mg of ganaxolone. The tableting mixture as thus constituted consists of 17.5% diluent, 22.7% diluent-binder, 12% binder and 5.22% hydrophobic lubricant and 42.5% ganaxolone. The tablets as thus constituted consist of encapsulated beads and tableting mixture.

Example 59

Enterically Coated Ganaxolone Tablets

Ganaxolone particle suspension formulation Ex-52 after curing for 7 days with the addition of 0.05% methylparaben is prepared as a spray granulate containing sucrose (3%) and sodium chloride (1.5%). The resulting granulate is dried (40° C., 5-10 hr.) and screened, first through a 12-mesh screen to remove aggregates and then over a 20-mesh screen to remove fines.

Prosolv 90, Ganaxolone spray granulate, and Dipotassium Phosphate Powder, are added sequentially into a Bohle Bin Blender (BL07C, Warminster, Pa., USA) and blended for 10±0.1 minutes at 11±1 rpm. Additional Prosolv 90 and Sodium Starch Glycolate are added and blended for 10±0.1 minutes at 11±1 rpm. The material is then milled and then passed through a 0.5 mm screen (35 Mesh).

| Blend Component | Weight | % w/w |
|---|---|---|
| Silicified Microcrystalline Cellulose, NF (Prosolv 90) | 4.255 kg | 37.0 |
| Sodium Starch Glycolate, NF, EP | 0.230 kg | 2.00 |
| Sodium Chloride | 0.287 kg | 2.5 |
| Magnesium Stearate | 0.0575 kg | 0.5 |
| Dipotassium Phosphate Powder, USP, PE | 0.230 kg | 2.00 |
| Ganaxolone spray granulate | 6.44 kg | 56.0 |
| Totals | 11.5 kg | 100.0 |

The Ganaxolone Blend is loaded into a tablet compressing machine, such as a Fette 1200 B Tool Tablet Press (TP06) or equivalent, and tablets are formed using oval upper and lower punches. Tablets are obtained having an average core tablet weight of 750.0 mg (containing approx. 300 mg ganaxolone) with average acceptable upper and lower tablet weight limits of ±5.0%.

Friability is determined by Current USP <1216> at the beginning and end of each compression run and is NMT 0.5%. Disintegration times are determined using Current USP <701> at the beginning and end of each compression batch. Disintegration time is NMT 5 minutes.

An enteric coat is applied to the tablet cores as follows: The enteric coating comprising Opadry® Enteric from Colorcon® and the over coat comprising Opadry® clear applied sequentially as aqueous coating suspensions using a coating pan. The tablet cores are preheated to 46° C. (Exhaust air temperature). The pan speed is adjusted to provide adequate tablet flow and the coating suspensions are sprayed onto the tablets at an atomizing air pressure of 18-30 psi; an inlet air temperature of 60-70° C. for over coat, and of 42-50° C. for the enteric coat; an exhaust air temperature of 40 to 50° C. for the over coat and 30 to 35° C. for the enteric coat; a spray rate of 15 to 50 ml/min.; and an inlet air flow of 175 to 300 CFM. One of skill in the art will understand that the processing parameters for coating are dependent in part upon the size of the batch to be coated and can be adjusted accordingly. The enteric coating should be applied so that a tablet core weight gain of 8-15% w %/tablet core weight is achieved. Cellulose acetate phthalate, hydroxypropyl methylcellulose phthalate, polyvinyl acetate phthalate, a methacrylic acid copolymer, hydroxypropyl methylcellulose acetate succinate, shellac, cellulose acetate trimellitate, or a combination comprising one or more of the foregoing enteric polymers may be used in place of the Opadry Enteric coating.

Example 60

Ganaxolone Immediate Release Tablet

Ganaxolone tablet core are prepared as described above in Example 59. Over coat comprising Opadry® clear is applied as an aqueous coating suspensions using a coating pan. The tablet cores are preheated to 46° C. (Exhaust air temperature). The pan speed is adjusted to provide adequate tablet flow and the coating suspensions are sprayed onto the tablets at an atomizing air pressure of 18-30 psi; an inlet air temperature of 60-70° C., an exhaust air temperature of 40 to 50° C., a spray rate of 15 to 50 ml/min.; and an inlet air flow of 175 to 300 CFM. A color coating such as Colorcon Opaspray or Opalux may be applied prior to the final application of Opadry clear to provide a colored tablet.

Example 62

Enterically Coated Ganaxolone Tablets Containing Sugar Beads

Ganaxolone particle suspension formulation with or without complexing agent is prepared as a described in Examples 52 (Ex-52A, containing 0.05% methylparaben and cured for 7 days) and 52 (Ex-52, no complexing agent). To each of these compositions is added sucrose (3%) and sodium chloride (1.5%). Sufficient water is added as in Example 53 to make a dispersion containing about 18% solid content.

For each of the particle suspensions 100 grams of sugar beads (e.g. Paulaur 30/35 mesh) are added to a Glatt GPCG-3 fluidized bed with Wurster column insert (4 inch), inlet temperature of about 55° C. and air temp of about 40° C. (total air volume approx. 175 cubic cm/hr). About 2000 grams of each spray mixture are sprayed (bottom spray) through 1.2 mm nozzles at 10 mls/min and 1.5 bar of pressure until a layering of about 400 wt % is achieved as compared to initial sugar beads weight. The compositions of the spray layered ganaxolone particles on a sugar bead containing 60% Ganaxolone or ganaxolone complex particles by total bead weight is achieved. Lactose monohydrate, ganaxolone beads, and dipotassium phosphate powder, are added sequentially into a Bohle Bin Blender (BL07C, Warminster, Pa., USA) and blended for 10±0.1 minutes at 11±1 rpm. Additional Prosolv 90 and sodium starch glycolate are added and blended for 10±0.1 minutes at 11±1 rpm. The material is then milled and then passed through a 0.5 mm screen (35 Mesh).

| Blend Component | Weight | % w/w |
|---|---|---|
| Lactose monohydrate | 3.128 kg | 27.2 |
| Sodium Starch Glycolate, NF, EP | 0.230 kg | 2.00 |
| Sodium Chloride | 0.287 kg | 2.5 |
| Magnesium Stearate | 0.0575 kg | 0.5 |
| Dipotassium Phosphate Powder, USP, PE | 0.230 kg | 2.00 |
| Ganaxolone spray layered beads | 7.567 kg | 65.8 |
| Totals | 11.5 kg | 100.0 |

The Ganaxolone Blend is loaded into a tablet compressing machine, such as a Fette 1200 B Tool Tablet Press (TP06) or equivalent, and tablets are formed using oval upper and lower punches. Tablets are obtained having an average core tablet weight of 790 mg (containing 300 mg ganaxolone) with average acceptable upper and lower tablet weight limits of ±5.0%.

Friability are disintegration times are as described in Example 59.

An enteric coat is applied to the tablet cores as follows: The enteric coating comprising Opadry® Enteric from Colorcon® and the over coat comprising Opadry® clear applied sequentially as aqueous coating suspensions using a coating pan. The tablet cores are preheated to 46° C. (Exhaust air temperature). The pan speed is adjusted to provide adequate tablet flow and the coating suspensions are sprayed onto the tablets at an atomizing air pressure of 18-30 psi; an inlet air temperature of 60-70° C. for over coat, and of 42-50° C. for the enteric coat; an exhaust air temperature of 40 to 50° C. for the over coat and 30 to 35° C. for the enteric coat; a spray rate of 15 to 50 ml/min.; and an inlet air flow of 175 to 300 CFM. One of skill in the art will understand that the processing parameters for coating are dependent in part upon the size of the batch to be coated and can be adjusted accordingly. The enteric coating should be applied so that a tablet core weight gain of 8-15% w %/tablet core weight is achieved. Cellulose acetate phthalate, hydroxypropyl methylcellulose phthalate, polyvinyl acetate phthalate, a methacrylic acid copolymer, hydroxypropyl methylcellulose acetate succinate, shellac, cellulose acetate trimellitate, or a combination comprising one or more of the foregoing enteric polymers may be used in place of the Opadry Enteric coating.

Example 63

Pharmacokinetic Analysis of 200 Mg of Ganaxolone Complex Suspension (50 Mg/Ml) Containing Pva Administered in 6 Healthy Volunteers in the Fasted State Following an overnight fast of at least 10 hours, 6 healthy subjects were administered ganaxolone (4 ml of a 50 mg/ml suspension manufactured as in example 50 as the ganaxolone complexed composition) with 240 mL (8 fluid ounces) of water. No food allowed for at least 4 hours post-dose. Water was allowed as desired except for one hour before and after drug administration. Other oral fluids (juices, coffee, carbonated beverages etc.) were not permitted from 4 hours pre-dose to 4 hours post-dose. Grapefruits or grapefruit juice intake was prohibited during the entire study. A standardized meal was provided at 4 hours post-dose.

Blood samples (4 ml) for PK analysis were collected at 0.5, 1, 1.5, 2, 3, 4, 6, 8, and 12 hours following dosing using dipotassium EDTA as the anti-coagulant. Plasma was generated by centrifugation at around 4-8 k RPM for 15 minutes at 0° C., frozen below −20° C. for storage and shipping and analyzed using a validated HPLC/MS/MS/MS method with an LOQ of 1 ng/ml. Results yielded a mean Cmax of 37±25 ng/ml and an $AUC_{(0-24)}$ of 184±104 ng*h/ml.

Example 64

Effect of Freeze/Thaw Cycles on the Stability of Ganaxolone Formulations with and without a Complexing Agent Ganaxolone formulations Ex-51 and Ex-52 (with and without complexing agent as described in Examples 51 and 52 respectively), were tested for freeze thaw stability as follows:

10 gm of each formulation was placed into a 25 ml HDPE scintillation vial with HDPE cap. These were placed into a 500 ml glass beaker containing approx. 1 inch of Styrofoam packing (to slow freezing process) and placed into an insulated carton containing crushed dry ice. The vials were stored overnight and then thawed at room temperature for 1 hour. This process was repeated for the same vials 2× comprising 3 freeze/thaw cycles. The particle size for each formulation was measured by the method already described and compared to control material stored at room temperature in the same container closure system.

TABLE 30

Particle size (D50) before and after freezing/thaw cycles for ganaxolone particles with and without a complexing agent (methylparaben)

| Formulation | Initial D50 (nm) Before/after 1 min sonication | D50 (nm) after 3 freeze/ thaw cycles Before/ after 1 min sonication |
|---|---|---|
| Ex-51 | 320/298 | 319/310 |
| Ex-52 | 149/140 | 822/341 |

We claim:

1. Solid stabilized particles comprising ganaxolone, a hydrophilic polymer, a wetting agent, and an effective amount of a complexing agent that stabilizes particle growth after an initial particle growth and endpoint is reached, the complexing agent being a small organic molecule having a molecular weight less than 550 and containing a moiety selected from the group consisting of a phenol moiety, an aromatic ester moiety and an aromatic acid moiety, wherein the stabilized particles have a volume weighted median diameter (D50) of the particles is from about 50 nm to about 500 nm and the concentration of ganaxolone in the solid stabilized particles is at least 50% by weight.

2. The solid stabilized particles of claim 1, wherein the hydrophilic polymer is in an amount from about 3% to about 50%, w/w, based on the weight of the solid particles.

3. The solid stabilized particles of claim 2, wherein the wetting agent is in an amount from about 0.01% to about 10%, w/w, based on the weight of the solid particles.

4. The solid stabilized particles of claim 2, wherein the stabilized particles exhibit an increase in volume weighted median diameter (D50) of not more than about 150% when the particles are dispersed in simulated gastric fluid (SGF) or simulated intestinal fluid (SIF) at a concentration of 0.5 to 1 mg ganaxolone/mL and placed in a heated bath at 36° to 38° C. for 1 hour as compared to the D50 of the stabilized particles when the particles are dispersed in distilled water under the same conditions, wherein the volume weighted median diameter (D50) of the stabilized particles dispersed in SGF or SIF is less than about 750 nm.

5. The solid stabilized particles of claim 1, wherein the stabilized particles exhibit an increase in volume weighted median diameter (D50) of not more than about 150% when the formulation is dispersed in 15 mL of SGF or SIF at a concentration of 0.5 to 1 mg ganaxolone/mL as compared to the D50 of the stabilized particles when the particles are dispersed in distilled water under the same conditions, wherein the volume weighted median diameter (D50) of the stabilized particles dispersed in SGF or SIF is less than about 750 nm.

6. The solid stabilized particles of claim 1, wherein the ganaxolone is present in an amount greater than 50% to about 80%, based on the weight of the particles.

7. The solid stabilized particles of claim 6, wherein the stabilized particles exhibit an increase in volume weighted median diameter (D50) of not more than about 150% when the particles are dispersed in simulated gastric fluid (SGF) or simulated intestinal fluid (SIF) at a concentration of 0.5 to 1 mg ganaxolone/mL and placed in a heated bath at 36° to 38° C. for 1 hour, as compared to the D50 of the stabilized particles when the particles are dispersed in distilled water under the same conditions, wherein the volume weighted median diameter (D50) of the stabilized particles dispersed in SGF or SIF is less than about 750 nm.

8. The solid stabilized particles of claim 1 in the form of a powder.

9. The solid stabilized particles of claim 1, wherein the particles are incorporated into a dosage form selected from the group consisting of a tablet or capsule.

10. The solid stabilized particles of claim 1, wherein the volume weighted median diameter (D50) of the stabilized particles dispersed in distilled water is from about 100 nm to about 350 nm.

11. The solid stabilized particles of claim 1, wherein the complexing agent is selected from the group consisting of parabens, benzoic acid, methyl anthranilate, and pharmaceutically acceptable salts thereof and mixtures thereof.

12. The solid stabilized particles of claim 1, wherein the paraben is selected from the group consisting of methylparaben, ethylparaben, propylparaben, pharmaceutically acceptable salts thereof and mixtures thereof.

13. The solid stabilized particles of claim 1, wherein the hydrophilic polymer is selected from the group consisting of a cellulosic polymer, a vinyl polymer and mixtures thereof.

14. The solid stabilized particles of claim 13, wherein the cellulosic polymer is a cellulose ether.

15. The solid stabilized particles of claim 13, wherein the cellulose ether is hydroxypropylmethylcellulose.

16. The solid stabilized particles of claim 13, wherein the vinyl polymer is polyvinyl alcohol.

17. The solid stabilized particles of claim 1, wherein the wetting agent is selected from the group consisting of sodium lauryl sulfate, a pharmaceutically acceptable salt of docusate, and mixtures thereof.

18. The solid stabilized particles of claim 1, wherein the particles are incorporated into a solid dosage form, further comprising at least one pharmaceutically acceptable excipient selected from the group consisting of an ionic dispersion modulator, an water soluble spacer, a disintegrant, a binder, a surfactant, a plasticizer, a lubricant, and any combinations or mixtures thereof.

19. The solid stabilized particles of claim 18, wherein the pharmaceutically acceptable excipient comprises an ionic dispersion modulator.

20. The solid stabilized particles of claim 19, wherein the ionic dispersion modulator is in an amount from about 1% to about 50%, w/w, based on the weight of the solid particles.

21. The solid stabilized particles of claim 19, wherein the ionic dispersion modulator is a salt.

22. The solid stabilized particles of claim 19, wherein the ionic dispersion modulator is an inorganic salt is selected from the group consisting of a magnesium salt, a calcium salt, a lithium salt, a potassium salt, a sodium salt and mixtures thereof.

23. The solid stabilized particles of claim 19, wherein the ionic dispersion modulator is an organic salt is selected from the group consisting of a citrate salt, a succinate salt, a fumarate salt, a malate salt, maleate salt, a tartrate salt, a glutarate salt, a lactate salt and mixtures thereof.

24. The solid stabilized particles of claim 18, wherein the pharmaceutically acceptable excipient comprises a water soluble spacer.

25. The solid stabilized particles of claim 24, wherein the water soluble spacer is in an amount from about 2% to about 60%, w/w, based on the weight of the solid particles.

26. The solid stabilized particles of claim 18, wherein the water soluble spacer is a saccharide or an ammonium salt.

27. The solid stabilized particles of claim 26, wherein the saccharide is selected from the group consisting of fructose, sucrose, glucose, lactose, mannitol and mixtures thereof.

28. The solid stabilized particles of claim 18, wherein the disintegrant is selected from the group consisting of cross-linked sodium carboxymethylcellulose, crospovidone and any combinations or mixtures thereof.

29. The solid stabilized particles of claim 18, wherein the surfactant is a polysorbate.

30. The solid stabilized particles of claim 18, wherein the plasticizer is polyethylene glycol.

31. The solid stabilized particles of claim 1, incorporated into a tablet or capsule, wherein the dosage form provides a ratio of mean blood plasma fed $AUC_{(0-\tau)}$ to fasted $AUC_{(0-\tau)}$ from about 1:1 to about 4:1.

32. The solid stabilized particles of claim 1, wherein the dosage form provides a ratio of mean blood plasma fed Cmax to fasted Cmax from about 1.5:1 to about 7:1.

33. The solid stabilized particles of claim 1, wherein the particles have a volume weighted median diameter (D50) from about 50 nm to about 1000 nm, and the dosage form provides a mean blood plasma AUC 0-24 hours from about 100 to about 375 ng*h/ml when a dose of 200 mg to 500 mg of the ganaxolone is orally administered to adult subjects in the fasted state.

34. The solid stabilized particles of claim 1, wherein the dosage form provides a mean blood plasma Cmax from about 25 to about 70 ng/ml when a dose of 200 mg to 500 mg of the ganaxolone is orally administered to adult subjects in the fasted state.

35. The solid stabilized particles of claim 1, wherein the dosage form providing a mean blood plasma AUC (0-48) hours from about 400 to about 1200 ng*h/ml when a dose of 200 mg to 500 mg of the ganaxolone is orally administered to adult subjects in the fed state.

36. The solid stabilized particles of claim 1, wherein the dosage form providing a mean blood plasma Cmax from about 60 to about 250 ng/ml when a dose of 200 mg to 500 mg of the ganaxolone is orally administered to adult subjects in the fed state.

37. The solid stabilized particles of claim 1, wherein the dosage form provides a mean blood plasma Cmax/Cmin ratio of not greater than about 4 to 1 at steady state with a dose of 200 to 500 mg ganaxolone to adult subjects in the fed or fasted state.

38. The stabilized particles of claim 1, wherein the solid dosage form is an immediate release dosage form.

39. The stabilized particles of claim 1, wherein the solid dosage form is a controlled release dosage form.

40. The solid stabilized particles of claim 39, wherein the particles are incorporated into an oral solid dosage form comprising (i) a controlled release component comprising a first portion of the stabilized particles; and a controlled release material, and (ii) an immediate release component comprising a second portion of the stabilized particles, the first and second portion of stabilized particles having a volume weighted median diameter (D50) of from about 50 nm to about 500 nm.

41. The solid stabilized particles of claim 40, wherein the ratio of ganaxolone in controlled release to immediate release is from about 4:1 to about 1:4.

42. The solid stabilized particles of claim 39, wherein dosage form provides a therapeutic effect for about 8 to about 24 hours after administration.

43. The solid stabilized particles of claim 1, wherein the complexing agent is in an amount from about 0.05% to about 5%, w/w, based on the weight of the solid particles.

44. The solid stabilized particles of claim 1, wherein the complexing agent comprises methylparaben or a salt thereof.

45. The solid stabilized particles of claim 1, wherein the complexing agent comprises benzoic acid or a salt thereof.

46. The solid stabilized particles of claim 1, wherein the complexing agent comprises methyl anthranilate.

47. The solid stabilized particles of claim 1, which includes from about 200 mg to about 800 mg ganaxolone.

48. Solid stabilized particles comprising ganaxolone, a hydrophilic polymer, a wetting agent, and an effective amount of a complexing agent selected from the group of small organic molecules having a molecular weight less than 550 and containing a moiety selected from the group consisting of a phenol moiety, an aromatic ester moiety and an aromatic acid moiety, the stabilized particles having a volume weighted median diameter (D50) of the particles from about 50 nm to about 500 nm, the concentration of ganaxolone in the solid stabilized particles being at least 50% by weight.

49. The solid stabilized particles of claim 48, wherein the ganaxolone is present in an amount greater than 50% to about 80%, based on the weight of the particles.

50. The solid stabilized particles of claim 1, wherein the particles are incorporated into a dosage form selected from the group consisting of a tablet or capsule.

51. The solid stabilized particles of claim 48, wherein the complexing agent is selected from the group consisting of parabens, benzoic acid, methyl anthranilate, and pharmaceutically acceptable salts thereof and mixtures thereof.

* * * * *